US011813336B2

(12) United States Patent
Haupts et al.

(10) Patent No.: US 11,813,336 B2
(45) Date of Patent: Nov. 14, 2023

(54) TARGETED COMPOUNDS FOR THE SITE-SPECIFIC COUPLING OF CHEMICAL MOIETIES COMPRISING A PEPTIDE LINKER

(71) Applicant: Navigo Proteins GmbH, Halle/Saale (DE)

(72) Inventors: Ulrich Haupts, Halle/Saale (DE); Markus Liebscher, Halle/Saale (DE); Erik Fiedler, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 452 days.

(21) Appl. No.: 16/098,600

(22) PCT Filed: May 4, 2017

(86) PCT No.: PCT/EP2017/060650
§ 371 (c)(1),
(2) Date: Nov. 2, 2018

(87) PCT Pub. No.: WO2017/191252
PCT Pub. Date: Nov. 9, 2017

(65) Prior Publication Data
US 2019/0117791 A1    Apr. 25, 2019

(30) Foreign Application Priority Data

May 4, 2016 (EP) .................................. 16168255
Mar. 17, 2017 (EP) .................................. 17161514

(51) Int. Cl.
A61K 47/68 (2017.01)
A61K 47/65 (2017.01)
C07K 14/435 (2006.01)
C07K 16/28 (2006.01)
C07K 16/32 (2006.01)
G01N 33/533 (2006.01)

(52) U.S. Cl.
CPC .......... *A61K 47/6889* (2017.08); *A61K 47/65* (2017.08); *C07K 14/435* (2013.01); *C07K 16/2863* (2013.01); *C07K 16/32* (2013.01); *G01N 33/533* (2013.01); *C07K 2317/92* (2013.01); *C07K 2317/94* (2013.01); *C07K 2319/00* (2013.01); *C07K 2319/035* (2013.01); *C07K 2319/30* (2013.01); *C07K 2319/33* (2013.01); *C07K 2319/70* (2013.01)

(58) Field of Classification Search
CPC ............... A61K 47/65; A61K 47/6889; C07K 2318/10; C07K 2318/20
See application file for complete search history.

(56) References Cited

U.S. PATENT DOCUMENTS

| 4,873,192 | A | 10/1989 | Kunkel |
| 5,789,166 | A | 8/1998 | Bauer et al. |
| 5,958,684 | A | 9/1999 | Van Leeuwen et al. |
| 6,217,863 | B1 | 4/2001 | Godavarti et al. |
| 6,569,677 | B1 | 5/2003 | Legrand et al. |
| 6,620,587 | B1 | 9/2003 | Taussig et al. |
| 6,673,901 | B2 | 1/2004 | Koide |
| 6,799,121 | B2 | 9/2004 | Chu et al. |
| 7,250,297 | B1 | 7/2007 | Beste et al. |
| 7,273,924 | B1 | 9/2007 | Neri et al. |
| 7,393,918 | B2 | 7/2008 | Golemi-Kotra et al. |
| 7,601,803 | B1 | 10/2009 | Fiedler et al. |
| 7,838,629 | B2 | 11/2010 | Fiedler et al. |
| 7,851,599 | B2 | 12/2010 | Menrad et al. |
| 8,097,254 | B2 | 1/2012 | Neri et al. |
| 8,404,814 | B2 | 3/2013 | Neri et al. |
| 8,426,357 | B2 | 4/2013 | Kraehmer et al. |
| 8,455,625 | B2 | 6/2013 | Neri et al. |
| 8,592,144 | B2 | 11/2013 | Fiedler et al. |
| 8,592,179 | B2 | 11/2013 | Schraeml et al. |
| 8,623,373 | B2 | 1/2014 | Zardi et al. |

(Continued)

FOREIGN PATENT DOCUMENTS

AU 2013318928 4/2015
EP 1 591 527 A1 11/2005
(Continued)

OTHER PUBLICATIONS

Skerra (Journal of Molecular Recognition, 2000, vol. 13, pp. 167-187) (Year: 2000).*
Cao et al (Oncogene, 2014, vol. 33, pp. 429-439) (Year: 2014).*
Veendaal et al (PNAS, 2002, vol. 99, pp. 7866-7871) (Year: 2002).*
McCombs and Owen (The AAPS Journal, 2015, vol. 7, pp. 339-351) (Year: 2015).*
Chari et al (Angew. Chem. Int. Ed. 2014, vol. 53, pp. 3796-3872 (Year: 2014).*
Koniev and Wagner (Chem Soc Rev, 2015, vol. 44, pp. 5495-5551) (Year: 2015).*

(Continued)

*Primary Examiner* — Karen A. Canella
(74) *Attorney, Agent, or Firm* — Jenkins, Taylor & Hunt P.A.

(57) ABSTRACT

The invention generally relates to targeted compounds for the site-specific coupling of chemical moieties. The present invention features a targeted compound for the coupling of chemical moieties comprising at least one targeting domain capable of binding a target, and at least one linking moiety of up to 80 amino acids, preferably alanine, proline, and serine, and at least one coupling site consisting of cysteine or a cysteine-rich peptide motif (CXC, CXXC, or CXXXC), and wherein said linking moiety connects the targeting domain and a coupling site and/or wherein a linking moiety connects two coupling sites. The invention further features fusion proteins with ubiquitin muteins (Affilin @) as targeting domain. The invention also relates to the use of the targeted compounds for medical applications, in treatment or diagnosis of diseases.

13 Claims, 11 Drawing Sheets

Specification includes a Sequence Listing.

(56) References Cited

U.S. PATENT DOCUMENTS

| | | |
|---|---|---|
| 8,748,351 B2 | 6/2014 | Kunert et al. |
| 8,790,895 B2 | 7/2014 | Fiedler et al. |
| 8,791,238 B2 | 7/2014 | Fiedler et al. |
| 8,921,304 B2 | 12/2014 | Steuernagel et al. |
| 9,492,572 B2 | 11/2016 | Nerkamp et al. |
| 9,920,098 B2 | 3/2018 | Yoshida et al. |
| 10,808,042 B2 | 10/2020 | Haupts |
| 10,858,405 B2 | 12/2020 | Bosse-Doenecke et al. |
| 11,230,576 B2 | 1/2022 | Knick et al. |
| 2003/0045681 A1 | 3/2003 | Neri et al. |
| 2003/0073623 A1 | 4/2003 | Drmanac et al. |
| 2004/0043386 A1 | 3/2004 | Pray et al. |
| 2006/0058510 A1 | 3/2006 | Skerra et al. |
| 2006/0099686 A1 | 5/2006 | Fiedler et al. |
| 2007/0015248 A1 | 1/2007 | Anton et al. |
| 2007/0111287 A1 | 5/2007 | Fiedler et al. |
| 2007/0189963 A1 | 8/2007 | Neri et al. |
| 2007/0248536 A1 | 10/2007 | Fiedler et al. |
| 2007/0286843 A1 | 12/2007 | Pfizenmaier et al. |
| 2008/0171851 A1 | 7/2008 | Fiedler et al. |
| 2010/0119446 A1 | 5/2010 | Grabulovski et al. |
| 2010/0130720 A1 | 5/2010 | Schraeml et al. |
| 2011/0162095 A1 | 6/2011 | Hill et al. |
| 2012/0244596 A1 | 9/2012 | Skerra et al. |
| 2012/0301393 A1 | 11/2012 | Steuernagel et al. |
| 2013/0011334 A1 | 1/2013 | Steuernagel et al. |
| 2013/0096276 A1 | 4/2013 | Yoshida et al. |
| 2013/0097737 A1 | 4/2013 | Kovalic et al. |
| 2013/0157878 A1 | 6/2013 | Kunert et al. |
| 2014/0135476 A1 | 5/2014 | Hall et al. |
| 2014/0219959 A1 | 8/2014 | Nerkamp et al. |
| 2014/0243254 A1* | 8/2014 | Hersel ............... A61K 47/65 530/331 |
| 2015/0183846 A1 | 7/2015 | Lange et al. |
| 2018/0030098 A1 | 2/2018 | Bosse-Doenecke et al. |
| 2018/0030140 A1 | 2/2018 | Bosse-Doenecke et al. |
| 2018/0194819 A1 | 7/2018 | Fiedler et al. |
| 2018/0273636 A1 | 9/2018 | Settele et al. |
| 2018/0305463 A1 | 10/2018 | Haupts |
| 2019/0177376 A1 | 6/2019 | Knick et al. |
| 2021/0179678 A1 | 6/2021 | Fiedler et al. |
| 2022/0112236 A1 | 4/2022 | Fiedler et al. |
| 2022/0127312 A1 | 4/2022 | Fiedler et al. |

FOREIGN PATENT DOCUMENTS

| | | |
|---|---|---|
| EP | 2 532 672 A2 | 12/2012 |
| EP | 2 727 942 A1 | 5/2014 |
| EP | 2 738 180 | 6/2014 |
| EP | 2829552 A1 | 1/2015 |
| RU | 2134696 C1 | 8/1999 |
| WO | WO 2005/044845 A2 | 5/2005 |
| WO | WO 2007/054120 A1 | 5/2007 |
| WO | WO-2008155134 A1 * | 12/2008 ............. A61K 38/17 |
| WO | WO 2012/171541 A1 | 12/2012 |
| WO | WO 2013/186329 A1 | 12/2013 |
| WO | WO 2014/094799 | 6/2014 |
| WO | WO 2016/079033 | 5/2016 |
| WO | WO 2016/124670 A1 | 8/2016 |
| WO | WO 2016/124702 A1 | 8/2016 |
| WO | WO 2017/013129 | 1/2017 |
| WO | WO 2017/013136 | 1/2017 |
| WO | WO 2017009421 | 1/2017 |
| WO | WO 2018/029157 A1 | 2/2018 |
| WO | WO 2019/030156 A1 | 2/2019 |
| WO | WO 2019/152318 A1 | 8/2019 |
| WO | WO 2020/157281 A1 | 8/2020 |

OTHER PUBLICATIONS

Abedi et al. (1998) Green fluorescent protein as a scaffold for intracellular presentation of peptides. Nucleic Acids Research 26(2):623-630.

Advisory Action corresponding to U.S. Appl. No. 10/030,605 dated Oct. 13, 2006.

Advisory Action corresponding to U.S. Appl. No. 11/732,632 dated Jun. 30, 2010.

Advisory Action corresponding to U.S Appl. No. 12/072,959 dated May 18, 2010.

Baker et al. (1994) Protein Expression Using Cotranslational Fusion and Cleavage of Ubiquitin. The Journal of Biological Chemistry 269(41):25381-25386.

Beal et al. (1996) Surface hydrophobic residues of multiubiquitin chains essential for proteolytic targeting. PNAS 93:861-866.

Beste et al. (1999) Small antibody-like proteins with prescribed ligand specificities derived from the lipocalin fold. PNAS 96:1898-1903.

Birchler et al. (1999) Selective targeting and photocoagulation of ocular angiogenesis mediated by a phage-derived human antibody fragment. Nature Biotechnology 17:984-988.

Bird et al. (1988) Single-Chain Antigen-Binding Proteins. Science. 242:423-426.

Bofill et al. (2005) Engineering Stabilising beta-Sheet Interactions into a Conformationally Flexible Region of the Folding Transition State of Ubiquitin. Journal of Molecular Biology 353(2):373-384.

Bolton et al. (2001) Structure and Properties of a Dimeric N-terminal Fragment of Human Ubiquitin. Journal of Molecular Biology 314(4):773-787.

Borsi et al. (2003) Selective targeted delivery of TNFα to tumor blood vessels. Blood 102(13):4384-4392.

Brinkmann et al. (1993) A recombinant immunotoxin containing a disulfide-stabilized Fv-fragment. PNAS 90:7538-7542.

Brinkmann et al. (1997) Stabilization of a Recombinant Fv Fragment by Base-Loop Interconnection and VH-VL Permutation. Journal of Molecular Biology 268:107-117.

Buchberger et al. (2001) The UBX Domain: A Widespread Ubiquitin-Like Module. Journal of Molecular Biologyy 307(1):17-24.

Burch & Haas (1994) Site-directed mutagenesis of ubiquitin. Differential roles for arginine in the interaction with ubiquitin-activating enzyme. Biochemistry 33(23):7300-7308.

Campion et al. (1990) Biochemical Properties of Site-Directed Mutants of Human Epidermal Growth Factor: Importance of Solvent-Exposed Hydrophobic Residues of the Amino-Terminal Domain in Receptor Binding. Biochemistry 29(42):9988-9993.

Connolly (1983) Solvent-Accessible Surfaces of Proteins and Nucleic Acids. Science 221(4612):709-713.

Corrected Notice of Allowability corresponding to U.S. Appl. No. 11/656,646 dated Sep. 26, 2013.

Database Geneseq online Aug. 18, 2011 (Aug. 18, 2011)Heteromultimeric modified ubiquitin protein, Seq ID 44., XP002756535, retrieved from EBI accession No. GSP:AZJ58575 Database accession No. AZJ58575.

Database Geneseq online Dec. 4, 2014 (Dec. 4, 2014)Anti-EGFR1 antibody light chain-TGF beta RII fusion protein, SEQ: 30., XP002756536, retrieved from EBI accession No. GSP:BBP24113 Database accession No. BBP24113.

Daugherty et al. (1998) Antibody affinity maturation using bacterial surface display. Protein Engineering 11(9):825-832.

De Kruif et al. (1995) Selection and Application of Human Single Chain Fv Antibody Fragments from a Semi-synthetic Phage Antibody Display Library with Designed CDR3 Regions. Journal of Molecular Biology 248:97-105.

Decision to Grant corresponding to Russian Patent Application No. 2012115491/10(023353) dated Nov. 20, 2014.

Deed of Grant corresponding to Australian Patent No. 2010332932 dated May 2, 2013.

Deed of Grant corresponding to Australian Patent No. 2010332938 dated Apr. 4, 2013.

Dikic et al. (2009) Ubiquitin-binding domains—from structures to functions. Nature Reviews 10:659- 671.

Ebersbach et al. (2007) Affilin-Novel Binding Molecules Based on Human (-B-Crystallin, an All (-Sheet Protein Journal of Molecular Biology 372:172-185.

Ecker et al. (1987) Gene Synthesis, Expression, Structures, and Functional Activities of Site-specific Mutants of Ubiquitin. The Journal of Biological Chemistry 262(29):14213-14221.

(56) References Cited

OTHER PUBLICATIONS

Ermolenko et al. (2003) Noncharged amino acid residues at the solvent-exposed positions in the middle and at the C terminus of the alpha-helix have the same helical propensity. Protein Science 12(6):1169-1176.
European Search Report corresponding to European Patent Application No. 06 118 519.5 -2401 dated Apr. 2, 2007.
European Search Report corresponding to European Patent Application No. 09 176 574.3-2401 dated Jan. 18, 2010.
European Search Report corresponding to European Patent Application No. 10 181 802.9-2401 dated Feb. 10, 2011.
Fiedler et al. (2006) Affilintm Molecules: Novel Ligands for Bioseparation. Food and Bioproducts Processing. 84(C1)3-8.
Finucane et al. (1999a) Core-Directed Protein Design. I. An Experimental Method for Selecting Stable Proteins from Combinatorial Libraries. Biochemistry 38:11604-11612.
Finucane et al. (1999b) Core-Directed Protein Design. II. Rescue of a Multiply Mutated and Destabilized Variant of Ubiquitin. Biochemistry 38(36):11613-11623.
Friedman et al. (2009) Engineering and characterization of a bispecific HER2 X EGFR-binding affibody molecule. Biotechnology and applied biochemistry academic press US 54(2):121-131.
Gebauer & Skerra (2009) Engineered protein scaffolds as next-generation antibody therapeutics. Current Opinion in Chemlcal Biology 13(3):245-255.
Grabulovski et al. (2007) A Novel, Non-immunogenic Fyn SH3-derived Binding Protein with Tumor Vascular Tarqetinq Properties. The Journal of Biological Chemistry 282(5):3196-3204.
Guo et al. (2004) Protein tolerance to random amino acid change. PNAS 101(25):9205-9210.
Hanes & Plückthun (1997) In vitro selection and evolution of functional proteins by using ribosome display PNAS 94(10):4937-4942.
Hanes et al. (1998) Ribosome display efficiently selects and evolves high-affinity antibodies in vitro from immune libraries. PNAS 95:14130-14135.
Hanes et al. (2000) Picomolar affinity antibodies from a fully synthetic naive library selected and evolved by ribosome display Nature Biotechnology 18:1287-1292.
He & Taussig (1997) Antibody-ribosome-mRNA (ARM) complexes as efficient selection particles for in vitro display and evolution of antibody combining sites. Nucleic Acids Research 25(24):5132-5134.
Hershko & Ciechanover (1998) The Ubiquitin System. Annu Rev Biochem 67:425-479.
Hey et al. (2005) Artificial, non-antibody binding proteins for pharmaceutical and industrial applications Trends in Biotechnology 23(10):514-522.
Humphrey et al. (1990) Anti-synthetic peptide antibody reacting at the fusion junction of deletion-mutant epidermal growth factor receptors in human glioblastoma. Proc Natl Acad Sci. 87:4207-4211.
International Preliminary Report on Patentability (Chapter I of the Patent Cooperation Treaty) corresponding to International Patent Application No. PCT/EP2007/062375 dated May 19, 2009.
International Preliminary Report on Patentability (Chapter I of the Patent Cooperation Treaty) corresponding to International Patent Application No. PCT/EP2010/069665 dated Jun. 19, 2012.
International Preliminary Report on Patentability (Chapter I of the Patent Cooperation Treaty) correspondina to International Patent Application No. PCT/EP2016/052345 dated Aug. 8, 2017.
International Preliminary Report on Patentability corresponding to International Patent Application No. PCT/EP2004/005730 dated May 13, 2005.
International Preliminary Report on Patentability corresponding to International Patent Application No. PCT/EP2016/067216 dated Jan. 23, 2018.
International Search Report and Written Opinion corresponding to International Application No. PCT/EP2016/066774 dated Sep. 14, 2016.
International Search Report and Written Opinion corresponding to International Application No. PCT/EP2016/067216 dated Oct. 12, 2016.
International Search Report and Written Opinion corresponding to International Patent Application No. PCT/EP2016/052408 dated May 2, 2016.
International Search Report corresponding to International Application No. PCT/EP2016/067207 dated Sep. 29, 2016.
International Search Report corresponding to International Patent Application No. PCT/EP2000/006698 dated Feb. 2, 2001.
International Search Report corresponding to International Patent Application No. PCT/EP2004/005730 dated Oct. 5, 2004.
International Search Report corresponding to International Patent Application No. PCT/EP2005/010932 dated Apr. 11, 2006.
International Search Report corresponding to International Patent Application No. PCT/EP2007/062375 dated Apr. 25, 2008.
International Search Report corresponding to International Patent Application No. PCT/EP2010/069665 dated Apr. 13, 2011.
International Search Report corresponding to International Patent Application No. PCT/EP2010/069674 dated Jun. 17, 2011.
International Search Report corresponding to International Patent Application No. PCT/EP2011/002962 dated Mar. 19, 2012.
International Search Report corresponding to International Patent Application No. PCT/EP2012/061455 dated Oct. 25, 2012.
International Search Report corresponding to International Patent Application No. PCT/EP2012/061459 dated Sep. 24, 2012.
International Search Report corresponding to International Patent Application No. PCT/EP2013/062310 dated Aug. 2, 2013.
Interview Summary and Corrected Notice of Allowability corresponding to U.S. Appl. No. 11/283,332 dated Jul. 1, 2014.
Interview Summary and Corrected Notice of Allowability corresponding to U.S. Appl. No. 12/072,959 dated Jun. 27, 2014.
Interview Summary correponding to U.S. Appl. No. 11/283,332 dated Dec. 13, 2013.
Jackson (2006) Ubiquitin: a small protein folding paradigm. Org Biomol Chem 4(10):1845-1853.
Khorasanizadeh et al. (1993) Folding and stability of a tryptophan-containing mutant of ubiquitin. Biochemistry 32(27):7054-7063.
Kiel & Serrano (2006) The Ubiquitin Domain Superfold: Structure-based Sequence Alignments and Characterization of Binding Epitopes. Journal of Molecular Biology 355(4):821-844.
Knappik et al. (2000) Fully Synthetic Human Combinatorial Antibody Libraries (HuCAL) Based on Modular Consensus Frameworks and CDRs Randomized with Trinucleotides. Journal of Molecular Biology 296:57-86.
Koide et al. (1998)The Fibronectin Type III Domain as a Scaffold for Novel Binding Proteins. Journal of Molecular Biology 284:1141-1151.
Kolchanov & Shindyalov (1988) Single amino acid substitutions producing instability of globular proteins. Calculation of their frequencies in the entire mutational spectra of the alpha- and beta-subunits of human hemoglobin. Journal of Molecular Evolution 27:154-162.
Krantz et al. (2004) Discerning the Structure and Energy of Multiple Transition States in Protein Folding usinq ψAnalysis. Journal of Molecular Biology 337(2):463-475.
Krippner-Heidenreich et al. (2008) Single-chain TNF, a TNF derivative with enhanced stability and antitumoral activity Journal of Immunology 180:8176-8183.
Ku & Schultz (1995) Alternate protein frameworks for molecular recognition. PNAS 92:6552-6556.
Larsen & Wang. (2002) The Ubiquitin Superfamily: Members, Features, and Phylogenies. Journal of Proteome Research 1:411-419.
Laub et al. (1995) Localized solution structure refinement of an F45W variant of ubiquitin using stochastic boundary molecular dynamics and NMR distance restraints. Protein Science 4:973-982.
Lazar & Wang (1997) H.De novo design of the hydrophobic core of ubiquitin. Protein Science 6:1167-1178.
Lipovsek & Plückthun (2004) In-vitro protein evolution by ribosome display and mRNA display. Journal of Immunoglcal Methods 290:51-67.

(56) References Cited

OTHER PUBLICATIONS

Lo et al. (2009) Structural Basis for Recognition of Diubiquitins by NEMO. Molecular Cell 33:602-615.

Loladze et al. (2005) Both helical propensity and side-chain hydrophobicity at a partially exposed site in alpha-helix contribute to the thermodynamic stability of ubiquitin. Proteins 58(1):1-6.

Lorey et al. (2014) Novel ubiquitin-derived high affinity binding proteins with tumor targeting properties. Journal of Biological Chemistry. 289(12):8493-8507.

Mayr et al. (1994) Domain Interactions and Connecting Peptides in Lens Crystallins. Journal of Molecular Biology 235:84-88.

McConnell & Hoess (1995) Tendamistat as a Scaffold for Conformationally Constrained Phage Peptide Libraries. The Journal of Molecular Biology 250:460-470.

Miura et al. (1999) Characterization of the Binding Interface between Ubiquitin and Class I Human Ubiquitin-conjugating Enzyme 2b by Multidimensional Heteronuclear NMR Spectroscopy in Solution Journal of Molecular Biology 290:213-228.

Müller & Skerra (1994) A.Grafting of a High-Affinity Zn(II)-Binding Site on the β-Barrel of Retional-Binding Protein Results in Enhanced Folding Stability and Enables Simplified Purification. Biochemistry 33(47):14126-14135.

Müller et al. (2001) SUMO, ubiquitin's mysterious cousin. Nat. Rev. Mol. Cell Biol 2:202-210.

Nord et al. (1997) Binding proteins selected from combinatorial libraries of an (-helical bacterial receptor domain. Nature Biotechnology 15:772-777.

Notice of Allowance corresponding to U.S. Appl. No. 10/030,605 dated Apr. 14, 2009.

Notice of Allowance corresponding to U.S. Appl. No. 11/283,332 dated Jun. 6, 2014.

Notice of Allowance corresponding to U.S. Appl. No. 11/656,646 dated Aug. 27, 2013.

Notice of Allowance corresponding to U.S. Appl. No. 11/732,632 dated Aug. 23, 2010.

Notice of Allowance corresponding to U.S. Appl. No. 12/072,959 dated Jun. 3, 2014.

Notice of Allowance corresponding to U.S. Appl. No. 12/514,550 dated Sep. 10, 2013.

Notice of Allowance corresponding to U.S. Appl. No. 13/142,195 dated Aug. 4, 2014.

Notice of Allowance corresponding to U.S. Appl. No. 13/144,809 dated Mar. 3, 2014.

Notice of Allowance corresponding to U.S. Appl. No. 14/126,358 dated Sep. 9, 2016.

Notification Concerning Transmittal of International Preliminary Report on Patentability (Chapter I of the Patent Cooperation Treaty) corresponding to International Patent Application No. PCT/EP2010/069666 dated Jun. 28, 2012.

Notification Concerning Transmittal of International Preliminary Report on Patentability (Chapter I of the Patent Cooperation Treaty) corresponding to International Patent Application No. PCT/EP2010/069674 dated Jun. 28, 2012.

Notification Concerning Transmittal of International Preliminary Report on Patentability (Chapter I of the Patent Cooperation Treaty) corresponding to International Patent Application No. PCT/EP2016/052345 dated Apr. 11, 2016.

Notification of Transmittal of Translation of the International Preliminary Report on Patentability (Chapter I of the Patent Cooperation Treaty) corresponding to International Patent Application No. PCT/EP2004/005730 dated Apr. 13, 2006.

Notification of Transmittal of Translation of the International Preliminary Report on Patentability (Chapter I or Chapter II of the Patent Cooperation Treaty) corresponding to International Patent Application No. PCT/EP2005/010932 dated May 3, 2007.

Nygren & Uhlen (1997) Scaffolds for engineering novel binding sites in proteins. Current Opinion in Structural Biology 7:463-469.

Office Action (Restriction Requirement) corresponding to U.S. Appl. No. 15/549,022 dated May 3, 2018.

Office Action (Restriction Requirement) corresponding to U.S. Appl. No. 15/549,022 dated Nov. 8, 2018.

Office Action corresponding to Australian Patent Application No. 2012268970 dated Aug. 27, 2015.

Office Action corresponding to Canadian Patent Application No. 2,778,871 dated Jan. 30, 2014.

Office Action corresponding to Canadian Patent Application No. 2,837,804 dated May 1, 2015.

Office Action corresponding to Chinese Patent Application No. 2010800569116 dated Jul. 31, 2013. Translation.

Office Action corresponding to European Patent Application No. 00 944 034.8-2401 dated Oct. 7, 2004.

Office action corresponding to European Patent Application No. EP 10 787 815.9-1410 dated Aug. 13, 2013.

Office Action corresponding to Japanese Patent Application No. 2012-504036 dated Aug. 26, 2013.

Office Action corresponding to Japanese Patent Application No. 2012-542583 dated Apr. 22, 2014.

Office Action corresponding to Korean Patent Application No. 10-2011-7018847 dated Jan. 30, 2013. Translation.

Office Action corresponding to Russian Patent Application No. 2012114662/10(022146) dated Dec. 18, 2013.

Office Action corresponding to Russian Patent Application No. 2012114662/10(022146) dated Sep. 8, 2014. (With Translation).

Office Action corresponding to Russian Patent Application No. 2012115491 dated Dec. 24, 2013.

Office Action corresponding to U.S. Appl. No. 10/030,605 dated Apr. 12, 2006.

Office Action corresponding to U.S. Appl. No. 10/030,605 dated Aug. 10, 2005.

Office Action corresponding to U.S. Appl. No. 10/030,605 dated Feb. 15, 2005.

Office Action corresponding to U.S. Appl. No. 10/030,605 dated Feb. 28, 2007.

Office Action corresponding to U.S. Appl. No. 10/030,605 dated Jul. 1, 2008.

Office Action corresponding to U.S. Appl. No. 10/030,605 dated Nov. 16, 2007.

Office Action corresponding to U.S. Appl. No. 10/030,605 dated Sep. 21, 2004.

Office Action corresponding to U.S. Appl. No. 11/283,332 dated Jan. 9, 2008.

Office Action corresponding to U.S. Appl. No. 11/283,332 dated Mar. 3, 2010.

Office Action corresponding to U.S. Appl. No. 11/283,332 dated May 30, 2008.

Office Action corresponding to U.S. Appl. No. 11/283,332 dated Nov. 28, 2008.

Office Action corresponding to U.S. Appl. No. 11/283,332 dated Sep. 3, 2013.

Office Action corresponding to U.S. Appl. No. 11/283,332 dated Sep. 4, 2009.

Office Action corresponding to U.S. Appl. No. 11/656,646 dated May 25, 2010.

Office Action corresponding to U.S. Appl. No. 11/656,646 dated Nov. 13, 2009.

Office Action corresponding to U.S. Appl. No. 11/656,646 dated Sep. 1, 2009.

Office Action corresponding to U.S. Appl. No. 11/732,632 dated Aug. 21, 2009.

Office Action corresponding to U.S. Appl. No. 11/732,632 dated Jun. 3, 2009.

Office Action corresponding to U.S. Appl. No. 11/732,632 dated Mar. 19, 2010.

Office Action corresponding to U.S. Appl. No. 12/072,959 dated Aug. 30, 2013.

Office Action corresponding to U.S. Appl. No. 12/072,959 dated Jan. 27, 2009.

Office Action corresponding to U.S. Appl. No. 12/072,959 dated Jan. 5, 2010.

Office Action corresponding to U.S. Appl. No. 12/072,959 dated Jul. 24, 2008.

(56) References Cited

OTHER PUBLICATIONS

Office Action corresponding to U.S. Appl. No. 12/514,550 dated Aug. 3, 2011.
Office Action corresponding to U.S. Appl. No. 12/514,550 dated Mar. 12, 2012.
Office Action corresponding to U.S. Appl. No. 12/514,550 dated Sep. 15, 2011.
Office Action corresponding to U.S. Appl. No. 13/142,195 dated Feb. 11, 2013.
Office Action corresponding to U.S. Appl. No. 13/142,195 dated Feb. 4, 2014.
Office Action corresponding to U.S. Appl. No. 13/142,195 dated May 29, 2013.
Office Action corresponding to U.S. Appl. No. 13/144,809 dated Oct. 18, 2013.
Office Action corresponding to U.S. Appl. No. 13/516,002 dated Apr. 6, 2015.
Office Action corresponding to U.S. Appl. No. 13/516,002 dated Jan. 26, 2015.
Office Action corresponding to U.S. Appl. No. 14/126,341 dated May 1, 2015.
Office Action corresponding to U.S. Appl. No. 14/126,341 dated Sep. 29, 2015.
Office Action corresponding to U.S. Appl. No. 14/126,358 dated Apr. 16, 2016.
Office Action corresponding to U.S. Appl. No. 14/407,213 dated May 25, 2016.
Office Action corresponding to U.S. Appl. No. 15/744,054 dated Mar. 14, 2019.
Office Action Restriction Requirement corresponding to U.S. Appl. No. 14/126,358 dated Oct. 28, 2015.
Office Action Restriction Requirement corresponding to U.S. Appl. No. 14/407,213 dated Jan. 21, 2016.
Office Action Restriction Requirement corresponding to U.S. Appl. No. 15/548,976 dated Jun. 14, 2019.
Office Action corresponding to U.S. Appl. No. 15/744,054 dated Jul. 30, 2019.
Ohashi et al. (2007) Efficient protein selection based on ribosome display system with purified components. Biochemical and Biophysical Research Communications 352:270-276.
Pack & Pluckthun (1992) A.Miniantibodies: Use of Amphipathic Helices to Produce Functional, Flexibly Linked Dimeric Fv Fragments with High Avidity in *Escherichia coli*. Biochemsitry 31(6):1579-1584.
Raasi Shahri et al. (2004) Binding of polyubiquitin chains to ubiquitin-associated (UBA) domains of HHR23A J. Mol. Biol. 34:1367-1379.
Rahighi et al. (2009) Specific Recognition of Linear Ubiquitin Chains by NEMO Is Important for NF-κB Activation. Cell 136:1098-1109.
Search Report corresponding to Chinese Patent Application No. 201080056911.6 dated Jun. 14, 2013. Translation.
Skerra (2000) Engineered protein scaffolds for molecular recognition. Journal of Molecular Recognition 13(4):167-187.
Skerra et al. (2007) Alternative non-antibody scaffolds for molecular recognition. Current Opinion in Biotechnology 18(4):295-304.
Smith et al. (1998) Small Binding Proteins Selected from a Conbinatorial Repertoire of Knottins Displayed on Phage Journal of Molecular Biology 277(2):317-332.
Ubiquitin-like Superfamily (2004) pp. 1-4.
Weidle et al. (2013) The Emerging Role of New Protein Scaffold-based Agents for Treament of Cancer. Caner Genomics & Proteomics 10(4):155-168.
Wells & Lowmann (1992).Rapid evolution of peptide and protein binding properties in vitro. Current Opinion in Biotechnology 3:355-362.
Wells (1990) Additivity of Mutational Effects in Proteins. Biochemistry 29(37):8509-8517.
Zahnd et al. (2007) Ribosome display: selecting and evolving proteins in vitro that specifically bind to a target Nature Methods 4(3):269-279.
Zhang et al. (1997) Directed evolution of a fucosidase from a galactosidase by DNA shuffling and screening. PNAS 94:4504-4509.
Extended European Search Report corresponding to European Patent Application No. 18213661 .4-1111 dated May 31, 2019.
International Preliminary Report on Patentability corresponding to International Patent Application No. PCT/EP2020/052438 dated Jul. 27, 2021.
International Search Report corresponding to International Patent Application No. PCT/EP2019/085596 dated Feb. 6, 2020.
International Search Report corresponding to International Patent Application No. PCT/EP2020/052438 dated Mar. 19, 2020.
Notice of Allowance corresponding to U.S. Appl. No. 15/548,976 dated Jul. 22, 2020.
Notice of Allowance corresponding to U.S. Appl. No. 15/744,054 dated Jan. 9, 2020.
Notice of Allowance corresponding to U.S. Appl. No. 15/744,147 dated Aug. 17, 2020.
Notice of Allowance corresponding to U.S. Appl. No. 16/324,651 dated Apr. 6, 2022.
Notice of Allowance corresponding to U.S. Appl. No. 16/324,651 dated Oct. 26, 2021.
Office Action (Restriction Requirement) corresponding to U.S. Appl. No. 16/324,551 dated Feb. 4, 2021.
Office Action (Restriction Requirement) corresponding to U.S. Appl. No. 16/761,677 dated Nov. 6, 2021.
Office Action corresponding to U.S. Appl. No. 15/744,147 dated Apr. 1, 2020.
Office Action corresponding to U.S. Appl. No. 16/324,651 dated Jun. 4. 2021.
Office Action corresponding to U.S. Appl. No. 16/376,847 dated Feb. 24, 2021.
Office Action corresponding to U.S. Appl. No. 15/548,976 dated Mar. 17, 2020.
Written Opinion corresponding to International Application No. PCT/EP2019/085596 dated Jun. 25, 2020.
Written Opinion corresponding to International Application No. PCT/EP2020/052438 dated Aug. 6, 2020.

\* cited by examiner

FIG. 2A SEC profile of 146414
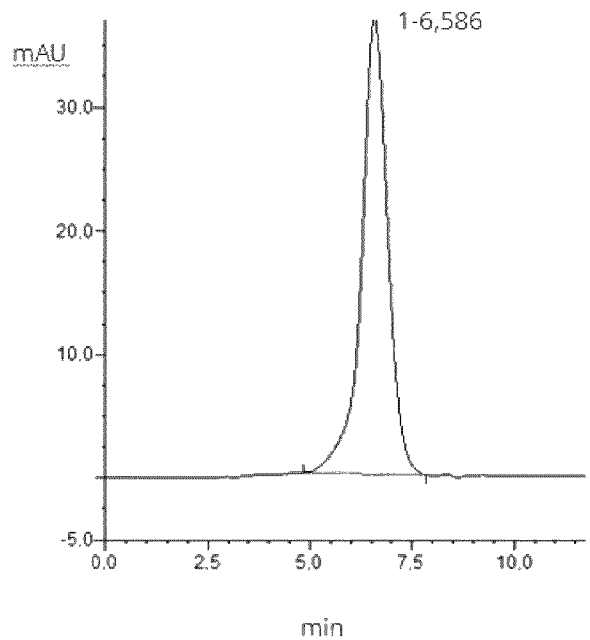
FIG. 2B. SEC profile of 143276
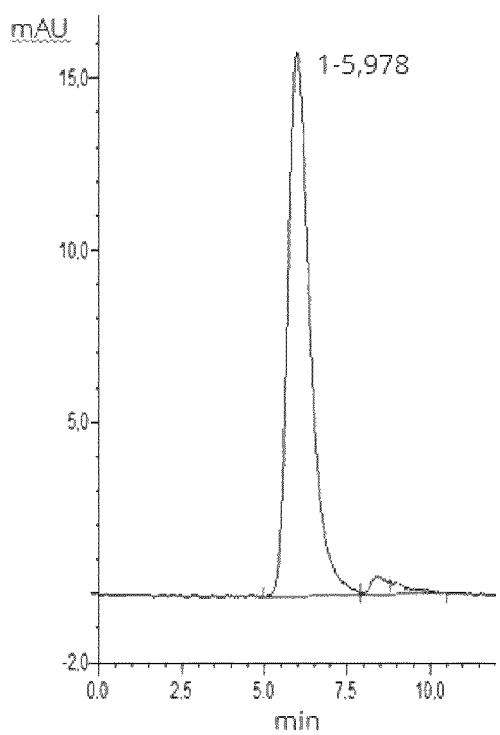

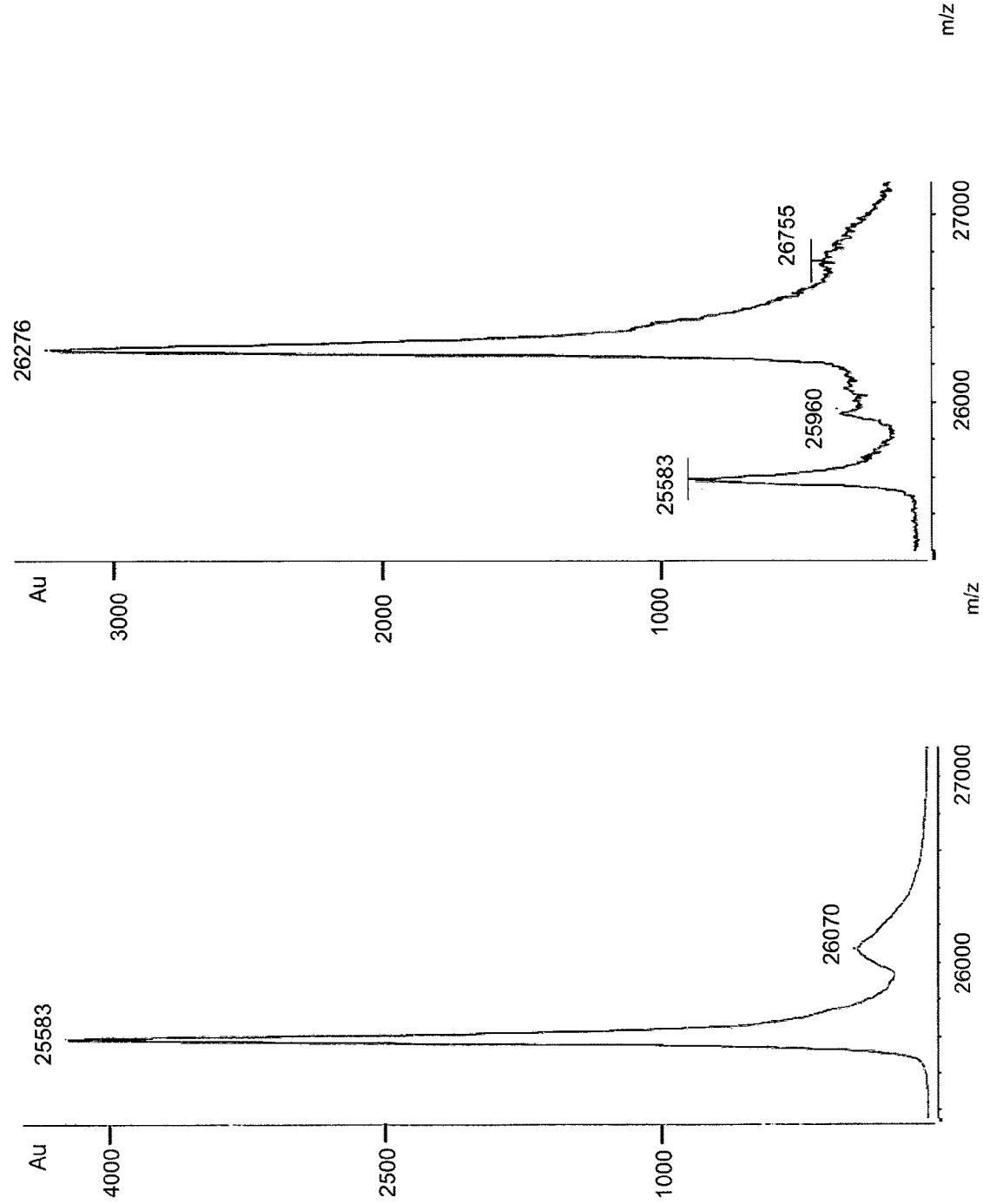
FIG. 4A. 146414 and labeled 146414

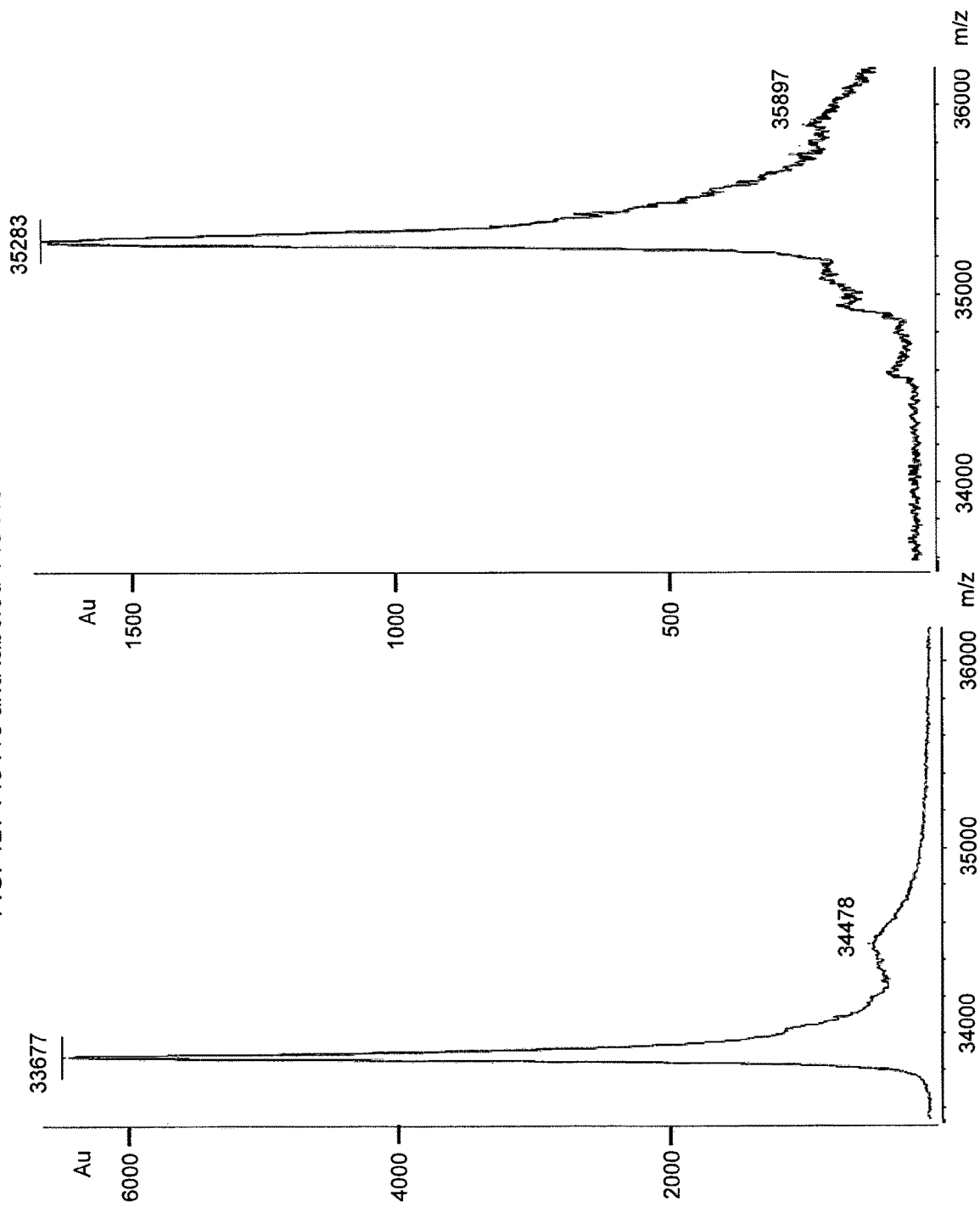

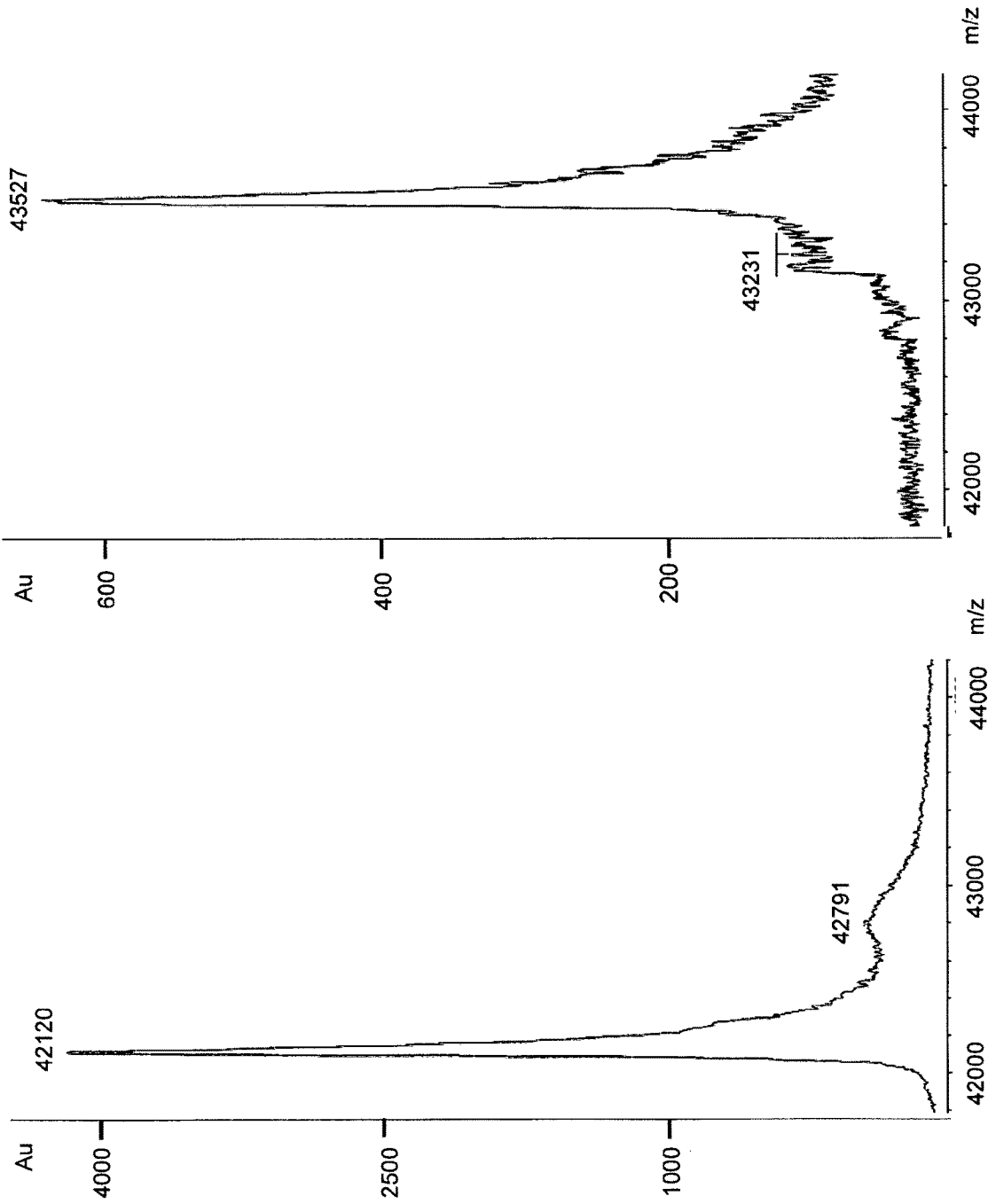
FIG. 4C. 146418 and labeled 146418

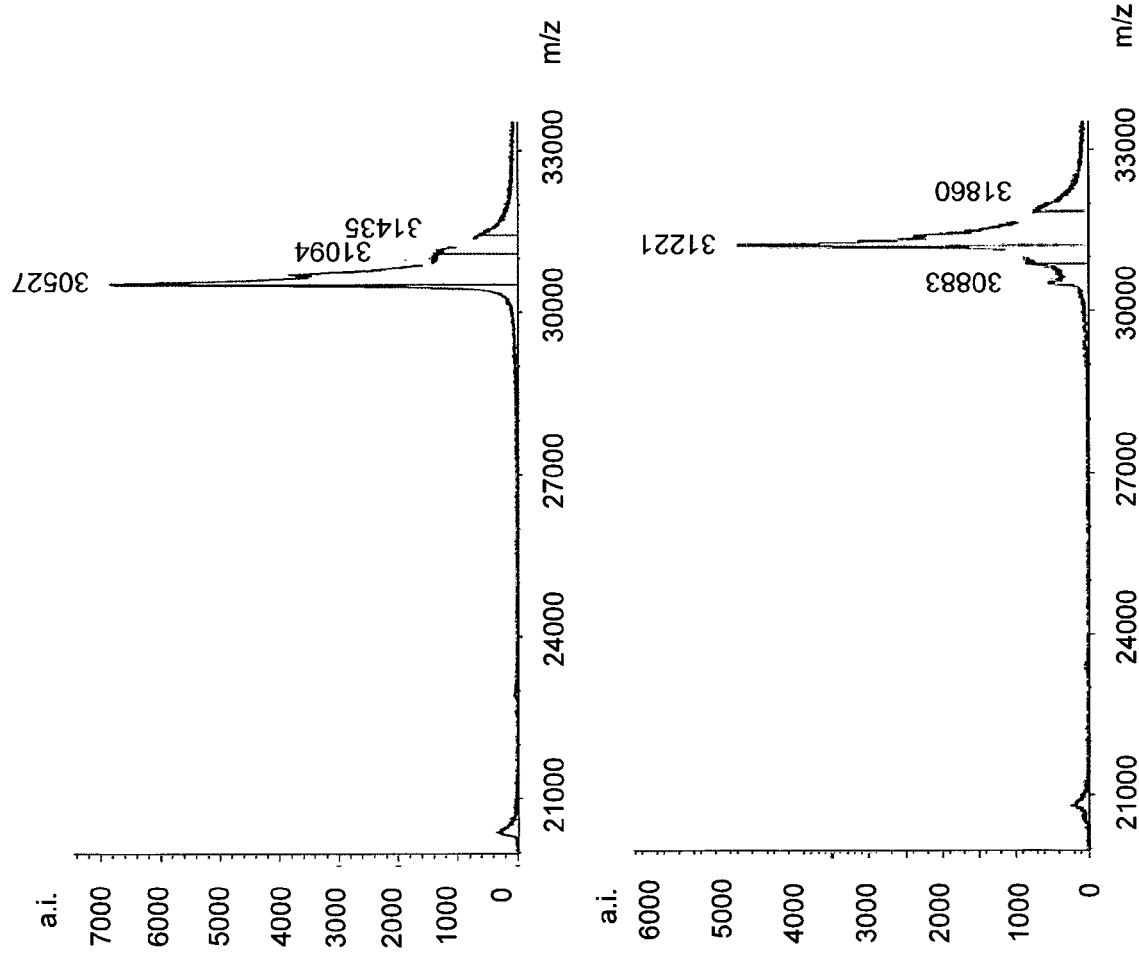

FIG 4E. 140353
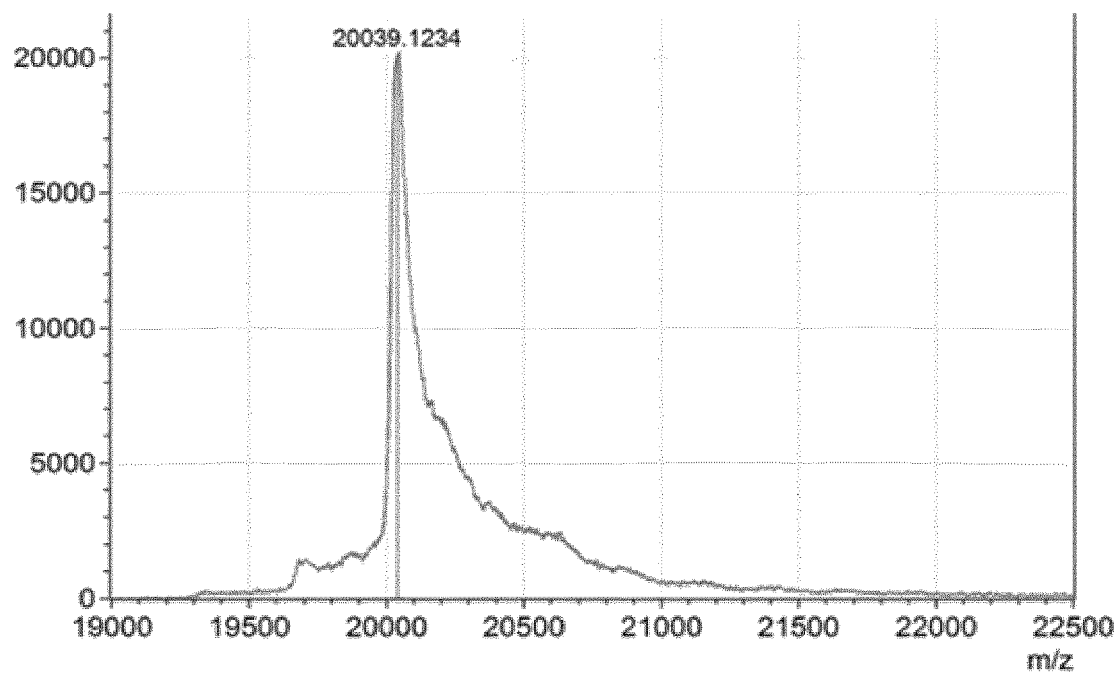
FIG 4F. 140350
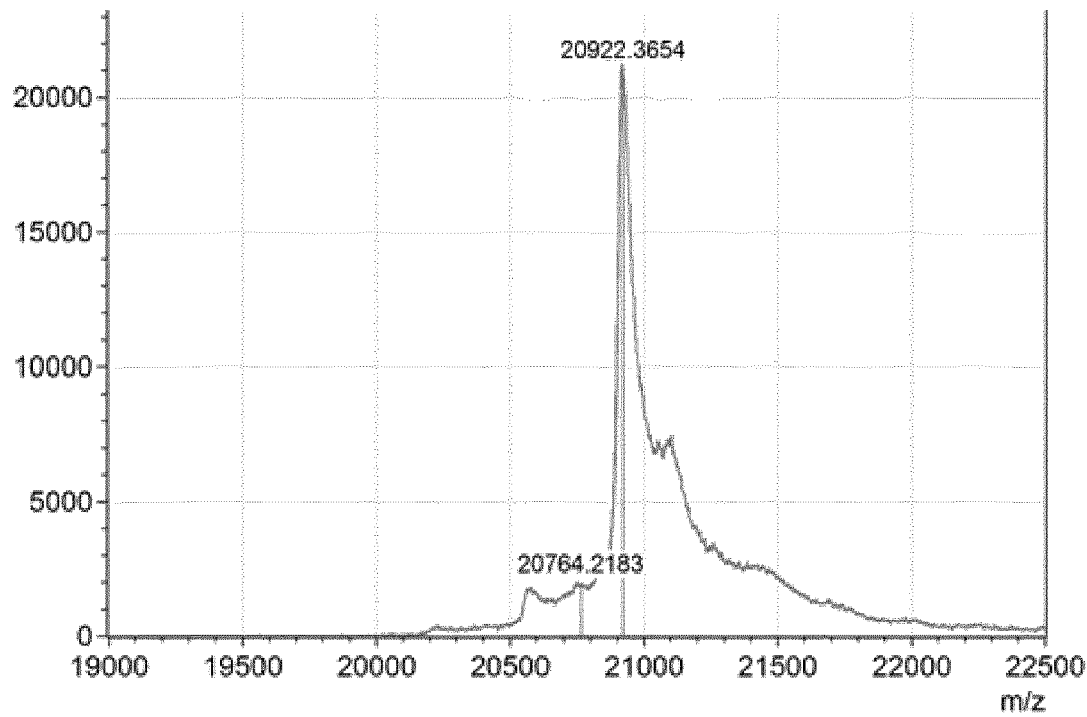

TARGETED COMPOUNDS FOR THE SITE-SPECIFIC COUPLING OF CHEMICAL MOIETIES COMPRISING A PEPTIDE LINKER

REFERENCE TO SEQUENCE LISTING XML

The Sequence Listing XML associated with the instant disclosure was electronically submitted to the United States Patent and Trademark Office Via EFS as a 58,134 byte UTF-8-encoded text file created on Nov. 2, 2018 and entitled "3073_12_PCT_US_ST25.txt". The Sequence Listing as originally filed was replaced on Feb. 9, 2022 with a 59,643 byte UTF-8-encoded text file created on Nov. 2, 2018 and entitled "Substitute_Sequence_Listing_3073_12_PCT_US_ST25.txt", which was then replaced on Dec. 12, 2022 with a 59,821, byte UTF-8-encoded text file created on Dec. 2, 2018 and entitled "December_2022_Substitute_Sequence_Listing_3073_12_PCT_US_ST25.txt". The Substitute Sequence Listing filed on Dec. 12, 2022 was then replaced on Jul. 11, 2023 with a Third Substitute Sequence Listing, which is a 59,822 byte UTF-8-encoded text file created on Jul. 11, 2023 and entitled "July_2023_Substitute_Sequence_ Listing_3073_12_PCT_US_ST25.txt" Each Sequence Listing submitted Via Patent Center is hereby incorporated by reference in its entirety.

FIELD OF THE INVENTION

The invention relates to targeted compounds with the ability of site-specific coupling of chemical moieties due to a defined number of coupling sites at defined positions embedded in specific amino acids without secondary or tertiary structures. The targeted compound comprises at least one targeting domain selected from a non-Immunoglobulin protein or an antibody fragment capable of binding a target. The targeted compound further comprises at least one linking moiety consisting of up to 80 amino acids, preferably alanine, proline, and serine. The targeted compound further comprises at least one coupling site consisting of one cysteine or of a cysteine-rich peptide motif. Said linking moiety connects the targeting domain and a coupling site and/or said linking moiety connects two coupling sites. The invention specifically features fusion proteins with ubiquitin muteins (AFFILIN®) as non-Ig targeting domain. The invention also relates to the use of the targeted compounds for medical applications, in treatment or diagnosis of diseases.

BACKGROUND OF THE INVENTION

Antibody-drug conjugates (ADC) selectively target drugs to a desired location and are composed of a monoclonal antibody and a cytotoxic agent (toxin). The antibody is targeting the agent to a specific target on a surface of a cell and binds the conjugate to the cell, where the drug can destroy the cell. An unsolved problem of ADCs is the coupling of a chemical moiety since antibodies do not possess defined free cysteines which allow site-specific coupling of e.g. a toxin. Instead, coupling of agents to antibodies is often performed via lysine residues which results in a product which is inhomogeneous in terms of positions where the toxin is coupled as well as the number of toxins coupled to the conjugates. Another established procedure of conjugation of drugs to monoclonal antibodies utilizes reduction of disulfide-bridges between cysteine residues present in antibodies to conjugate a drug to the free thiol groups of the reduced cysteine residues. However, such conjugates may be structurally unstable, which is a major disadvantage for further therapeutic or diagnostic applications as well as for manufacturing.

Due to several limitations of antibody-chemical moiety conjugates, there is an urgent need to provide novel compounds with improved properties overcoming the described disadvantages.

Accordingly, there is a need in the field to provide novel compounds with coupling sites which allow specific coupling of a defined number of chemical moieties to targeted compounds to result in homogenous targeted products. Thus, it is an objective of the present invention to provide novel targeted carrier proteins with a defined number and defined location of coupling sites while maintaining the structural and functional characteristics of the targeting domain.

The invention provides compounds comprising targeting moieties based on non-Ig proteins or antibody fragments and a defined number of coupling sites at defined positions embedded in specific amino acids without secondary or tertiary structures. Such compounds are particularly well-suited for medical applications overcoming the disadvantages described above.

The above overview does not necessarily describe all problems solved by the present invention.

SUMMARY OF THE INVENTION

The present invention relates to a targeted compound for the coupling of chemical moieties comprising at least one targeting domain capable of binding a target with a binding constant $K_D$ of 500 nM or less, and at least one linking moiety consisting of up to about 80 amino acids wherein the linking moiety is comprising or consisting essentially of alanine, proline, and serine, and at least one coupling site at the C-terminal or N-terminal end of a linking moiety wherein the coupling site is consisting of one cysteine or of a cysteine-rich peptide motif CXC, CXXC (SEQ ID NO: 35), or CXXXC (SEQ ID NO: 81), wherein X is selected from non-aromatic amino acids, and wherein a linking moiety connects a targeting domain and a coupling site and/or wherein a linking moiety connects two coupling sites. Preferably, the linking moiety is consisting essentially of or consisting of 20% to 60% alanine residues, 20% to 40% proline residues, and 10% to 60% serine residues. Optionally, the targeted compound comprises additionally an amino acid sequence of up to 80 amino acids ("cap") after the most terminally located coupling site or after the most terminally located targeting domain. Preferably, the targeted compound is comprising $T_m L_n S_o$ wherein m is 1, 2, 3, 4, 5 and n is 1, 2, 3, 4, 5, 6, 7, 8, 9, 10, 11, 12, 13, 14, 15, 16, 17, 18, 19, or 20 and o=n or o=n−1 and, optionally $T_m L_n S_o$cap. Thus, the targeted compound comprises at least one targeting domain and 1 to 20 linking moieties and coupling sites.

The present invention further relates to a targeted compound wherein the X in the coupling site is selected from non-aromatic and non-hydrophobic amino acids, preferably selected from small or hydrophilic amino acids such as proline, alanine, serine, valine, glycine, threonine, asparagine, aspartic acid, glutamine, glutamic acid, lysine, histidine, or arginine.

The present invention also relates to a targeted compound wherein the targeting domain is a non-Immunoglobulin protein, preferably selected from but not limited to ubiquitin muteins (AFFILIN®), muteins of domains of staphylococcal protein A, ankyrin repeat protein muteins, lipocalin muteins, muteins of human Fyn SH3 domain, muteins of the tenth domain of human fibronectin, muteins of Kunitz domains of various protease inhibitors, Sac7d muteins, chagasin muteins, or muteins of multimerized Low Density Lipoprotein Receptor-A, muteins of FN3 domain, muteins of cysteine-knot miniprotein muteins, muteins of Armadillo-repeat protein, muteins of tetranectin, muteins of C-type lectin domain, or muteins of CTLA4, or an antibody fragment or antibody derivative. Preferably, the targeting domain of the targeted compound is a non-Immunoglobulin protein, more preferably a mutein exhibiting 80% to 94% identity to the parental protein, even more preferably a ubiquitin mutein (AFFILIN®) exhibiting 80% to 94% identity to ubiquitin (SEQ ID NO: 1) or 80% to 94% identity to bis-ubiquitin (SEQ ID NO: 2).

Further, the present invention relates to a targeted compound wherein the targeted compound is a fusion protein or wherein the targeted compound comprises a covalent linkage between targeting domain and the first linking moiety.

The present invention relates to a targeted compound wherein a biologically active moiety is chemically coupled to the coupling site. The biologically active moiety may be selected from chemical moieties such as drugs, toxins, small molecules, chelators, and dyes.

The present invention relates to the use of the targeted compound in diagnostic or therapeutic applications, preferably in vitro diagnostic or therapeutic applications.

The present invention relates to a composition comprising the targeted compound as described herein and to a kit comprising said composition.

The present invention is directed to a method for the preparation of a targeted compound. This summary of the invention does not necessarily describe all features of the present invention. Other embodiments will become apparent from a review of the ensuing detailed description.

BRIEF DESCRIPTION OF THE FIGURES

FIG. 4. MALDI-TOF analysis to confirm homogeneously labeling of fusion proteins. MALDI-TOF mass spectra of fusion protein and EDANS-C2-Maleimid labeled fusion protein, FIG. 4A Fusion protein 146414 (left side of the figure) and EDANS-labeled fusion protein 146414 (right side of the figure). FIG. 4B. Fusion protein 146416 (left side of the figure) and EDANS-labeled fusion protein 146416 (right side of the figure). FIG. 4C. Fusion protein 146418 (left side of the figure) and EDANS-labeled fusion protein 146418 (upper part of the figure), FIG. 4D. Fusion protein 143276 (lower part of the figure) and EDANS-labeled fusion protein 143276. FIG. 4E. Fusion protein 140343 with peptide motif "CPAC" as coupling site (6 coupling sites) FIG. 4F. Fusion protein 140350 with peptide motif "CPAC" as coupling site (6 coupling sites).

DETAILED DESCRIPTION OF THE INVENTION

Figure 1:
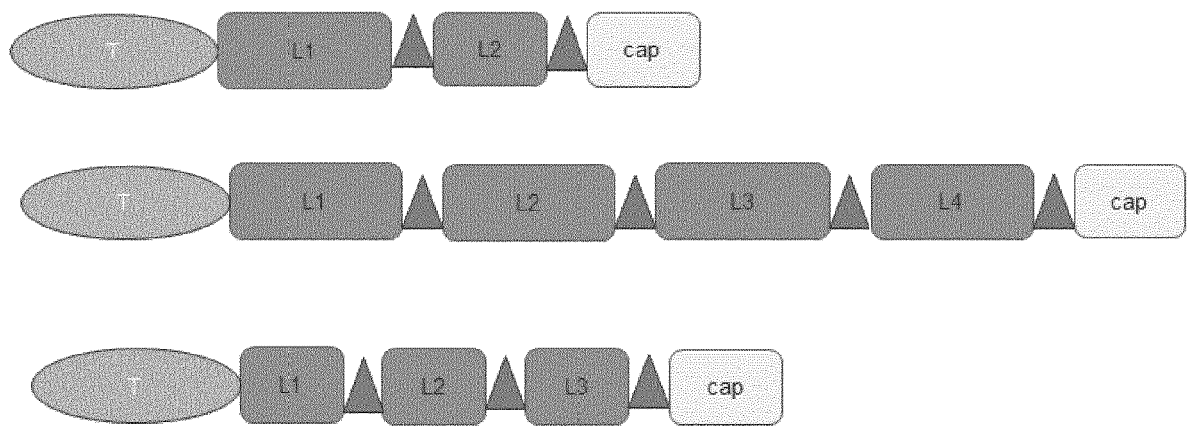
FIG. 1. Schematic drawing of selected targeted compounds of the invention. Shown are examples for compounds, i.e. fusion proteins, with a targeting domain that is not an antibody (shown in light grey as ellipse and referred to as T), 2 to 4 linking moieties consisting of amino acids Ala, Pro, and Ser (shown in medium grey as rectangle and referred to as L1, L2, L3, or L4) connecting 2 to 4 coupling sites consisting of Cys or a Cys-rich peptide motif (shown in dark grey as triangle for site-specific coupling), and an amino acid region of 10 to 80 amino acids after the most terminally located coupling site (shown as rectangle; referred to as "cap").
Figure 2C:
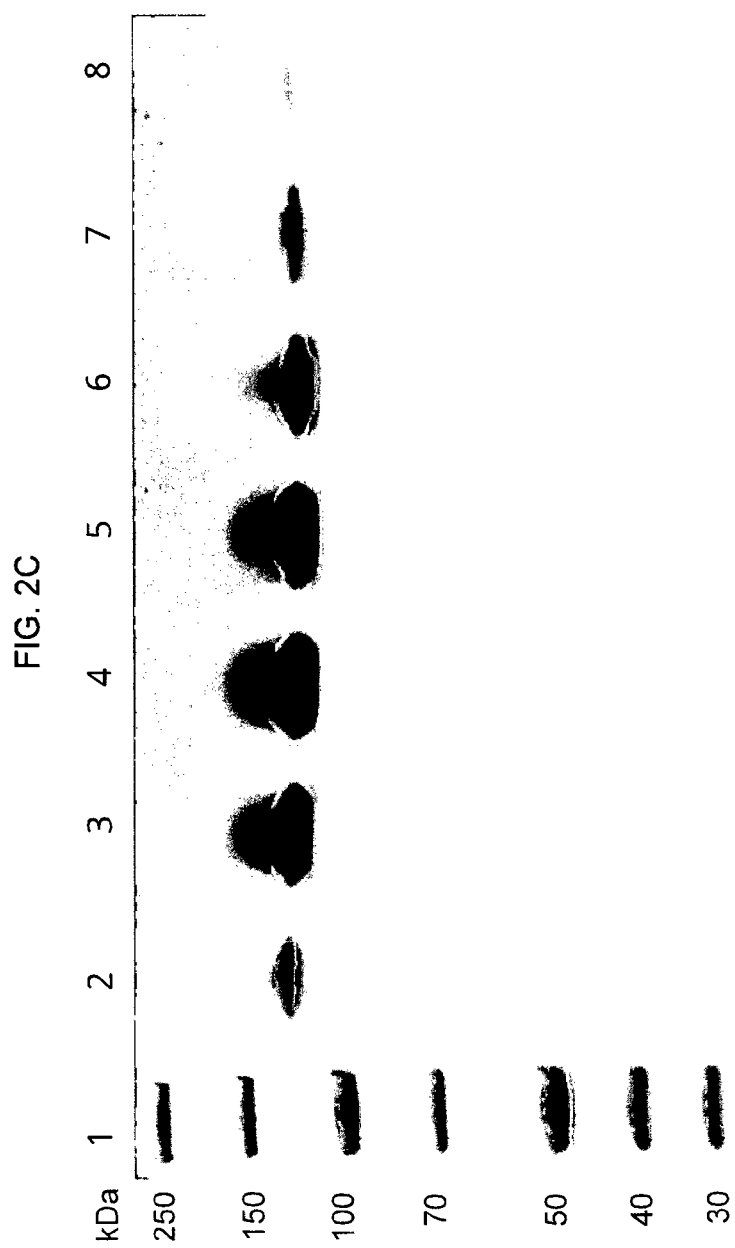
FIG. 2C. SDS-PAGE analysis of SEC fractions of fusion protein 146414. Lane 1: molecular weight marker, lanes 2 to 7: fractions FIG. 2D. SDS-PAGE analysis of SEC fractions of fusion protein 140353 (coupling site: CXXC; SEQ ID NO: 35). Lane 1: molecular weight marker, lane 2: supernatant, lane 3: pellet, lane 4: flow through, lanes 5 to 10: fractions.
Figure 2D:
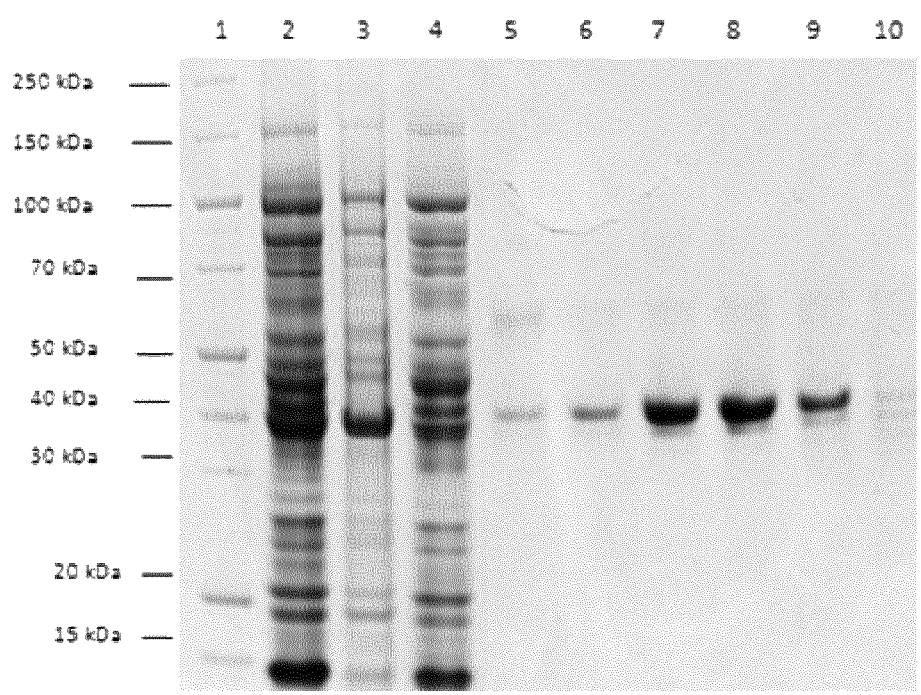
FIG. 2. Expression and purification of fusion proteins.
FIG. 2A. SEC profile of fusion protein 146414.
FIG. 2B. SEC profile of fusion protein 143276.
Figure 3A:
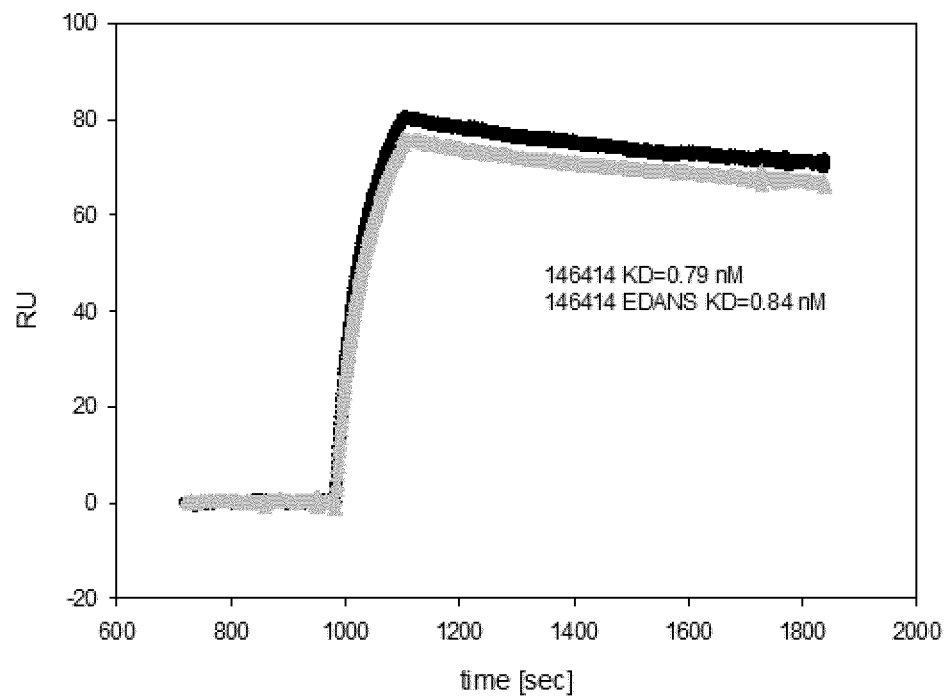
FIG. 3A. Fusion protein 146414 and labeled 146414 (2 coupling sites).
Figure 3B:
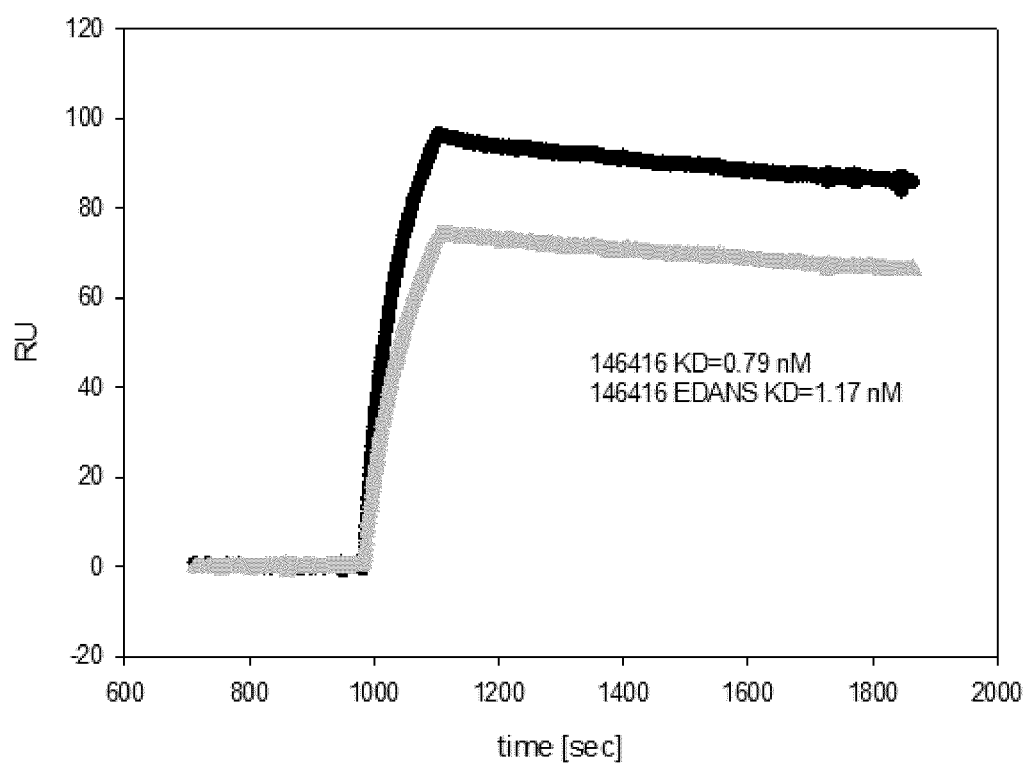
FIG. 3B. Fusion protein 146416 and labeled 146416 (4 coupling sites), FIG. 3C. Fusion protein 146418 and labeled 146418 (4 coupling sites)
Figure 3C:
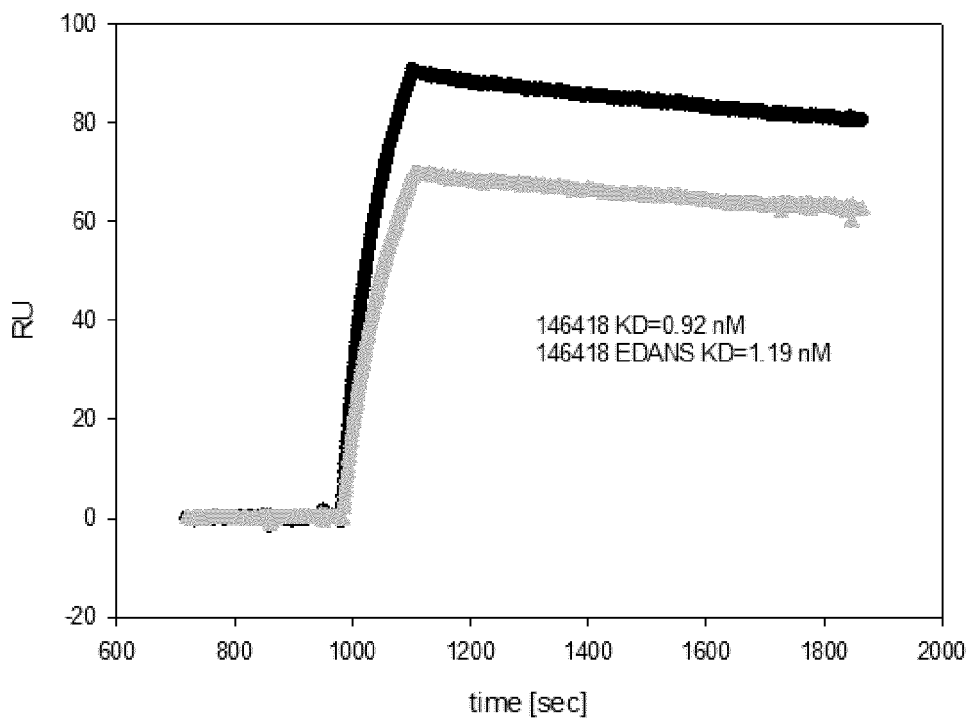
FIG. 3. SPR analysis of fusion proteins and EDANS labeled fusion proteins to confirm specific binding affinity of labeled fusion proteins to the target. Black line represents the unmodified fusion protein, the grey line the EDANS-labeled fusion protein.
FIG. 3D shows binding kinetics of fusion protein 143276 to EGFR (2 coupling sites); different concentrations of fusion protein 143276 were analyzed (0, 1.9, 3.9, 7.8, 15.6, 31.3, 62.5, 125, 250, 500 nM).
Figure 3D:
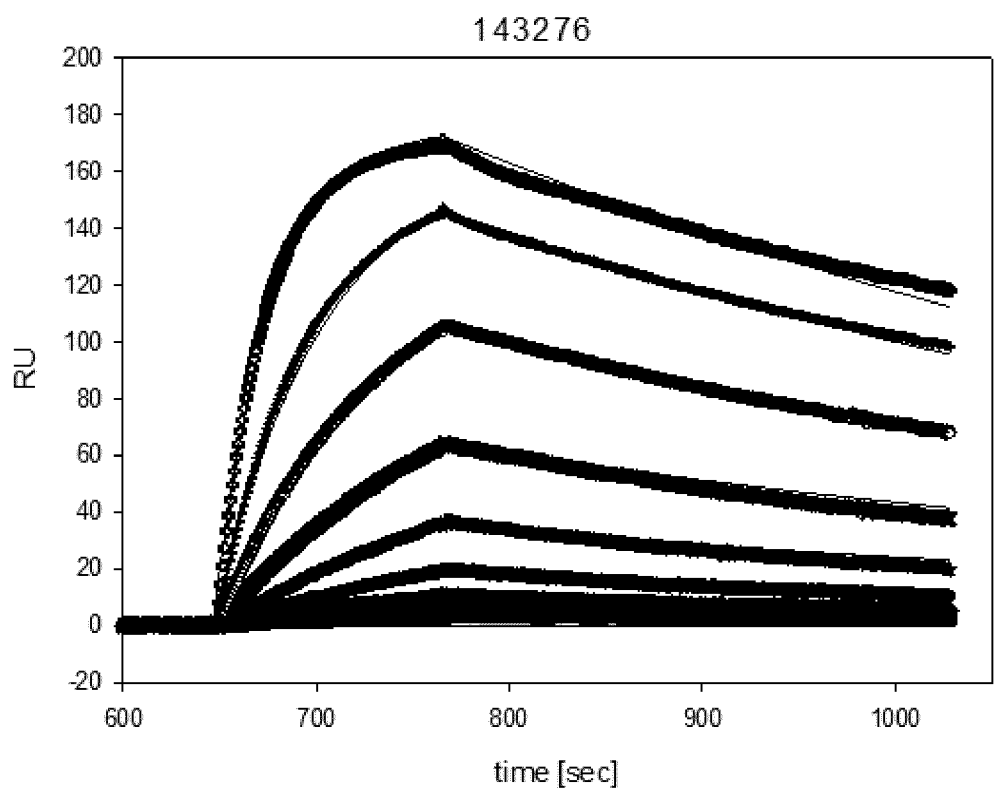

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs. Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, is a part of this specification.

Definitions

The term "about", as used herein, encompasses the explicitly recited amounts as well as deviations therefrom of up to ±20%. More preferably, a deviation of up to ±15%, more preferably of up to ±10%, and most preferably up to 5% is encompassed by the term "about". The term "at least about 10, 20, 30, 40, 50, 60, 70, 80 amino acid residues" is not limited to the concise number of amino acid residues but also comprises amino acid stretches that comprise up to 20% additional or comprise up to 20% less residues. For example "about 70 amino acid residues" may also comprise 56 to 84 amino acid residues without deferring from the present invention.

As used herein, a "compound" refers to a composition of matter comprising at least two components, wherein these at least two components are held together by any kind of interaction, for example by covalent bonds, by ionic bonds, by hydrogen bonds, by van der Waals interactions, or by hydrophobic interactions.

The terms "component" or "moiety" or "domain" or "site" are used herein interchangeably and refer to substructures which are part of a compound.

As will be explained below in greater detail, the "targeted compound" of the invention comprises at least three components, namely (i) at least one targeting domain and (ii) at least one linking moiety and (iii) at least one coupling site, each counted as one component. As used herein, a "targeted compound" thus refers to a composition of matter comprising at least three components. A compound of the invention can be a fusion protein or a conjugate.

The terms "protein" and "polypeptide" refer to any chain of two or more amino acids linked by peptide bonds, and do not refer to a specific length of the product. Thus, "peptides", "protein", "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modification by non-naturally occurring amino acids and similar modifications which are well known in the art. Thus, fusion proteins comprising two or more protein moieties also fall under the definition of the term "protein" or "polypeptides".

The term "fusion protein" relates to a protein comprising at least a first amino acid chain joined genetically to at least a second amino acid chain. Thus, a fusion protein may comprise a multimer of proteins/peptides which are expressed as a single, linear polypeptide. It may comprise one, two, three, four, or even more proteins/peptides. For example, a fusion protein can be created through joining of two or more genes that originally coded for separate proteins/peptides.

The term "fused" means that the components are linked by peptide bonds, either directly or via peptide linkers.

The term "conjugate" as used herein relates to a protein comprising or essentially consisting of at least a first protein attached chemically to other substances such as to a second protein or a non-proteinaceous moiety. The conjugation can be performed by means of organic synthesis or by use of enzymes including natural processes of enzymatic post-translational modifications. Examples for protein conjugates are glycoproteins (conjugated protein with carbohydrate component) or lipoproteins (conjugated protein with lipid component). The molecule can be attached for example at one or several sites through any form of a linker. Chemical coupling can be performed by chemistry well known to someone skilled in the art, including substitution (e.g. N-succinimidyl chemistry), addition or cycloaddition (e.g. maleimide chemistry or click chemistry) or oxidation chemistry (e.g. disulfide formation). Some examples of non-proteinaceous polymer molecules which may be chemically attached to a compound of the invention are hydroxyethyl starch, polyethylene glycol, polypropylene glycol, dendritic polymers, polyoxyalkylene, chelators, drugs, toxins, small molecules, dyes, and others.

A fusion protein or protein conjugate may further comprise one or more reactive groups or peptidic or non-peptidic components such as ligands or therapeutically or diagnostically relevant molecules such as radionuclides or toxins. It may also comprise small organic or non-amino acid based substances, e.g. a sugar, oligo- or polysaccharide, fatty acid, etc. Methods for attaching a protein of interest to such non-proteinaceous components are well known in the art, and are thus not described in further detail here.

Throughout this specification, the term "non-immunoglobulin protein" is often abbreviated as "non-Ig protein". Occasionally, both the long form and the abbreviated form are used at the same time, e.g. in the expression "non-immunoglobulin (Ig) protein".

The term "naturally occurring" as used herein, as applied to an object refers to the fact that an object can be found in nature. For example, a polypeptide or polynucleotide sequence that is present in an organism that can be isolated from a source in nature and which has not been intentionally modified by man in the laboratory is naturally occurring.

In contrast thereto, the terms "non-natural" or "artificial" as used herein interchangeably refer to an object that is not naturally occurring, i.e., the term refers to an object that has been created, produced, or modified by man. For example, a polypeptide or polynucleotide sequence that has been intentionally modified or generated by man in a laboratory is "non-natural". For example, the non-Ig protein of the invention is an artificial protein not existing in nature.

The term "binding" according to the invention preferably relates to a specific binding.

The term "dissociation constant" or "$K_D$" defines the specific binding affinity. As used herein, the term "$K_D$" (usually measured in "mol/L", sometimes abbreviated as "M") is intended to refer to the dissociation equilibrium constant of the particular interaction between a first compound and a second compound. In the context of the present invention, the term $K_D$ is particularly used to describe the binding affinity between a binding protein and a target protein (or targeting domain).

As used herein, the terms "bind specifically", "specifically bind", and "specific binding" are understood to mean that the targeting domain of the targeted compound of the invention has a selective binding affinity for a particular target with a dissociation constant $K_D$ of 1 µM ($10^{-6}$ M) or less, preferably 100 nM ($10^{-7}$ M) or less, preferably 10 nM ($10^{-8}$ M) or less, preferably 1 nM ($10^{-9}$ M) or less, preferably 100 µM ($10^{-10}$ M), or preferably 10 µM ($10^{-11}$ M) or less. A high affinity corresponds to a low value of $K_D$. "Specific binding" means herein that a protein binds stronger to a target for which it is specific, compared to the binding to another molecule. Preferably, the dissociation constant ($K_D$) for the target to which the compound binds specifically is more than 10-fold, preferably more than 20-fold, more preferably more than 50-fold, even more preferably more than 100-fold, 200-fold, 500-fold, or 1000-fold lower than the dissociation constant for the target to which the binding protein does not bind specifically.

Appropriate controls as known to someone skilled in the art can be used to distinguish between "specific" and "non-specific" binding.

The terms "protein capable of binding" or "binding protein" or "targeting domain" refer to an amino acid sequence (protein) capable of binding to a target protein (e.g. a tumor specific protein; a protein expressed on the surface of a tumor cell or a circulating tumor cell or a matrix protein or others). Any such binding protein may comprise additional components such as, for example, multimerization moieties, polypeptide tags, polypeptide linkers and/or non-proteinaceous polymer molecules.

The term "AFFILIN®" (registered trademark of Navigo Proteins GmbH, formerly known as Scil Proteins GmbH) as used herein refers to non-immunoglobulin derived binding proteins based on ubiquitin muteins. The terms "AFFILIN®" and "ubiquitin mutein" and "modified ubiquitin" are all used synonymously and can be exchanged. The terms as used herein refer to derivatives of ubiquitin which differ from unmodified ubiquitin (for example, SEQ ID NO: 1) or bis-ubiquitin (for example, SEQ ID NO: 2) by amino acid exchanges, insertions, deletions, or any combination thereof, provided that the AFFILIN® has a specific binding affinity to a target which is at least 10-fold lower or absent in unmodified ubiquitin or bis-ubiquitin. This functional property of an AFFILIN® is a de novo created property. An AFFILIN® is not a naturally occurring ubiquitin existing in or isolated from nature. An AFFILIN® molecule according to this invention comprises or consists of at least one modified ubiquitin moiety or two modified ubiquitin moieties linked together in a head-to-tail fusion. A "head-to-tail fusion" is to be understood as fusing two ubiquitins together by connecting them in the direction (head) N—C—N—C— (tail), as described for example in EP2379581B1 which is incorporated herein by reference. Ubiquitin moieties may be connected directly without any linker or with peptide linkers.

The terms "ubiquitin" or "unmodified ubiquitin" refer to ubiquitin in accordance with SEQ ID NO: 1 (wild type ubiquitin) or to proteins with at least 95% amino acids identity to SEQ ID NO: 1 (for example, with point mutations F45W, G75A, G76A which do not influence binding to a target). Particularly preferred are ubiquitins from mammals, e.g., humans, primates, pigs, and rodents. On the other hand, it should be noted that the ubiquitin origin is not of high importance since according to the art all eukaryotic ubiquitins are highly conserved and the mammalian ubiquitins examined up to now are even identical with respect to their amino acid sequence. In this sense, ubiquitin from any other eukaryotic source can be used for further modifications to generate a novel binding capability. For instance ubiquitin of yeast differs only in three amino acids from the wild-type human ubiquitin (SEQ ID NO: 1).

The term "bis-ubiquitin" refers to a linear protein wherein two ubiquitin moieties are directly fused to each other in head to tail orientation. The term "bis-ubiquitin" refers to SEQ ID NO: 2 or to proteins with at least 95% amino acids identity to SEQ ID NO: 2 (for example, with point mutations selected from F45W, G75A, G76A, F121W, G151A, G152A).

As used herein, "substitutions" are defined as exchanges of an amino acid by another amino acid. Given the known genetic code, and recombinant and synthetic DNA techniques, the skilled scientist can readily construct DNAs encoding the amino acid variants. The term "insertions" comprises the addition of amino acids to the original amino acid sequence wherein the original amino acid remains stable without significant structural change. The term "deletion" means that one or more amino acids are taken out of the original sequence and the amino acids originally N-terminal and C-terminal of the deleted amino acid are now directly connected and form a continuous amino acid sequence.

The term "amino acid sequence identity" refers to a quantitative comparison of the identity (or differences) of the amino acid sequences of two or more proteins. "Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity. To determine the sequence identity, the sequence of a query protein is aligned to the sequence of a reference protein. Methods for alignment are well known in the art. For example, the SIM Local similarity program is preferably employed (Xiaoquin Huang and Webb Miller (1991), Advances in Applied Mathematics, vol. 12: 337-357), that is freely available (see also the SIM resource, a part of the Expasy website operated by the SIB Swiss Institute for Bioinformatics). For multiple alignment analysis ClustalW is preferably used (Thompson et al. (1994) Nucleic Acids Res., 22(22): 4673-4680).

Each amino acid of the query sequence that differs from the reference amino acid sequence at a given position is counted as one difference. An insertion or deletion in the query sequence is also counted as one difference. For example, an insertion of a linker between two ubiquitin moieties is counted as one difference compared to the reference sequence.

The sum of differences is then related to the length of the reference sequence to yield a percentage of non-identity. The quantitative percentage of identity is calculated as 100 minus the percentage of non-identity. In specific cases of determining the identity of ubiquitin muteins aligned against unmodified ubiquitin, differences in positions 45, 75 and/or 76 are not counted, in particular, because they are not relevant for the novel binding capability of the ubiquitin mutein but are only modifications relevant for certain experimental settings.

As used herein, the term "linker" or "linking moiety" refers to a moiety that connects a functional component with at least a second functional component. For example, a linker of the invention connects two coupling sites or a targeting domain and a coupling site. Other linkers may connect two targeting domains. Preferred embodiments of this invention comprise peptide linkers. For example, a peptide linker is an amino acid sequence that connects two functional components (e.g. peptides) via peptide bonds to generate a single, linear polypeptide chain.

In the present specification, the terms "target" and "binding partner" are used synonymously and can be exchanged. A target is any protein, peptide, fragment of a peptide, or other molecule such as glycosyl-structures capable of binding with an affinity as defined above to the targeting domain. Preferred target molecules are tumor antigens, such as proteins, glycosyl structures, or other epitopes that are present on the outside of a tumor cell but that are absent or less expressed on non-tumor cells or which are present in tumor tissue but absent or rare on normal tissue.

The term "antibody fragment" refers to a fragment of an antibody that has a specific binding affinity to an antigen. Examples of an antibody fragment include single-chain antibodies, diabodies, triabodies, tetrabodies, Fab fragments, F(ab') fragments, scFv, domain antibodies, minibodies, single-chain antibodies, and derivatives of antibody constant regions.

The term "coupling site" as employed herein means a cysteine or a cysteine rich amino acid sequence that is capable of reacting with other chemical groups to couple the compound of the invention to other chemical moieties.

The term "drug" means any substance which can affect any physical or biochemical properties of a biological organism, including but not limited to viruses, bacteria, fungi, plants, animals, and humans. In particular, the term includes any substance intended for diagnosis, treatment, or prevention of diseases in organisms, in particular humans or animals.

Generally known and practiced methods in the fields of molecular biology, cell biology, protein chemistry and antibody techniques are fully described in the continuously updated publications "Molecular Cloning: A Laboratory Manual", (Sambrook et al., Cold Spring Harbor); Current Protocols in Molecular Biology (F. M. Ausubel et al. Eds., Wiley & Sons); Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al., Eds., Wiley & Sons). Known techniques relating to cell culture and media are described in "Large Scale Mammalian Cell Culture (D. Hu et al., Curr. Opin. Biotechnol. 8:148-153, 1997); "Serum free Media" (K. Kitano, Biotechnol. 17:73-106, 1991); and "Suspension Culture of Mammalian Cells" (J. R. Birch et al. Bioprocess Technol. 10:251-270, 1990).

Embodiments of the Invention

The present invention will now be further described in more detail. Each embodiment defined below may be combined with any other embodiment or embodiments unless clearly indicated to the contrary. In particular, any feature indicated as being preferred or advantageous may be combined with any other feature or features indicated as being preferred or advantageous.

The present invention relates to a targeted compound for the coupling of chemical moieties comprising at least one targeting domain selected from a non-Immunoglobulin protein or an antibody fragment capable of binding a target with a binding constant $K_D$ of 500 nM or less, and at least one linking moiety consisting of up to about 80 amino acids wherein the linking moiety is essentially consisting of or consisting of alanine, proline, and serine, and at least one coupling site at the C-terminal or N-terminal end of a linking moiety wherein the coupling site is consisting of Cys (C), CXC, CXXC (SEQ ID NO: 35), or CXXXC (SEQ ID NO: 81), wherein X is selected from non-aromatic amino acids, and wherein a linking moiety connects the targeting domain and a coupling site and/or wherein a linking moiety connects two coupling sites. The one or more sites for coupling of chemical moieties consist of one cysteine or two cysteine residues interposed by 1, 2, or 3 non-aromatic amino acid residues. In preferred embodiments, a coupling site is located c-terminal of a linking moiety.

Structure of the Targeted Compound from the N-Terminus to the C-Terminus or from the C-Terminus to the N-Terminus.

Preferred embodiments are comprising T[LS]$_n$, optionally T[LS]$_n$cap, wherein n=1, 2, 3, 4, 5, 6, 7, 8, 9, 10, 11, 12, 13, 14, 15, 16, 17, 18, 19, or 20. In some embodiments of the invention, targeted compounds comprise of $T_m L_n S_o$ wherein m=1 or 2, n=1, 2, 3, or 4, o=1, 2, 3, or 4, optionally with cap.

The order of the components of the compound from the N-terminus to the C-terminus or the C-terminus to the N-terminus is, for example, as follows: targeting domain, linking moiety 1, coupling site 1, linking moiety 2, coupling site 2, linking moiety 3, coupling site 3. Further embodiments may comprise from the N-terminus to the C-terminus:

(i) targeting domain, linking moiety 1, coupling site 1, linking moiety 2, coupling site 2; optional additionally cap;
(ii) targeting domain, linking moiety 1, coupling site 1, linking moiety 2, coupling site 2, linking moiety 3, coupling site 3, linking moiety 4, coupling site 4, optional additionally cap;
(iii) targeting domain, linking moiety 1, coupling site 1, linking moiety 2, coupling site 2, linking moiety 3, coupling site 3, optional additionally cap;
(iv) coupling site 1, linking moiety 1, targeting domain, linking moiety 2, coupling site 2, optional additionally cap;
(v) targeting domain 1, linking moiety 1, coupling site 1, linking moiety 2, coupling site 2, targeting domain, linking moiety 3, coupling site 3, optional additionally cap;
(vi) targeting domain 1, targeting domain 2, linking moiety 1, coupling site 1, linking moiety 2, coupling site 2, optional additionally cap;
(vii) targeting domain 1, linking moiety 1, coupling site 1, linking moiety 2, coupling site 2, targeting domain 2, optional additionally cap.

See FIG. 1 for an illustration of i), ii), and iii). For example, the embodiment as described above as (iii) comprises three coupling sites for the coupling of chemical moieties at defined positions embedded in hydrophilic amino acids (i.e. linking moiety and cap) without secondary or tertiary structure.

Other permutations of targeting moiety, linking moiety, and coupling site are possible.

Terminal "cap" amino acids. In an embodiment of the invention, the coupling site of the invention is not directly located at the C- or N-terminus of the compound. In such embodiment, the compound further comprises a "cap", i.e., an amino acid sequence of 10 to 80 amino acids after the most terminally located coupling site. For example, in an embodiment wherein the targeted compound is a fusion protein, at least about 5, preferably about 10 amino acids are located between the terminal amino acid and the coupling site for site-specific coupling. Preferably, the cap essentially consists of or consists of any amino acid except aromatic amino acids or cysteine, thus preferably selected from alanine, proline, serine, valine, leucine, methionine, isoleucine, lysine, arginine, glutamic acid, aspartic acid, threonine, glutamine, glycine, asparagine, or histidine. Preferred are amino acids selected from alanine, proline, and serine. In preferred embodiments, the cap essentially consists of or consists of alanine, proline, and serine.

Size of the linking moiety/coupling site ($L_n S_o$) of the targeted compound. In one embodiment, the targeted compound is comprising the following formula: $T_m L_n S_o$ cap wherein n or o=1, 2, 3, 4, 5, 6, 7, 8, 9, 10, 11, 12, 13, 14, 15, 16, 17, 18, 19, or 20. Accordingly, $L_n S_o$ comprises between minimal about 5, preferably about 10 to maximal about 1800 amino acids. The total number of amino acids of $L_n S_o$cap is between about 20 to 1800 amino acids, preferably, 25 to 1000 amino acids, preferably 50 to 800 amino acids, preferably 70 to 500 amino acids, and preferably 100 to 300 amino acids.

Defined number and position of linking moieties. The targeted compound of the invention comprises at least one peptide linker covalently connecting the targeting domain and the coupling site and/or at least one peptide linker connecting two coupling sites. In one embodiment, the compound comprises two peptide linkers of 10 to 80 amino acids, one peptide linker connecting the targeting domain and the first coupling site, and a second peptide linker between the first and the second coupling site. In another embodiment, the compound comprises three peptide linkers of 10 to 80 amino acids, one peptide linker connecting the targeting domain and the first coupling site, a second peptide linker between the first and the second coupling site, and a third peptide linker between the second and the third coupling site. In a further embodiment, the compound comprises four peptide linkers of 10 to 80 amino acids, one peptide linker connecting the targeting domain and the first coupling site, a second peptide linker between the first and the second coupling site, a third peptide linker between the second and the third coupling site, and a fourth peptide linker between the third and the fourth coupling site. Further embodiments of the invention with up to 20 linkers are composed accordingly.

Defined number and position of coupling sites. Coupling sites according to this invention consist of Cys or CysXaaCys or CysXaaXaaCys (SEQ ID NO: 35) or CysXaaXaaXaaCys (SEQ ID NO: 81), wherein Xaa is not an aromatic amino acid (i.e. Xaa is not Phe, Trp, Tyr) or preferably not selected from Cys or Met or Ile or Leu. The defined number and defined position of coupling sites enables a site-specific coupling of chemical moieties to the targeted compound, i.e. to the targeted fusion protein. The compound of the invention contains a number of cysteine residues (at least 1 up to maximal 40) for conjugating chemical moieties. Thus, if required, a large number of chemical moieties can be coupled to a compound of the invention, and the compound with the coupled chemical moieties can be targeted specifically to the target. The number of coupling sites (i.e. cysteine or cysteine-containing peptide motifs) can be adjusted to the optimal number for a certain application by a person skilled in the art in order to adjust the amount of the chemical moieties accordingly. In one embodiment, a compound of the invention comprises two coupling sites (e.g. Cys or Cys rich motifs) located at the N- and at the C-terminal end of a linking moiety. In certain specific embodiments of the invention, the linking moiety consists of about 20 to 30 amino acids (Pro, Ser, and Ala), for example 18 to 33 amino acids, between two coupling sites of the compound.

Coupling sites in a compound are identical or different. In preferred embodiments, all coupling sites in a compound are identical.

Linking moieties without secondary or tertiary structure. The present invention further relates to a targeted compound wherein a linking moiety consists of 20-60% alanine, 20-40% proline, and 10-60% serine. Thus, a linker for the compound of the invention is hydrophilic and without secondary or tertiary structure. Thus, due to linker moieties without secondary or tertiary structure, the functional and structural characteristics of the targeting domain are maintained in the targeted compounds with defined number and location of coupling sites.

Defined length of a linking moiety of up to 80 amino acids. The length of the peptide linker varies between at least about 10 and up to a maximum of about 80 amino acids. More preferably, the peptide linker(s) of the invention have a length of between about 10 and about 80 amino acids. In a preferred compound, the linking moieties consist of about 10 to about 60 amino acids or about 20 to about 60 amino acids or about 40 to about 60 amino acids or about 60 to about 80 amino acids. Linkers can independently consist of about 10 to about 80 amino acids. For example, in one embodiment of the invention the first peptide linker consists of about 50 amino acids, and the second peptide linker consists of about 25 amino acids. For example, in one embodiment of the invention the first peptide linker consists of about 10 amino acids, the second peptide linker consists of about 25 amino acids, the third peptide linker consists of about 30 amino acids. For example, in another embodiment of the invention the first peptide linker consists of about 50 amino acids, the second peptide linker consists of about 60 amino acids, the third peptide linker consists of about 60 amino acids. For example, in another embodiment of the invention the first peptide linker consists of about 50 amino acids, the second peptide linker consists of about 75 amino acids, the third peptide linker consists of about 75 amino acids, and the fourth peptide linker consists of about 60 amino acids. The length of the peptide linkers in one construct can be different or identical.

Amino acid composition of linking moieties. The composition of peptide linkers in one compound can be different or identical. In preferred embodiments of the invention, the peptide linkers of the compound independently consist of amino acids selected from Ala, Pro, or Ser. It is preferred that the peptide linkers consist of about 30% to about 60% alanine, about 20% to about 45% proline, and about 10% to about 60% serine, preferably about 40% to about 60% alanine, about 20% to about 40% proline, and about 10% to about 30% serine. In one embodiment, the peptide linkers consist of about 50% alanine, about 30% proline, and about 20% serine. It is further preferred that the amino acids alanine, proline, and serine are evenly distributed throughout the linker amino acid sequence so that not more than a maximum of 2, 3, 4, or 5 identical amino acid residues are adjacent, preferably a maximum of 3 amino acids. A preferred linker of the invention is proteolytically stable. Table 1a shows exemplary amino acid compositions of suitable linking moieties for targeted compounds of the invention.

TABLE 1a

Amino acid compositions of suitable linking moieties for targeted compounds.

| SEQ ID NO: | amino acid sequence | Length (aa) | Ala (%) | Pro (%) | Ser (%) |
|---|---|---|---|---|---|
| 3 | SAPAPSAPAASAPPAPAAPAAPASAPAPAPAPAASPSPAAPAPSPA | 49 | 49 | 37 | 14 |
| 4 | PAPASPASAPSAPASAPPAAPSAA | 24 | 46 | 33 | 21 |
| 5 | PAPSAPAPAASPAAAPASAAPASA | 25 | 54 | 29 | 17 |
| 6 | SAPAPSAPAASAPPAPAAPAAPAAPASAPAPAPAPAPAA | 49 | 54 | 36 | 10 |
| 7 | ASPAPAPSPASPAPASPASAPSAPASAPPAAPSASPAPSAPAPAAASPA | 59 | 43 | 35 | 22 |

TABLE 1a-continued

Amino acid compositions of suitable linking moieties for targeted compounds.

| SEQ ID NO: | amino acid sequence | Length (aa) | Ala (%) | Pro (%) | Ser (%) |
|---|---|---|---|---|---|
| 8 | APASAAPASASAPAPSAPAASAPPAPAAPAAPAAPASAPAPAPAPAAAP | 59 | 55 | 33 | 12 |
| 9 | PAAPAPSPSAPAPASPASAPSAPASAPPAAPSAASPAPS | 49 | 41 | 36 | 23 |
| 10 | PAPASASPAAAPASAAPASA | 20 | 55 | 25 | 20 |
| 11 | SAPAPSAPAASAPPAPAAPAAPAAPASAPAPAPAPAAAPSPAAPAPSPASPAPASPASA | 59 | 49 | 36 | 15 |
| 12 | ASPSAPPPAAPSAASPAPSAPAPAAASPAAAPSAAPASASAPAPSAPAAPPAPAAPAAPAAPASAPAPAPAPA | 74 | 51 | 34 | 15 |
| 13 | APSPAAPAPSPASAAAPAPASPASAPSAPASAPPAAPSAASPAPSAPAPASASPAAAPSAAPAASASAPAPSPA | 74 | 47 | 31 | 22 |
| 14 | APSPAPAAPAAPASAAAPASAPAPAPAPAAAPSPAAPAPSPAAPAPASPASAPSAPAPS | 59 | 50 | 36 | 15 |
| 15 | APAPSAASPAPSAPAPASASPAAAPASAPA | 30 | 50 | 30 | 20 |
| 16 | ASPASAAPAA | 10 | 60 | 20 | 20 |
| 17 | APAPASAPAAAPSPAAPAPSPAPAPA | 26 | 50 | 38 | 12 |
| 18 | APSAPASASPPSAPSASAASSASAPAAA | 28 | 46 | 21 | 32 |
| 19 | APASAAPASASAPAPSSAPAAS | 22 | 50 | 23 | 27 |
| 20 | APAPASPASAPSAPASAPPAAPSAASPAPSAPAPASASPAAAPSAAPAASASAPAPSAPAAPSPAPAAPAAPAS | 74 | 49 | 31 | 20 |
| 21 | AAPASAPAPAPAPAAAPSPAAPAPSPAAPAPASPASAPSAPASAPPAAPSAASPAPSAPAPASASPAAAPASAPA | 75 | 49 | 33 | 17 |
| 22 | SAPAPSAPAASAPPAPAAPAAPAAPASAPAPAPAPAAAPSPAAPAPSPA | 49 | 51 | 37 | 12 |
| 23 | PAPASPASASPASAPSAPPAAPSAASPAPSAPAPASASPAAAPASAAPASA | 50 | 48 | 30 | 22 |
| 24 | SAPAPSAPAASAPPAPAAPAA | 47 | 52 | 33 | 14 |
| 25 | SAPSAPAASAPPAPAAPAAPAPASAPAPAPAPAAPSPAAPAPSPAA | 46 | 50 | 37 | 13 |
| 26 | ASPAPASAPSAPASAPPAAPSAASPAPSAPAPASASPAAAPASAPSA | 47 | 47 | 30 | 23 |
| 27 | ASPSAPSAPSPPAPAAPAAPAAAPAPAPAPAAPSPAAPAPSPAA | 46 | 48 | 39 | 13 |
| 28 | ASPAPSAAPSAPASAPPAAPSAAAPAPSPAPAPASAAPAAPASAPSA | 47 | 49 | 32 | 19 |
| 29 | SAPSAPAAPSPPAPAAPAAPAPASAPAPAPAPAAPSPAAPAPSPAA | 46 | 48 | 39 | 13 |
| 30 | ASPAPASAPSAPASAPPAAPSAASPAPSPAPAPASASPAAPASAPSA | 47 | 45 | 32 | 23 |
| 31 | SAPSAPAAPSPPAPAAPAAPAAAPAPAPAPAAPSPAAPAPSPAA | 46 | 50 | 39 | 11 |
| 32 | ASPAPAAPSAPASAPPAAPSAAAPAPSPAPAPASAAPAAPASAPSA | 47 | 51 | 32 | 17 |
| 33 | SAPAPSSAPAASAPPAAASAAPAA | 24 | 54 | 25 | 21 |
| 34 | APASAAPASA | 10 | 60 | 20 | 20 |
| 55 | SAPAPSAPAASAPPAPAAPAAPAAPASAPAPA | 32 | 53 | 34 | 12.5 |
| 56 | APAASPSPAAPAPSPASPAPASPASAPSAPAS | 32 | 40 | 34 | 25 |
| 57 | PPAAPSAASSPAPSAPAPAASPAAAPASAAPASA | 34 | 50 | 29 | 21 |
| 58 | SAPAPSAPAASAPPAPAAP | 19 | 47 | 37 | 16 |
| 59 | APAAPASAPAPASAPAASP | 19 | 52 | 32 | 16 |
| 60 | PAAPAPSPASPAPASPAPSSA | 21 | 38 | 38 | 24 |
| 61 | SAPAPSAPAASAPPAPAAPAAPAAPASAPAPAPAPAASPS | 40 | 50 | 35 | 15 |

TABLE 1a-continued

Amino acid compositions of suitable linking moieties for targeted compounds.

| SEQ ID NO: | amino acid sequence | Length (aa) | Ala (%) | Pro (%) | Ser (%) |
|---|---|---|---|---|---|
| 62 | SAPAASPSPAAPAPSPASPAPASPASAPSAPASAPPAASA | 40 | 43 | 32 | 25 |
| 63 | PAAPAPSPASPAPASPASAP | 18 | 33 | 44 | 22 |
| 64 | SAPAPSAPAASAPPAPAAAPAAPAAPASAPAPA | 33 | 55 | 33 | 12 |
| 65 | APAASPSPAAAPAPSPASPAPASPASAPSAPAS | 33 | 42 | 33 | 24 |
| 66 | PPAAPSAASSPAPSAPAPAAASPAAAPASAAPASA | 35 | 41 | 29 | 20 |
| 67 | SAPAPSAPAAASAPPAPAAP | 20 | 50 | 35 | 15 |
| 68 | APAAAPASAPAPASAPAASP | 20 | 55 | 30 | 15 |
| 69 | PAAAPAPSPASPAPASPAPSSA | 22 | 41 | 36 | 23 |
| 70 | SAPAPSAPAASAPPAPAAPAAAPAAPASAPAPAPAASPS | 41 | 51 | 34 | 15 |
| 71 | SAPAASPSPAAAPAPSPASPAPASPASAPSAPASAPPAASA | 41 | 44 | 32 | 24 |
| 72 | PAAAPAPSPASPAPASPASAP | 21 | 43 | 38 | 19 |

In one embodiment of the invention, the coupling site is a cysteine located at the c-terminal end of a linking moiety. Amino acid compositions of selected examples for linking moieties with c-terminal coupling site (Cysteine) are shown in Table 1b.

TABLE 1b

Amino acid compositions of examples for linking moieties with c-terminal coupling site
amino acid sequence

SAPAPSAPAASAPPAPAAPC

APAAAPASAPAPASAPAASPC

SAPAPSAPAASAPPAPAAPAAAPAAPASAPAPAC

APAASPSPAAPAPSPASPAPASPASAPSAPASC

Two linking moieties each with c-terminal coupling site can be connected, for example:

(SEQ ID NO: 73)
SAPAPSAPAASAPPAPAAPCAPAAAPASAPAPASAPAASPC, (SEQ ID NO: 75)
SAPAPSAPAASAPPAPAAPCAPAAPASAPAPASAPAASPC.

In preferred embodiments, a c-terminal "cap" is added after the most c-terminal coupling site:

(SEQ ID NO: 74)
SAPAPSAPAASAPPAPAAPCAPAAAPASAPAPASAPAASPCPAAPAPSPA

SPAPASPASAP, (SEQ ID NO: 76)
SAPAPSAPAASAPPAPAAPCAPAAPASAPAPASAPAASPCPAAPAPSPAS

PAPASPASAP.

Preferably, the amino acid sequences of the linking moiety comprise or essentially consist of SEQ ID NOs: 3 to 34 and SEQ ID NOs: 55 to 76 or amino acid sequences with at least 85% identity to SEQ ID NOs: 3 to 34 and SEQ ID NOs: 55 to 76.

For example, an exemplary targeted compound has two defined coupling sites at defined location embedded in linking moieties without secondary or tertiary structure so that a specific coupling of chemical moieties is given and the functional and structural characteristics of the targeting domain are maintained.

Defined composition of coupling sites. Coupling sites according to this invention consist of Cys (C) or CXC or CXXC (SEQ ID NO: 35) or CXXXC (SEQ ID NO: 81). The present invention further relates to a targeted compound wherein X is selected from non-aromatic amino acids. Amino acids that are excluded as X in the coupling site between two cysteines are aromatic amino acids (Phe, Tyr, Trp), and preferably hydrophobic amino acids (Ile, Leu, Met, Cys). Preferably, amino acids in the coupling site between two cysteines are selected from small or hydrophilic amino acids such as Pro, Ser, Ala, Val, Gly, Thr, Asn, Asp, Gln, Glu, Lys, Arg, and His. Non-limiting examples for coupling sites with CXXC motif (SEQ ID NO: 35) are CPAC (SEQ ID NO: 36), CSSC (SEQ ID NO: 37), CAAC (SEQ ID NO: 38), or CASC (SEQ ID NO: 39). The compound of the invention comprises 1, 2, 3, 4, 5, 6, or more, up to 20, coupling sites.

Targeting domain. In an embodiment, a targeted compound of the invention comprises a non-Ig protein or an antibody fragment (for example a Fab fragment) as targeting domain. The targeted compound of the invention does not comprise a full-length antibody. A disadvantage of full-length antibodies is that the Fc part of the antibody can bind to cellular receptors independently of the targeting specificity of the variable domain and thereby initiate undesired reactions. In contrast to full-length monoclonal antibodies, non-Ig proteins or antibody fragments bind specifically to the desired target but not to other proteins. Furthermore, non-Ig proteins are small proteins, easy to engineer and can be produced in microorganisms, thus providing technical advantages.

In an embodiment, a targeting domain is a non-Ig protein with a dissociation constant $K_D$ to a target between 0.001 nM and 500 nM, preferably below 100 nM, preferably below 10 nM, more preferably below 1 nM. In some embodiments of the invention, targeted compounds, for example targeted fusion proteins, comprise one, two, or more targeting domains. In some embodiments, two identical targeting domains are connected via a peptide linker. In other embodiments, two different targeting domains are connected via a peptide linker. The different targeting domains may have specificity for the same epitope or for the same target protein, but for different epitopes. In another embodiment the different targeting domains may have specificity for different target proteins, i.e. the compound is bi-specific.

In one embodiment, the two targeting domains may be connected to linking moieties on both of their N- and C-termini. In other embodiments, one targeting domain is at the N- or C-Terminus of the compound while the second targeting domain is connected to linking domains on both of its N- and C-Termini. In yet another embodiment, both targeting domains are connected to a linking domain only on one of their N- or C-termini, i.e. the fusion protein comprises a first targeting domain at the N-terminus and a second targeting domain at the C-terminus.

Determination of binding affinity targeting domain. Methods for determining binding affinities, i.e. for determining the dissociation constant Ko, are known to a person of ordinary skill in the art and can be selected for instance from the following methods known in the art: surface plasmon resonance (SPR) based technology, Bio-layer interferometry (BLI), enzyme-linked immunosorbent assay (ELISA), flow cytometry, fluorescence spectroscopy techniques, isothermal titration calorimetry (ITC), analytical ultracentrifugation, radioimmunoassay (RIA or IRMA), and enhanced chemiluminescence (ECL). Some of the methods are described in more detail in the Examples below. Typically, the dissociation constant $K_D$ is determined at temperatures between about 20° C. and about 37° C. If not specifically indicated otherwise, the $K_D$ values recited herein are determined at 25° C. by SPR analysis.

Further characterization of targeted compound. The further characterization of the targeted compounds of the invention, for example of the fusion proteins of the invention or of the non-Ig-proteins, for example ubiquitin muteins, can be performed in the form of the isolated, soluble proteins. The appropriate methods are known to those skilled in the art or described in the literature. Such methods include the determination of physical, biophysical and functional characteristics of the proteins. The affinity and specificity of the variants isolated can be detected by means of biochemical standard methods as discussed above and in the Examples and as known to those skilled in the art. For stability analysis, for example, spectroscopic or fluorescence-based methods in connection with chemical or thermal unfolding are known to those skilled in the art, including e.g. differential scanning fluorimetry (DSF).

Suitable non-Iq proteins as targeting domain. Examples of suitable non-Ig proteins are selected from, but not limited to, the following proteins: AFFILIN® (ubiquitin muteins), DARPin (ankyrin repeat protein muteins), Anticalin (lipocalin muteins), Affibody (muteins of the Z-domain of staphylococcal protein A), Fynomer (mutein of human Fyn SH3 domain), AdNectin (mutein of the tenth domain of human fibronectin), Kunitz domain peptides (muteins of Kunitz domains of various protease inhibitors), Nanofitins (Sac7d muteins), Avimers (muteins of multimerized Low Density Lipoprotein Receptor-A), chagasin scaffold or chagasin-like protease inhibitor proteins, Adnexin scaffold, Centryrin (FN3 domain muteins), Knottin (cysteine-knot miniprotein muteins), Armadillo-repeat protein muteins, Atrimers (tetranectin muteins; C-type lectin domain muteins), or CTLA4 based muteins. Additional information on scaffolds based on non-Ig proteins is provided for example in Vazquez-Lombardi et al., Drug Discov. Today, 2015 20: 1271-1283 or in Weidle et al., Cancer Genomics and Proteomics 2013 10: 155-168.

Suitable antibody fragments as targeting domain. Selected examples for suitable fragments derived from antibodies are single-chain antibodies, derivatives of antibody constant regions, diabodies, triabodies, tetrabodies, Fab fragments, F(ab') fragments, scFv, or domain antibodies (e.g. Nanobodies or Abdurins).

Examples for suitable targets. The non-Ig protein binds with detectable specific binding affinity to a target, for example, a target that is associated with a certain disease, e.g. in cancer, autoimmune or cardio-vascular diseases. Examples for binding partners for the targeting domain are cell surface expressed targets, selected from but by no means limited to Her2, EGFR, ED-B, PSMA, or VEGF-A. It should be noted that a plurality of possible targets can be used. A compound of the invention comprising two or more targeting domains may bind to the same target, but to different epitopes. For example, a compound having two non-identical targeting domains each with affinity for Her2 may bind to different Her2-epitopes. A compound of the invention comprising two or three targeting domains may be bi-specific or tri-specific and bind to two or three different targets. For example, a compound having a targeting domain with affinity for Her2 and a second targeting domain with affinity for EGFR binds to both Her2 and EGFR.

AFFILIN® as example for a targeting domain. Preferably, the targeting domain of the targeted compound is a ubiquitin mutein (AFFILIN®) exhibiting 80% to 94% identity to ubiquitin (SEQ ID NO: 1) or 80% to 94% identity to bis-ubiquitin (SEQ ID NO: 2), provided that the AFFILIN® has a specific binding affinity to a target. In other words, ubiquitin muteins are modified in 5, 6, 7, 8, 9, 10, 11, 12, 13, 14, 15, or 16 amino acids compared to SEQ ID NO: 1, preferably modifications in 6, 7, 8, 9, 10, or 11 amino acids of SEQ ID NO: 1, or in 10 to 32 amino acids compared to SEQ ID NO: 2, preferably modifications in 12 to 22 amino acids of SEQ ID NO: 2, to generate a non-natural protein with newly created measurable binding properties to a target antigen.

Identification of a targeting domain. The derivatization of a non-Ig protein, for example, of a ubiquitin to generate a mutein that specifically binds to a particular target antigen has been described in the art. For example, a library can be created in which for example the sequence as shown in SEQ ID NO: 1 or SEQ ID NO: 2 has been altered. Preferably, the alteration is a substitution, insertion, or deletion as described in the art. The substitution of amino acid residues for the generation of the novel binding proteins derived from ubiquitin can be performed with any desired amino acid. This is described in detail in EP1626985B1, EP2379581B1, and EP2721152, which are incorporated herein by reference.

The step of modification of the selected amino acids is performed according to the invention preferably on the genetic level by random mutagenesis of the selected amino acids. A pre-selection of the amino acids to be modified by substitution, insertion or deletion can be performed based on structural information available for the ubiquitin protein to be modified. Preferably, the modification of the non-Ig protein is carried out by means of methods of genetic engineering for the alteration of a DNA belonging to the respective protein. The selection of different sets of amino acids to be randomized leads to different libraries. The gene pool libraries obtained can be combined with appropriate functional genetic elements which enable expression of proteins for selection methods such as display methods. The expressed proteins are contacted with a target molecule to enable binding of the partners to each other if a binding affinity exists. This process enables identification of those proteins which have a binding activity to the target molecule. Contacting according to the invention is preferably performed by means of a suitable presentation and selection method such as the phage display, ribosomal display, mRNA display or cell surface display, yeast surface display or bacterial surface display methods, preferably by means of the phage display method as known to someone skilled in the art. Identified clones with desired binding properties are then sequenced to reveal the amino acid sequences of muteins. The identified binding protein may be subjected to further maturation steps, e.g. by generating additional libraries based on alterations of the identified sequences and repeated phage display, ribosomal display, panning and screening steps as described above and as known to someone skilled in the art.

In one embodiment of the invention, in order to generate a measurable binding affinity with a $K_D$ of at least e.g. $10^{-7}$ M to a target, a ubiquitin is at least substituted in 5 amino acids selected from positions 62, 63, 64, 65, 66, 67, or 68 of SEQ ID NO: 1. Further 1, 2, 3, 4, 5, or 6 amino acids might be modified to generate a measurable binding affinity to a target.

In one embodiment, the targeting moiety of a compound of the invention comprises a ubiquitin mutein based on SEQ ID NO: 1 wherein the alteration is carried out at 1, 2, 3, 4, 5, 6, 7, 8, 9, 10, or 11, preferably a total of 5, 6, 7, 8, or 9 amino acids located in (i) region 2 to 11, or (ii) region 62 to 68, or (iii) in both regions simultaneously. Further positions not comprised by these regions might be altered as well.

Specific examples for AFFILIN® proteins as targeting domain. In one embodiment of the invention, in order to generate a measurable binding affinity with a $K_D$ of at least e.g. $10^{-7}$ M to a target, a ubiquitin moiety is at least substituted in 5 amino acids corresponding to positions 62, 63, 64, 65, 66 of SEQ ID NO: 1, preferably in combination with an insertion of 2-10 amino acids in the loop region corresponding to positions 8 to 11 of SEQ ID NO: 1, preferably between positions 9 and 10 of SEQ ID NO: 1 (for example, EGFR-specific AFFILIN®-139819; SEQ ID NO: 41).

In another embodiment of the invention, two ubiquitin moieties are independently at least substituted in 5, 6, 7, 8, or 9 amino acids selected from and corresponding to regions 2 to 11 and 62 to 68, for example selected from positions 2, 4, 6, 8, 62, 63, 64, 65, 66, 68 of SEQ ID NO: 1, and the two ubiquitin moieties are connected directly or via a peptide linker, preferably directly connected.

In yet another embodiment, the binding moiety of the present invention relates to a binding protein with binding affinity (Ko) of less than 500 nM for a target, wherein the target binding protein comprises an amino acid sequence wherein two ubiquitin moieties are independently substituted in at least 7 amino acids wherein the substitutions in the first ubiquitin moiety are at least selected from positions 42, 44, 68, 70, 72, 73, and 74 of SEQ ID NO: 1 and wherein the substitutions in the second ubiquitin moiety are at least selected from positions 6, 8, 62, 63, 64, 65, 66 of SEQ ID NO: 1, and wherein the two ubiquitin moieties are connected directly without any linker. Further, the binding protein has at least 85% sequence identity to bis-ubiquitin (SEQ ID NO: 2). A target binding ubiquitin mutein may comprise 1, 2, 3, 4, 5, or 6 further substitutions to generate a binding protein for a target with high affinity, for example, a Her2-specific binding protein (AFFILIN®-142628; SEQ ID NO: 40).

In yet another embodiment, the target binding ubiquitin mutein may comprise substitutions in the first ubiquitin moiety at least selected from positions 6, 8, 62, 63, 64, 65, 66 of SEQ ID NO: 1 and in the second ubiquitin moiety at least selected from positions 6, 8, 62, 63, 64, 65, 66 of SEQ ID NO: 1, and wherein the two ubiquitin moieties are connected with a short peptide linker to generate a binding protein for a target with high affinity, for example, an ED-B-specific binding protein, for example as disclosed in EP2513138B1 which is incorporated herein by reference.

Examples for VEGF-A specific AFFILIN® proteins are provided in WO2012/172054.

In further preferred embodiments, fusion proteins of the invention comprise, essentially consist of or consist of an amino acid sequence selected from the group consisting of SEQ ID NOs: 42 to 51, or amino acid sequences with at least 85% identity to SEQ ID Nos: 42 to 51, or functional variants thereof.

The present invention further relates to a targeted compound wherein the targeted compound is a fusion protein. Examples for fusion proteins are shown in amino acid sequences SEQ ID NOs: 42 to 51.

Specific examples for chemical moieties. The present invention relates to a targeted compound wherein the chemical moieties that are coupled to the coupling site of the compound are selected from dyes, chelators, drugs, toxins, and small molecules. Examples for small molecules are low molecular weight (below about 5000 Daltons) organic compounds. An example for a suitable dye is EDANS (5-[(2-aminoethyl)amino]naphthalene-1-sulfonic acid). An example for a chelator is DOTA which can be used as complexing agent for molecules with various structures, including radioisotopes. Resulting compounds can be used with a number of e.g. radioisotopes, in particular for a use in medical applications. Examples for toxins are selected from, but by no means limited to, auristatins, tubulysins, amanitins, doxorubicin, maytansines, calicheamicin, vinca alkaloids, camptothecin, and duocarmycin.

Use of the targeted compound. The present invention also relates to a use of the targeted compound in diagnostic or therapeutic applications. Targeted compounds with coupled chelators, drugs, toxins, and small molecules can be particularly useful in therapeutic applications, for example in cancer therapy. For example, compounds with dyes coupled to the coupling site can be useful in diagnostic applications, for example in cancer diagnosis. For example, compounds with chelators coupled to the coupling site can be useful in diagnostic or therapeutic applications; for example, further substances such as radioisotopes can be coupled to chelators.

Composition of the targeted compound. The present invention also relates to a composition of a targeted compound and to a kit comprising the composition of the targeted compound. A kit comprises a composition of a targeted compound in a predefined amount and optionally further components such as solutions, buffers, handling devices, and others, suitable for handling the compound or preparing the targeted compound for further use.

Method for the preparation of a targeted compound. The present invention is further directed to a method for the preparation of a targeted compound according to the invention as detailed above, said method comprising the following steps: preparing a nucleic acid encoding a fusion protein as defined above; introducing said nucleic acid into an expression vector; introducing said expression vector into a host cell; cultivating the host cell; subjecting the host cell to culturing conditions under which a fusion protein is expressed, thereby producing a fusion protein as described above; optionally isolating the fusion protein produced in step (e); and optionally conjugating the fusion protein with further functional moieties as described above. Cultivation of cells and protein expression for the purpose of protein production can be performed at any scale, starting from small volume shaker flasks to large fermenters, applying technologies well-known to those skilled in the art.

EXAMPLES

The following Examples are provided for further illustration of the invention. The invention, however, is not limited thereto, and the following Examples merely show the practicability of the invention on the basis of the above description. For a complete disclosure of the invention reference is made also to the literature cited in the application which is incorporated completely into the application by reference.

Example 1. Generation of Expression Constructs

A schematic drawing of preferred compounds of the invention is provided in FIG. 1. Fusion proteins have the following structural features: targeting domain-(linker-coupling site)$_n$-cap. Specific fusion proteins were generated comprising (i) as targeting domain a Her2-specific binding protein protein or an EGFR-specific binding protein; (ii) as linking moiety 22 to 74 amino acids selected from Ala, Pro, Ser (referred to as "APS" in Table 2), 2, 3, or 4 linking moieties in the fusion protein; (iii) as coupling site the amino acid Cys or the peptide motif Cys-Pro-Ala-Cys (SEQ ID NO: 36) regularly spaced between the linking moieties with minimum distance between each coupling of 22 amino acids and maximum distance of 74 amino acids; (iv) as cap at the C-terminus 10 to 30 amino acids (selected from Ala, Pro, Ser) to avoid a terminal position of a coupling site.

TABLE 2

Examples for fusion proteins

| Clone number (CID) | SEQ ID NO: | $T_mL_nS_o$cap | linker (L) (number of amino acids) | total number of Cys in "S" | cap length (number of amino acids) |
|---|---|---|---|---|---|
| 146414 | 43 | Affilin-(APS-Cys)$_2$-cap- | L$_1$ 49, L$_2$ 24 | 2 | 25 |
| 146416 | 44 | Affilin-(APS-Cys)$_4$-cap- | L$_1$ 39, L$_2$ 49, L$_3$ 49, L$_4$ 39 | 4 | 20 |
| 146418 | 45 | Affilin-(APS-Cys)$_4$-cap- | L$_1$ 59, L$_2$ 74, L$_3$ 74, L$_4$ 59 | 4 | 30 |
| 143276 | 42 | Affilin-(APS-Cys)$_2$-cap- | L$_1$ 49, L$_2$ 24 | 2 | 25 |
| 140353 | 52 | Affilin-(APS-CysProAlaCys)$_3$-cap | L$_1$ 26, L$_2$ 28, L$_3$ 22 | 6 | 10 |
| 140153 | 50 | Affilin-(APS-CysProAlaCys)$_3$-cap- | L$_1$ 24, L$_2$ 26, L$_3$ 23 | 6 | 10 |
| 140350 | 51 | Affilin-(APS-CysProAlaCys)$_3$-cap- | L$_1$ 24, L$_2$ 26, L$_3$ 23 | 6 | 10 |

AFFILIN® proteins used as targeting domains: EGFR-specific AFFILIN®-139819 (SEQ ID NO: 41) with a K$_D$ for EGFR of about 20 nM and thermal stability at 73° C.; Her2-specific AFFILIN®-142628 (SEQ ID NO: 40) with a K$_D$ for Her2 of about 0.4 nM and thermal stability at 62° C. Any other target specific functional variants of these AFFILIN® binding proteins or other target-specific non-Ig proteins or target-specific antibody fragments could be used. Genes were synthesized and cloned into an E. coli expression vector using standard methods known to a person skilled in the art. C-terminal tags (e.g. StrepTagII, SEQ ID NO: 54, or/and His Tag, SEQ ID NO: 53) were added to enable standard purifications protocols. DNA sequencing was used to verify the correct sequence of the fusion proteins.

Example 2. Expression of Fusion Proteins

HMS174 (DE3) competent cells were transformed with expression plasmids. Cells were spread onto selective agar plates (Kanamycin) and incubated overnight at 37° C. Precultures were inoculated from single colony in 100 ml superrich medium (modified H15 medium 2% glucose, 5% yeast extract, 1% Casamino acids, 0.76% glycerol, 0.7% lactose, 1% Torula yeast RNA, 250 mM MOPS, 202 mM TRIS, 10 mg/L RNase A, pH 7.4, Antifoam SE15) and cultured 16 hours at 37° C. at 160 rpm in a conventional orbital shaker in baffled 1 L Erlenmeyer flasks supplemented with 150 µg/ml Kanamycin without lactose and antifoam. Main culture was inoculated from previous overnight culture with an adjusted start-OD$_{600}$ of 0.5 in 400 ml superrich medium in 1 L thick-walled Erlenmeyer flasks that was supplemented with glycerol, glucose, lactose, antifoam agent and 150 µg/ml Kanamycin. Cultures were transferred to a resonant acoustic mixer (RAMbio) and incubated at 37° C. with 20×g. Aeration was facilitated by Oxy-Pump stoppers. Recombinant protein expression was induced by metabolizing glucose and subsequently allowing lactose to enter the cells. At predefined time points OD$_{600}$ was measured, samples adjusted to 5/OD$_{600}$ were withdrawn, pelleted and frozen at −20° C. Cells were grown overnight for approximately 24 hours to reach a final OD$_{600}$ of about 45-60. To collect biomass cells were centrifuged at 16000×g for 10 min at 20° C. Pellets were weighed (wet weight) and pH was measured in the supernatant. Cells were stored at −20° C. before processing.

Example 3: Analysis of Expression and Solubility of Fusion Proteins

Samples taken during fermentation were re-suspended in 300 µl extraction buffer (PBS supplemented with 0.2 mg/ml Lysozyme, 0.5× BugBuster, 7.5 mM MgSO$_4$, 40 U Benzonase) and solubilized by agitation in a thermomixer at 700 rpm at room temperature for 15 min. Soluble fusion proteins were separated from insoluble fusion proteins by centrifugation (16000×g, 2 min, rt). Supernatant was withdrawn (soluble fraction) and the pellet (insoluble fraction) was re-suspended in equivalent amount of urea buffer (8 M urea, 0.2 M Tris, 2 mM EDTA, pH 8.5). From both soluble and insoluble fraction 50 µl were taken and 12 µl 5× sample buffer as well as 5 µl 0.5 M DTT were added. Samples were boiled at 95° C. for 5 min. Finally 8 µl of those samples were applied to a SDS-gel which was then run in accordance to the manufacturer's recommendations.

Example 4: Purification of Fusion Proteins

All fusion proteins were expressed in the soluble fraction of E. coli with a C-terminal StrepTagII. The cells were lysed by sonication (1 g biomass) and the first purification step was performed with cation exchange chromatography using HiTrap SP HP columns 1 ml, 50 mM sodium acetate pH 4.0 according to the manufacturer's instructions. The eluted fractions were injected to a size exclusion chromatography column XK16/600 Superdex 200 pg (GE Healthcare) equilibrated with 20 mM citrate pH 6.0 and 150 mM NaCl. The peak fractions were pooled and analyzed by SDS-PAGE.

TABLE 3

Purification of fusion proteins.

| Fusion protein | Yield biomass (mg/g) |
|---|---|
| 146414 | 5.2 |
| 146416 | 8.0 |
| 146418 | 5.5 |
| 143276 | 4.0 |
| 140350 | 0.2 |

Example 5. Thermal Stability of Target-Specific Fusion Proteins

Thermal stability of the fusion proteins of the invention was determined by Differential Scanning Fluorimetry. Each probe was transferred at a concentration of 0.1 µg/µL to a MICROAMP® Optical 384-well plate (ThermoFisher), and SYPRO Orange dye was added at suitable dilution. A temperature ramp from 25 to 95° C. was programmed with a heating rate of 1° C. per minute (ViiA-7 Applied Biosystems). Fluorescence was constantly measured at an excitation wavelength of 520 nm and the emission wavelength at 623 nm (ViiA-7, Applied Biosystems). Similar melting points correlate to related protein structures.

Example 6. Analysis of Target Binding by ELISA

The affinities of the fusion proteins towards the specific targets (e.g. Her2, EGFR) were determined using an Enzyme Linked Immunosorbent Assay (ELISA). The target was immobilized on a 96 well Nunc MaxiSorb ELISA plate (2 µg/ml). After incubation for 16 h at 4° C. the wells were washed three times with PBST (PBS+0.1% Tween 20) and the wells were blocked with 3% BSA in PBS (2 h at room temperature). The negative controls were wells only blocked with BSA. After blocking, the wells were washed three times with PBST and incubated for 1 h with the fusion protein (in PBST) at room temperature. After incubation the wells were washed three times with PBST and subsequently incubated with Strep-Tactin-HRP (1:10000) (from IBA) for 1 h at room temperature. Afterwards the wells were washed three times with PBST and three times with PBS. The activity of the horseradish peroxidase was visualized by adding TMB-Plus substrate. After 30 min the reaction was stopped by adding 0.2 M $H_2SO_4$ and the absorbance was measured at 450 nm.

Example 7: Analysis of Target Binding by Surface Plasmon Resonance

A CM5 sensor chip (GE Healthcare) was equilibrated with SPR running buffer. Surface-exposed carboxylic groups were activated by passing a mixture of EDC and NHS to yield reactive ester groups. 700-1500 (1028) RU on-ligand (rProtein A) was immobilized on a flow cell, off-ligand was immobilized on another flow cell. Injection of ethanolamine after ligand immobilization removes non-covalently bound ligand (hHER2-Fc for AFFILIN®-142628, fusion proteins 146414, 146416, and 146418; hEGFR-Fc for AFFILIN®-139819, fusion proteins 143276 and 140350). Upon ligand binding, the protein analyte was accumulated on the surface increasing the refractive index. This change in the refractive index was measured in real time and plotted as response or resonance units (RU) versus time. The analytes were applied to the chip in serial dilutions with a suitable flow rate (30 µl/min). After each run, the chip surface was regenerated with regeneration buffer and equilibrated with running buffer. The control samples were applied to the matrix. Regeneration and re-equilibration were performed as previously mentioned. Binding studies were carried out by the use of the BIACORE® 3000 (GE Healthcare); data evaluation was operated via the BIAevaluation 3.0 software, provided by the manufacturer, by the use of the Langmuir 1:1 model (RI=0). Evaluated dissociation constants ($K_D$) were standardized against off-target. Results are shown in Table 4 (see Example 9).

Example 8. Labeling of Fusion Protein

A. Labeling of Fusion Protein with EDANS-C2-Maleimid
35 µM fusion protein (Her2 specific CIDs146414, 146416 and 146418; EGFR specific CID143276; with three linking moieties and three coupling sites "CPAC" either C-terminal of the AFFILIN®, CID140350, or N-terminal of the AFFILIN®, CID140353) (each 0.632 mg/ml) were incubated with 10fold excess of EDANS (5-((2-aminoethyl)amino) naphthalene-1-sulfonic acid) in 20 mM phosphate buffer pH 7.0 for 1 h at room temperature. After blocking the non-reacted maleimids with 1 M cysteine for 1 h at rt, the samples were desalted using Hitrap columns (5 ml, GEHC) and PBS as running buffer. MALDI-TOF analysis was used to determine the degree of labeling.

B. Labeling of Fusion Protein with DOTA
Fusion proteins comprising two linking domains and two cysteins as coupling sites at the C-terminus of each linking domain and a "cap" at the C-terminus of the fusion protein were incubated with 20-fold excess of Maleimide-DOTA (2,2',2"-(10-(2-((2-(2,5-dioxo-2,5-dihydro-1H-pyrrol-1-yl) ethyl)amino)-2-oxoethyl)-1,4,7,10-tetraazacyclododecane-1,4,7-triyl)triacetic acid, CheMatech) in 50 mM HEPES, 150 mM sodium chloride, 5 mM EDTA pH 7.0 for 3 h at room temperature. In order to reduce metal ions that might interact with DOTA-molecules all columns and AKTA devices (GE Healthcare) were incubated with 0.1 M EDTA solution for 30 minutes. For preparing solutions only metal-free or metal-reduced components were used. After the incubation the samples were separated from unbound DOTA molecules via size exclusion (Superdex S200, GE Healthcare) in 100 mM sodium acetate pH 5.0-5.8. Samples of labeled proteins were also incubated with 5 mM iron(II) chloride for 1 h at room temperature to prove that DOTA-molecules are available for coupling with radioisotopes. After the incubation unbound iron was removed using a HiTrap Desalting column (GE Healthcare). MALDI-TOF analysis was used to determine the degree of labeling.

Example 9: Matrix-Assisted Laser Desorption/Ionization Mass Spectrometry (MALDI-TOF) Mass Spectrometry to Confirm Homogeneously Labeling of Fusion Proteins Matrix-assisted laser desorption/ionization mass spectrometry (MALDI-TOF MS) was carried out as followed:

Fusion proteins were purified and concentrated using C18-P10-ZipTips (Millipore; catalog number ZTC18S096). The tips were washed with 0.1% (v/v) trifluoroacedic acid (TFA) in water and eluted with 50% (v/v) acetonitrile/0.1% TFA. Samples were treated with 2% (v/v) TFA in water and embedded in 2,5-dihydroxyacetophenone (DHAP) matrix (Bruker, catalog number 8231829). The mass of fusion proteins was measured on an AUTOFLEX™ speed mass spectrometer (Bruker). Protein calibration standards (Bruker, part no. 8206355 and part no. 8207234) were used for tuning of the autoflex speed mass spectrometer.

Fusion proteins with and without EDANS label were analyzed by MALDI-TOF mass spectra and peaks were compared. Results are shown in FIG. 4 and confirm that the fusion proteins are homogeneously labelled with 2 or 4 or 6 dye molecules. MALDI-TOF analysis shows that fusion proteins 140350 and 140353 are labeled with 6 dye molecules, corresponding to 6 cysteines in the fusion protein.

Fusion proteins with and without DOTA label were analyzed by MALDI-TOF mass spectra and peaks were compared. The analysis confirms that the fusion proteins are homogeneously labeled with 2 Maleimide-DOTA molecules. MALDI-TOF analysis also shows that the DOTA molecules labeled to the fusion proteins with two coupling sites are available for coupling with iron(II)chloride molecules. Although the $K_D$ is slightly altered after labeling of the fusion proteins, labeling does not significantly affect the affinity of the fusion proteins to the target. Results are summarized in Table 4 (n.d., not determined).

TABLE 4

Affinity analysis of labelled fusion proteins using SPR

| Clone number | label | Number of label | $Mr_{calc}$ | $Mr_{exp}$ | target affinity $K_D$ |
|---|---|---|---|---|---|
| 146414 | none | 0 | 25592 Da | 25583 Da | 0.79 nM |
|  | EDANS | 2 | 26288 Da | 26278 Da | 0.84 nM |
| 146416 | none | 0 | 33894 Da | 33877 Da | 0.79 nM |
|  | EDANS | 4 | 35286 Da | 35283 Da | 1.17 nM |
| 146418 | none | 0 | 42120 Da | 42133 Da | 0.92 nM |
|  | EDANS | 4 | 43512 Da | 43527 Da | 1.19 nM |
| 143276 | none | 0 | 30526 Da | 30527 Da | 26 nM |
|  | EDANS | 2 | 31216 Da | 31216 Da | n.d. |

The invention claimed is:

1. A targeted compound for specific coupling of chemical moieties, the targeted compound comprising:
   (a) a targeting domain selected from the group consisting of a non-Immunoglobulin protein, an antibody, and an antibody fragment, wherein the non-Immunoglobulin protein, antibody, or antibody fragment is capable of binding a target with a binding constant $K_D$ of 500 nM or less;
   (b) one or more linking moieties consisting of 10 to 80 amino acids consisting essentially of or comprising 20 to 60% alanine, 20 to 40% proline, and 10 to 60% serine, wherein:
   (i) each of the one or more linking moieties comprises an amino acid sequence at least 85% identical to any of SEQ ID NOs: 3-34 and 55-76; and
   (ii) no more than 5 consecutive amino acids are identical; and
   (c) one or more coupling sites at the C-terminal or N-terminal end of at least one linking moiety, wherein the coupling site consists of a single cysteine or is a cysteine-rich peptide motif selected from the group consisting of CXC, CXXC (SEQ ID NO: 35), and CXXXC (SEQ ID NO: 81), wherein each X is independently selected from the group consisting of proline, alanine, serine, valine, glycine, threonine, asparagine, aspartic acid, glutamine, glutamic acid, lysine, histidine, and arginine, and further wherein at least one of the one or more linking moieties connects the targeting domain and at least one of the one or more coupling sites and/or wherein at least one of the one or more linking moieties connects two coupling sites.

2. The targeted compound of claim 1, wherein the targeting domain is a non-Immunoglobulin protein selected from the group consisting of a ubiquitin mutein, a mutein of a domain of protein A, an ankyrin repeat protein mutein, a lipocalin mutein, a mutein of a human Fyn SH3 domain, a mutein of a human fibronectin tenth domain, a mutein of an FN3 domain, a mutein of a Kunitz domain, a Sac7d mutein, a chagasin mutein, a mutein of a multimerized low density lipoprotein receptor-A, a mutein of a cysteine-knot miniprotein, a mutein of an Armadillo-repeat protein, a mutein of a tetranectin, a mutein of a C-type lectin domain, and a mutein of CTLA4.

3. The targeted compound of claim 2, wherein the non-Immunoglobulin protein comprises a ubiquitin mutein that is 80-94% identical to the ubiquitin of SEQ ID NO: 1.

4. The targeted compound of claim 1, wherein the targeting domain is an antibody fragment.

5. The targeted compound of claim 1, wherein the targeted compound further comprises an additional cap comprising an amino acid sequence of 10 to 80 amino acids immediately C-terminal to the most C-terminally located coupling site.

6. The targeted compound of claim 5, wherein the 10 to 80 amino acids are selected from the group consisting of alanine, proline, serine, valine, leucine, methionine, isoleucine, lysine, arginine, glutamic acid, aspartic acid, threonine, glutamine, glycine, asparagine, and histidine.

7. The targeted compound of claim 1, wherein at least one coupling site is located C-terminal to at least one linking moiety.

8. The targeted compound of claim 1, wherein the chemical moieties are selected from the group consisting of drugs, toxins, dyes, small molecules, and chelators.

9. The targeted compound of claim 8, wherein at least one of the chemical moieties is a chelator designed as a complexing agent for coupling one or more further moieties to the targeted compound.

10. The targeted compound of claim 9, wherein the chelator is a complexing agent for coupling one or more radioisotopes to the targeted compound.

11. A method for diagnosing or treating a cancer, the method comprising contacting a cancer cell present in and/or isolated from a subject with the targeted compound of claim 1 conjugated to a chemical moeity selected from the group consisting of a diagnostic agent and a therapeutic agent, wherein the targeting domain binds to a cancer antigen present on and/or in the cancer cell to deliver the chemical moiety to the cancer cell to thereby diagnose or treat the cancer.

12. The method of claim 11, wherein the contacting is performed in vitro.

13. A targeted compound for specific coupling of chemical moieties, the targeted compound comprising:

(a) a targeting domain selected from the group consisting of a non-Immunoglobulin protein, an antibody, and an antibody fragment, wherein the non-Immunoglobulin protein, antibody, or antibody fragment is capable of binding a target with a binding constant $K_D$ of 500 nM or less;

(b) one or more linking moieties consisting of 10 to 80 amino acids consisting essentially of or comprising 20 to 60% alanine, 20 to 40% proline, and 10 to 60% serine, wherein:

(i) each of the one or more linking moieties comprises an amino acid sequence at least 85% identical to any of SEQ ID NOs: 3-34 and 55-76; and (ii) no more than 5 consecutive amino acids are identical; and (c) one or more coupling sites at the C-terminal or N-terminal end of at least one linking moiety, wherein:

(i) the coupling site consists of a single cysteine or is a cysteine-rich peptide motif selected from the group consisting of CXC, CXXC (SEQ ID NO: 35), and CXXXC (SEQ ID NO: 81), wherein each X is independently selected from the group consisting of proline, alanine, serine, valine, glycine, threonine, asparagine, aspartic acid, glutamine, glutamic acid, lysine, histidine, and arginine;

(ii) at least one of the one or more linking moieties connects the targeting domain and at least one of the one or more coupling sites and/or wherein at least one of the one or more linking moieties connects two coupling sites; and (iii) the targeted compound is a fusion protein that comprises or consists essentially of an amino acid sequence as set forth in any of SEQ ID NOs: 42-51.

* * * * *

SEQUENCE LISTING

<160> NUMBER OF SEQ ID NOS: 81

<210> SEQ ID NO 1
<211> LENGTH: 76
<212> TYPE: PRT
<213> ORGANISM: Artificial Sequence
<220> FEATURE:
<223> OTHER INFORMATION: Artificially synthesized ubiquitin

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 152
<212> TYPE: PRT
<213> ORGANISM: Artificial Sequence
<220> FEATURE:
<223> OTHER INFORMATION: Artificially synthesized bis-ubiquitin

<400> SEQUENCE: 2

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
            85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly
145                 150

<210> SEQ ID NO 3
<211> LENGTH: 49
<212> TYPE: PRT
<213> ORGANISM: Artificial Sequence
<220> FEATURE:
<223> OTHER INFORMATION: Artificially synthesized linker

<400> SEQUENCE: 3

Ser Ala Pro Ala Pro Ser Ala Pro Ala Ala Ser Ala Pro Pro Ala Pro
1               5                   10                  15

Ala Ala Pro Ala Ala Pro Ala Ala Pro Ala Ser Ala Pro Ala Pro Ala
            20                  25                  30

Pro Ala Pro Ala Ala Ser Pro Ser Pro Ala Ala Pro Ala Pro Ser Pro
        35                  40                  45

Ala

<210> SEQ ID NO 4
<211> LENGTH: 24
<212> TYPE: PRT
<213> ORGANISM: Artificial Sequence
<220> FEATURE:
<223> OTHER INFORMATION: Artificially synthesized linker

<400> SEQUENCE: 4

Pro Ala Pro Ala Ser Pro Ala Ser Ala Pro Ser Ala Pro Ala Ser Ala
1               5                   10                  15

Pro Pro Ala Ala Pro Ser Ala Ala
            20

<210> SEQ ID NO 5
<211> LENGTH: 24
<212> TYPE: PRT
<213> ORGANISM: Artificial Sequence
<220> FEATURE:
<223> OTHER INFORMATION: Artificially synthesized linker

<400> SEQUENCE: 5

Pro Ala Pro Ser Ala Pro Ala Pro Ala Ala Ser Pro Ala Ala Ala Pro
1               5                   10                  15

Ala Ser Ala Ala Pro Ala Ser Ala
            20

<210> SEQ ID NO 6
<211> LENGTH: 39
<212> TYPE: PRT
<213> ORGANISM: Artificial Sequence
<220> FEATURE:
<223> OTHER INFORMATION: Artificially synthesized linker

<400> SEQUENCE: 6

```
Ser Ala Pro Ala Pro Ser Ala Pro Ala Ser Ala Pro Pro Ala Pro
1               5                   10                  15

Ala Ala Pro Ala Ala Pro Ala Ala Pro Ala Ser Ala Pro Ala Pro Ala
            20                  25                  30

Pro Ala Pro Ala Pro Ala Ala
        35
```

<210> SEQ ID NO 7
<211> LENGTH: 49
<212> TYPE: PRT
<213> ORGANISM: Artificial Sequence
<220> FEATURE:
<223> OTHER INFORMATION: Artificially synthesized linker

<400> SEQUENCE: 7

```
Ala Ser Pro Ala Pro Ala Pro Ser Pro Ala Ser Pro Ala Pro Ala Ser
1               5                   10                  15

Pro Ala Ser Ala Pro Ser Ala Pro Ala Ser Ala Pro Pro Ala Ala Pro
            20                  25                  30

Ser Ala Ser Pro Ala Pro Ser Ala Pro Ala Pro Ala Ala Ala Ser Pro
        35                  40                  45

Ala
```

<210> SEQ ID NO 8
<211> LENGTH: 49
<212> TYPE: PRT
<213> ORGANISM: Artificial Sequence
<220> FEATURE:
<223> OTHER INFORMATION: Artificially synthesized linker

<400> SEQUENCE: 8

```
Ala Pro Ala Ser Ala Ala Pro Ala Ser Ala Ser Ala Pro Ala Pro Ser
1               5                   10                  15

Ala Pro Ala Ala Ser Ala Pro Pro Ala Pro Ala Ala Pro Ala Ala Pro
            20                  25                  30

Ala Ala Pro Ala Ser Ala Pro Ala Pro Ala Pro Ala Pro Ala Ala Ala
        35                  40                  45

Pro
```

<210> SEQ ID NO 9
<211> LENGTH: 39
<212> TYPE: PRT
<213> ORGANISM: Artificial Sequence
<220> FEATURE:
<223> OTHER INFORMATION: Artificially synthesized linker

<400> SEQUENCE: 9

```
Pro Ala Ala Pro Ala Pro Ser Pro Ser Ala Pro Ala Pro Ala Ser Pro
1               5                   10                  15

Ala Ser Ala Pro Ser Ala Pro Ala Ser Ala Pro Pro Ala Ala Pro Ser
            20                  25                  30

Ala Ala Ser Pro Ala Pro Ser
        35
```

<210> SEQ ID NO 10
<211> LENGTH: 20
<212> TYPE: PRT
<213> ORGANISM: Artificial Sequence
<220> FEATURE:
<223> OTHER INFORMATION: Artificially synthesized linker

<400> SEQUENCE: 10

```
Pro Ala Pro Ala Ser Ala Ser Pro Ala Ala Pro Ala Ser Ala Ala
1               5                   10                  15

Pro Ala Ser Ala
            20

<210> SEQ ID NO 11
<211> LENGTH: 59
<212> TYPE: PRT
<213> ORGANISM: Artificial Sequence
<220> FEATURE:
<223> OTHER INFORMATION: Artificially synthesized linker

<400> SEQUENCE: 11

Ser Ala Pro Ala Pro Ser Ala Pro Ala Ala Ser Ala Pro Pro Ala Pro
1               5                   10                  15

Ala Ala Pro Ala Ala Pro Ala Ala Pro Ala Ser Ala Pro Ala Pro Ala
                20                  25                  30

Pro Ala Pro Ala Ala Ala Pro Ser Pro Ala Ala Pro Ala Pro Ser Pro
            35                  40                  45

Ala Ser Pro Ala Pro Ala Ser Pro Ala Ser Ala
    50                  55

<210> SEQ ID NO 12
<211> LENGTH: 74
<212> TYPE: PRT
<213> ORGANISM: Artificial Sequence
<220> FEATURE:
<223> OTHER INFORMATION: Artificially synthesized linker

<400> SEQUENCE: 12

Ala Ser Pro Ser Ala Pro Ala Pro Pro Ala Ala Pro Ser Ala Ala Ser
1               5                   10                  15

Pro Ala Pro Ser Ala Pro Ala Pro Ala Ala Ser Pro Ala Ala Ala
                20                  25                  30

Pro Ser Ala Ala Pro Ala Ser Ala Ser Ala Pro Ala Pro Ser Ala Pro
            35                  40                  45

Ala Ala Pro Pro Ala Pro Ala Ala Pro Ala Ala Pro Ala Ala Pro Ala
    50                  55                  60

Ser Ala Pro Ala Pro Ala Pro Ala Pro Ala
65                  70

<210> SEQ ID NO 13
<211> LENGTH: 74
<212> TYPE: PRT
<213> ORGANISM: Artificial Sequence
<220> FEATURE:
<223> OTHER INFORMATION: Artificially synthesized linker

<400> SEQUENCE: 13

Ala Pro Ser Pro Ala Ala Pro Ala Pro Ser Pro Ala Ser Ala Ala Ala
1               5                   10                  15

Pro Ala Pro Ala Ser Pro Ala Ser Ala Pro Ser Ala Pro Ala Ser Ala
                20                  25                  30

Pro Pro Ala Ala Pro Ser Ala Ala Ser Pro Ala Pro Ser Ala Pro Ala
            35                  40                  45

Pro Ala Ser Ala Ser Pro Ala Ala Ala Pro Ser Ala Ala Pro Ala Ala
    50                  55                  60

Ser Ala Ser Ala Pro Ala Pro Ser Pro Ala
65                  70
```

<210> SEQ ID NO 14
<211> LENGTH: 59
<212> TYPE: PRT
<213> ORGANISM: Artificial Sequence
<220> FEATURE:
<223> OTHER INFORMATION: Artificially synthesized linker

<400> SEQUENCE: 14

Ala Pro Ser Pro Ala Pro Ala Ala Pro Ala Ala Pro Ala Ser Ala Ala
1               5                   10                  15

Ala Pro Ala Ser Ala Pro Ala Pro Ala Pro Ala Pro Ala Ala Ala Pro
                20                  25                  30

Ser Pro Ala Ala Pro Ala Pro Ser Pro Ala Ala Pro Ala Pro Ala Ser
            35                  40                  45

Pro Ala Ser Ala Pro Ser Ala Pro Ala Pro Ser
        50                  55

<210> SEQ ID NO 15
<211> LENGTH: 30
<212> TYPE: PRT
<213> ORGANISM: Artificial Sequence
<220> FEATURE:
<223> OTHER INFORMATION: Artificially synthesized linker

<400> SEQUENCE: 15

Ala Pro Ala Pro Ser Ala Ala Ser Pro Ala Pro Ser Ala Pro Ala Pro
1               5                   10                  15

Ala Ser Ala Ser Pro Ala Ala Ala Pro Ala Ser Ala Pro Ala
                20                  25                  30

<210> SEQ ID NO 16
<211> LENGTH: 10
<212> TYPE: PRT
<213> ORGANISM: Artificial Sequence
<220> FEATURE:
<223> OTHER INFORMATION: Artificially synthesized linker

<400> SEQUENCE: 16

Ala Ser Pro Ala Ser Ala Ala Pro Ala Ala
1               5                   10

<210> SEQ ID NO 17
<211> LENGTH: 26
<212> TYPE: PRT
<213> ORGANISM: Artificial Sequence
<220> FEATURE:
<223> OTHER INFORMATION: Artificially synthesized linker

<400> SEQUENCE: 17

Ala Pro Ala Pro Ala Ser Ala Pro Ala Ala Pro Ala Pro Ser Pro Ala Ala
1               5                   10                  15

Pro Ala Pro Ser Pro Ala Pro Ala Pro Ala
                20                  25

<210> SEQ ID NO 18
<211> LENGTH: 28
<212> TYPE: PRT
<213> ORGANISM: Artificial Sequence
<220> FEATURE:
<223> OTHER INFORMATION: Artificially synthesized linker

<400> SEQUENCE: 18

Ala Pro Ser Ala Pro Ala Ser Ala Ser Pro Pro Ser Ala Pro Ser Ala
1               5                   10                  15

Ser Ala Ala Ser Ser Ala Ser Ala Pro Ala Ala Ala
            20                  25

<210> SEQ ID NO 19
<211> LENGTH: 22
<212> TYPE: PRT
<213> ORGANISM: Artificial Sequence
<220> FEATURE:
<223> OTHER INFORMATION: Artificially synthesized linker

<400> SEQUENCE: 19

Ala Pro Ala Ser Ala Ala Pro Ala Ser Ala Ser Ala Pro Ala Pro Ser
1               5                   10                  15

Ser Ala Pro Ala Ala Ser
            20

<210> SEQ ID NO 20
<211> LENGTH: 74
<212> TYPE: PRT
<213> ORGANISM: Artificial Sequence
<220> FEATURE:
<223> OTHER INFORMATION: Artificially synthesized linker

<400> SEQUENCE: 20

Ala Pro Ala Pro Ala Ser Pro Ala Ser Ala Pro Ser Ala Pro Ala Ser
1               5                   10                  15

Ala Pro Pro Ala Ala Pro Ser Ala Ala Ser Pro Ala Pro Ser Ala Pro
            20                  25                  30

Ala Pro Ala Ser Ala Ser Pro Ala Ala Ala Pro Ser Ala Ala Pro Ala
        35                  40                  45

Ala Ser Ala Ser Ala Pro Ala Pro Ser Ala Pro Ala Ala Pro Ser Pro
    50                  55                  60

Ala Pro Ala Ala Pro Ala Ala Pro Ala Ser
65                  70

<210> SEQ ID NO 21
<211> LENGTH: 75
<212> TYPE: PRT
<213> ORGANISM: Artificial Sequence
<220> FEATURE:
<223> OTHER INFORMATION: Artificially synthesized linker

<400> SEQUENCE: 21

Ala Ala Pro Ala Ser Ala Pro Ala Pro Ala Pro Ala Pro Ala Ala Ala
1               5                   10                  15

Pro Ser Pro Ala Ala Pro Ala Pro Ser Pro Ala Ala Pro Ala Pro Ala
            20                  25                  30

Ser Pro Ala Ser Ala Pro Ser Ala Pro Ala Ser Ala Pro Pro Ala Ala
        35                  40                  45

Pro Ser Ala Ala Ser Pro Ala Pro Ser Ala Pro Ala Pro Ala Ser Ala
    50                  55                  60

Ser Pro Ala Ala Ala Pro Ala Ser Ala Pro Ala
65                  70                  75

<210> SEQ ID NO 22
<211> LENGTH: 49
<212> TYPE: PRT
<213> ORGANISM: Artificial Sequence
<220> FEATURE:
<223> OTHER INFORMATION: Artificially synthesized linker

<400> SEQUENCE: 22

Ser Ala Pro Ala Pro Ser Ala Pro Ala Ala Ser Ala Pro Pro Ala Pro
1               5                   10                  15

Ala Ala Pro Ala Ala Pro Ala Ala Pro Ala Ser Ala Pro Ala Pro Ala
                20                  25                  30

Pro Ala Pro Ala Ala Ala Pro Ser Pro Ala Ala Pro Ala Pro Ser Pro
            35                  40                  45

Ala

<210> SEQ ID NO 23
<211> LENGTH: 50
<212> TYPE: PRT
<213> ORGANISM: Artificial Sequence
<220> FEATURE:
<223> OTHER INFORMATION: Artificially synthesized linker

<400> SEQUENCE: 23

Pro Ala Pro Ala Ser Pro Ala Ser Ala Pro Ser Ala Pro Ala Ser Ala
1               5                   10                  15

Pro Pro Ala Ala Pro Ser Ala Ala Ser Pro Ala Pro Ser Ala Pro Ala
                20                  25                  30

Pro Ala Ser Ala Ser Pro Ala Ala Ala Pro Ala Ser Ala Ala Pro Ala
            35                  40                  45

Ser Ala
    50

<210> SEQ ID NO 24
<211> LENGTH: 21
<212> TYPE: PRT
<213> ORGANISM: Artificial Sequence
<220> FEATURE:
<223> OTHER INFORMATION: Artificially synthesized linker

<400> SEQUENCE: 24

Ser Ala Pro Ala Pro Ser Ala Pro Ala Ala Ser Ala Pro Pro Ala Pro
1               5                   10                  15

Ala Ala Pro Ala Ala
                20

<210> SEQ ID NO 25
<211> LENGTH: 46
<212> TYPE: PRT
<213> ORGANISM: Artificial Sequence
<220> FEATURE:
<223> OTHER INFORMATION: Artificially synthesized linker

<400> SEQUENCE: 25

Ser Ala Pro Ser Ala Pro Ala Ala Ser Ala Pro Pro Ala Pro Ala Ala
1               5                   10                  15

Pro Ala Ala Pro Ala Pro Ala Ser Ala Pro Ala Pro Ala Pro Ala Pro
                20                  25                  30

Ala Ala Pro Ser Pro Ala Ala Pro Ala Pro Ser Pro Ala Ala
            35                  40                  45

<210> SEQ ID NO 26
<211> LENGTH: 47
<212> TYPE: PRT
<213> ORGANISM: Artificial Sequence
<220> FEATURE:
<223> OTHER INFORMATION: Artificially synthesized linker

<400> SEQUENCE: 26

Ala Ser Pro Ala Pro Ser Ala Pro Ser Ala Pro Ser Ala Pro
1               5                   10                  15

Pro Ala Ala Pro Ser Ala Ser Pro Ala Pro Ser Ala Pro Ala Pro
                20                  25                  30

Ala Ser Ala Ser Pro Ala Ala Pro Ala Ser Ala Pro Ser Ala
        35                  40                  45

<210> SEQ ID NO 27
<211> LENGTH: 46
<212> TYPE: PRT
<213> ORGANISM: Artificial Sequence
<220> FEATURE:
<223> OTHER INFORMATION: Artificially synthesized linker

<400> SEQUENCE: 27

Ala Ser Pro Ser Ala Pro Ser Ala Pro Ser Pro Ala Pro Ala Ala
1               5                   10                  15

Pro Ala Ala Pro Ala Pro Ala Ala Pro Ala Pro Ala Pro Ala Pro
                20                  25                  30

Ala Ala Pro Ser Pro Ala Ala Pro Ala Pro Ser Pro Ala Ala
        35                  40                  45

<210> SEQ ID NO 28
<211> LENGTH: 47
<212> TYPE: PRT
<213> ORGANISM: Artificial Sequence
<220> FEATURE:
<223> OTHER INFORMATION: Artificially synthesized linker

<400> SEQUENCE: 28

Ala Ser Pro Ala Pro Ser Ala Ala Pro Ser Ala Pro Ala Ser Ala Pro
1               5                   10                  15

Pro Ala Ala Pro Ser Ala Ala Ala Pro Ala Pro Ser Pro Ala Pro Ala
                20                  25                  30

Pro Ala Ser Ala Ala Pro Ala Ala Pro Ala Ser Ala Pro Ser Ala
        35                  40                  45

<210> SEQ ID NO 29
<211> LENGTH: 46
<212> TYPE: PRT
<213> ORGANISM: Artificial Sequence
<220> FEATURE:
<223> OTHER INFORMATION: Artificially synthesized linker

<400> SEQUENCE: 29

Ser Ala Pro Ser Ala Pro Ala Pro Ser Pro Ala Pro Ala Ala
1               5                   10                  15

Pro Ala Ala Pro Ala Pro Ala Ser Ala Pro Ala Pro Ala Pro Ala Pro
                20                  25                  30

Ala Ala Pro Ser Pro Ala Ala Pro Ala Pro Ser Pro Ala Ala
        35                  40                  45

<210> SEQ ID NO 30
<211> LENGTH: 47
<212> TYPE: PRT
<213> ORGANISM: Artificial Sequence
<220> FEATURE:
<223> OTHER INFORMATION: Artificially synthesized linker

<400> SEQUENCE: 30

Ala Ser Pro Ala Pro Ala Ser Ala Pro Ser Ala Pro Ala Ser Ala Pro
1               5                   10                  15

Pro Ala Ala Pro Ser Ala Ala Ser Pro Ala Pro Ala
            20                  25                  30

Pro Ala Ser Ala Ser Pro Ala Ala Pro Ala Ser Ala Pro Ser Ala
        35                  40                  45

<210> SEQ ID NO 31
<211> LENGTH: 46
<212> TYPE: PRT
<213> ORGANISM: Artificial Sequence
<220> FEATURE:
<223> OTHER INFORMATION: Artificially synthesized linker

<400> SEQUENCE: 31

Ser Ala Pro Ser Ala Pro Ala Ala Pro Ser Pro Pro Ala Pro Ala Ala
1               5                   10                  15

Pro Ala Ala Pro Ala Pro Ala Ala Ala Pro Ala Pro Ala Pro Ala Pro
            20                  25                  30

Ala Ala Pro Ser Pro Ala Ala Pro Ala Pro Ser Pro Ala Ala
        35                  40                  45

<210> SEQ ID NO 32
<211> LENGTH: 47
<212> TYPE: PRT
<213> ORGANISM: Artificial Sequence
<220> FEATURE:
<223> OTHER INFORMATION: Artificially synthesized linker

<400> SEQUENCE: 32

Ala Ser Pro Ala Pro Ala Ala Ala Pro Ser Ala Pro Ala Ser Ala Pro
1               5                   10                  15

Pro Ala Ala Pro Ser Ala Ala Pro Ala Pro Ser Pro Ala Pro Ala
            20                  25                  30

Pro Ala Ser Ala Ala Pro Ala Ala Pro Ser Ala Pro Ser Ala
        35                  40                  45

<210> SEQ ID NO 33
<211> LENGTH: 24
<212> TYPE: PRT
<213> ORGANISM: Artificial Sequence
<220> FEATURE:
<223> OTHER INFORMATION: Artificially synthesized linker

<400> SEQUENCE: 33

Ser Ala Pro Ala Pro Ser Ser Ala Pro Ala Ser Pro Pro Ala
1               5                   10                  15

Ala Ala Ser Ala Ala Pro Ala Ala
            20

<210> SEQ ID NO 34
<211> LENGTH: 10
<212> TYPE: PRT
<213> ORGANISM: Artificial Sequence
<220> FEATURE:
<223> OTHER INFORMATION: Artificially synthesized linker

<400> SEQUENCE: 34

Ala Pro Ala Ser Ala Ala Pro Ala Ser Ala
1               5                   10

<210> SEQ ID NO 35
<211> LENGTH: 4
<212> TYPE: PRT
<213> ORGANISM: Artificial Sequence
<220> FEATURE:

```
<223> OTHER INFORMATION: Artificially synthesized coupling site
<220> FEATURE:
<221> NAME/KEY: variant
<222> LOCATION: (2)..(3)
<223> OTHER INFORMATION: Xaa can be any amino acid selected from Pro,
      Ala, Ser, Val, Gly, Thr, Ser, Asn , Asp, Gln, Glu, Lys, Arg, His

<400> SEQUENCE: 35

Cys Xaa Xaa Cys
1

<210> SEQ ID NO 36
<211> LENGTH: 4
<212> TYPE: PRT
<213> ORGANISM: Artificial Sequence
<220> FEATURE:
<223> OTHER INFORMATION: Artificially synthesized coupling site

<400> SEQUENCE: 36

Cys Pro Ala Cys
1

<210> SEQ ID NO 37
<211> LENGTH: 4
<212> TYPE: PRT
<213> ORGANISM: Artificial Sequence
<220> FEATURE:
<223> OTHER INFORMATION: Artificially synthesized coupling site

<400> SEQUENCE: 37

Cys Ser Ser Cys
1

<210> SEQ ID NO 38
<211> LENGTH: 4
<212> TYPE: PRT
<213> ORGANISM: Artificial Sequence
<220> FEATURE:
<223> OTHER INFORMATION: coupling site

<400> SEQUENCE: 38

Cys Ala Ala Cys
1

<210> SEQ ID NO 39
<211> LENGTH: 4
<212> TYPE: PRT
<213> ORGANISM: Artificial Sequence
<220> FEATURE:
<223> OTHER INFORMATION: Artificially synthesized coupling site

<400> SEQUENCE: 39

Cys Ala Ser Cys
1

<210> SEQ ID NO 40
<211> LENGTH: 152
<212> TYPE: PRT
<213> ORGANISM: Artificial Sequence
<220> FEATURE:
<223> OTHER INFORMATION: Artificially synthesized Her2-specific Affilin
      142628

<400> SEQUENCE: 40

Met Gln Ile Phe Val Lys Thr Leu Thr Gly Lys Thr Ile Thr Leu Glu
1               5                   10                  15

Val Glu Pro Ser Asp Thr Thr Glu Asn Val Lys Ala Lys Ile Gln Asp
```

```
            20                  25                  30
Lys Glu Gly Ile Pro Pro Asp Gln Gln Thr Leu Ala Phe Val Gly Lys
            35                  40                  45

Gln Leu Glu Asp Gly Arg Thr Leu Ser Asp Tyr Asn Ile Gln Lys Glu
        50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Asp Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala
145                 150

<210> SEQ ID NO 41
<211> LENGTH: 82
<212> TYPE: PRT
<213> ORGANISM: Artificial Sequence
<220> FEATURE:
<223> OTHER INFORMATION: Artificially synthesized EGFR-specific Affilin
      139891

<400> SEQUENCE: 41

Met Gln Ile Phe Val Lys Thr Leu Thr Tyr Asn Pro Met Arg Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg Asn Pro Asp Ile Leu His Leu Val Leu Arg Leu Arg
65                  70                  75                  80

Ala Ala

<210> SEQ ID NO 42
<211> LENGTH: 182
<212> TYPE: PRT
<213> ORGANISM: Artificial Sequence
<220> FEATURE:
<223> OTHER INFORMATION: Artificially synthesized EGFR specific fusion
      protein 143276

<400> SEQUENCE: 42

Met Gln Ile Phe Val Lys Thr Leu Thr Tyr Asn Pro Met Arg Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg Asn Pro Asp Ile Leu His Leu Val Leu Arg Leu Arg
65                  70                  75                  80
```

```
Ala Ala Ser Ala Pro Ala Pro Ser Ala Pro Ala Ala Ser Ala Pro Pro
                85                  90                  95

Ala Pro Ala Ala Pro Ala Ala Pro Ala Ala Pro Ala Ser Ala Pro Ala
            100                 105                 110

Pro Ala Pro Ala Pro Ala Ala Ser Pro Ser Pro Ala Ala Pro Ala Pro
            115                 120                 125

Ser Pro Ala Cys Pro Ala Pro Ala Ser Pro Ala Ser Ala Pro Ser Ala
130                 135                 140

Pro Ala Ser Ala Pro Pro Ala Ala Pro Ser Ala Ala Cys Ser Pro Ala
145                 150                 155                 160

Pro Ser Ala Pro Ala Pro Ala Ala Ser Pro Ala Ala Ala Pro Ala Ser
            165                 170                 175

Ala Ala Pro Ala Ser Ala
            180
```

<210> SEQ ID NO 43
<211> LENGTH: 252
<212> TYPE: PRT
<213> ORGANISM: Artificial Sequence
<220> FEATURE:
<223> OTHER INFORMATION: Artificially synthesized Her2 specific fusion protein 146414

<400> SEQUENCE: 43

```
Met Gln Ile Phe Val Lys Thr Leu Thr Gly Lys Thr Ile Thr Leu Glu
1               5                   10                  15

Val Glu Pro Ser Asp Thr Thr Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Asp Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Ser Glu Trp Ala Ile Leu His
130                 135                 140

Leu Val Leu Arg Leu Arg Ala Ala Ser Ala Pro Ala Pro Ser Ala Pro
145                 150                 155                 160

Ala Ala Ser Ala Pro Pro Ala Pro Ala Ala Pro Ala Ala Pro Ala Ala
            165                 170                 175

Pro Ala Ser Ala Pro Ala Pro Ala Pro Ala Ala Ser Pro Ser
            180                 185                 190

Pro Ala Ala Pro Ala Pro Ser Pro Ala Cys Pro Ala Pro Ala Ser Pro
            195                 200                 205

Ala Ser Ala Pro Ser Ala Pro Ala Ser Pro Ala Pro Ala Ala Pro Ser
            210                 215                 220

Ala Ala Cys Ser Pro Ala Pro Ser Ala Pro Ala Pro Ala Ala Ser Pro
225                 230                 235                 240

Ala Ala Ala Pro Ala Ser Ala Ala Pro Ala Ser Ala
```

245         250

<210> SEQ ID NO 44
<211> LENGTH: 352
<212> TYPE: PRT
<213> ORGANISM: Artificial Sequence
<220> FEATURE:
<223> OTHER INFORMATION: Artificially synthesized Her2 specific fusion
      protein 146416

<400> SEQUENCE: 44

Met Gln Ile Phe Val Lys Thr Leu Thr Gly Lys Thr Ile Thr Leu Glu
1               5                   10                  15

Val Glu Pro Ser Asp Thr Thr Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Asp Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala Ser Ala Pro Ala Pro Ser Ala Pro
145                 150                 155                 160

Ala Ala Ser Ala Pro Pro Ala Pro Ala Ala Pro Ala Pro Ala Ala Pro
                165                 170                 175

Pro Ala Ser Ala Pro Ala Pro Ala Pro Ala Pro Ala Pro Ala Ala Cys
            180                 185                 190

Ala Ser Pro Ala Pro Ala Pro Ser Pro Ala Ser Pro Ala Pro Ala Ser
        195                 200                 205

Pro Ala Ser Ala Pro Ser Ala Pro Ala Ser Pro Pro Ala Ala Pro
    210                 215                 220

Ser Ala Ser Pro Ala Pro Ser Ala Pro Ala Ala Ala Ser Pro
225                 230                 235                 240

Ala Cys Ala Pro Ala Ser Ala Ala Pro Ala Ser Ala Ser Ala Pro Ala
                245                 250                 255

Pro Ser Ala Pro Ala Ala Ser Ala Pro Pro Ala Pro Ala Ala Pro Ala
            260                 265                 270

Ala Pro Ala Ala Pro Ala Ser Ala Pro Ala Pro Ala Pro Ala
        275                 280                 285

Ala Ala Pro Cys Pro Ala Ala Pro Ala Pro Ser Pro Ser Ala Pro Ala
    290                 295                 300

Pro Ala Ser Pro Ala Ser Ala Pro Ser Ala Pro Ala Ser Ala Pro Pro
305                 310                 315                 320

Ala Ala Pro Ser Ala Ala Ser Pro Ala Pro Ser Cys Pro Ala Pro Ala
                325                 330                 335

Ser Ala Ser Pro Ala Ala Pro Ala Ser Ala Ala Pro Ala Ser Ala
        340                 345                 350

<210> SEQ ID NO 45
<211> LENGTH: 452
<212> TYPE: PRT
<213> ORGANISM: Artificial Sequence
<220> FEATURE:
<223> OTHER INFORMATION: Artificially synthesized Her2 specific fusion protein 146418

<400> SEQUENCE: 45

```
Met Gln Ile Phe Val Lys Thr Leu Thr Gly Lys Thr Ile Thr Leu Glu
1               5                   10                  15

Val Glu Pro Ser Asp Thr Thr Glu Asn Val Lys Ala Lys Ile Gln Asp
            20                  25                  30

Lys Glu Gly Ile Pro Pro Asp Gln Gln Thr Leu Ala Phe Val Gly Lys
        35                  40                  45

Gln Leu Glu Asp Gly Arg Thr Leu Ser Asp Tyr Asn Ile Gln Lys Glu
    50                  55                  60

Ser Thr Leu Trp Leu Tyr Leu Thr Trp Tyr Ala Ala Met Arg Ile Phe
65                  70                  75                  80

Val Thr Thr His Thr Gly Lys Thr Ile Thr Leu Asp Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Ser Glu Trp Ala Ile Leu His
    130                 135                 140

Leu Val Leu Arg Leu Arg Ala Ala Ser Ala Pro Ala Pro Ser Ala Pro
145                 150                 155                 160

Ala Ala Ser Ala Pro Pro Ala Pro Ala Ala Pro Ala Ala Pro Ala Ala
                165                 170                 175

Pro Ala Ser Ala Pro Ala Pro Ala Pro Ala Ala Ala Pro Ser
                180                 185                 190

Pro Ala Ala Pro Ala Pro Ser Pro Ala Ser Pro Ala Pro Ala Ser Pro
        195                 200                 205

Ala Ser Ala Cys Ala Ser Pro Ser Ala Pro Ala Pro Pro Ala Ala Pro
    210                 215                 220

Ser Ala Ala Ser Pro Ala Pro Ser Ala Pro Ala Ala Ala Ser
225                 230                 235                 240

Pro Ala Ala Ala Pro Ser Ala Ala Pro Ala Ser Ala Ser Ala Pro Ala
                245                 250                 255

Pro Ser Ala Pro Ala Ala Pro Pro Ala Pro Ala Ala Pro Ala Ala Pro
        260                 265                 270

Ala Ala Pro Ala Ser Ala Pro Ala Pro Ala Pro Ala Cys Ala
    275                 280                 285

Pro Ser Pro Ala Ala Pro Ala Pro Ser Pro Ala Ser Ala Ala Ala Pro
290                 295                 300

Ala Pro Ala Ser Pro Ala Ser Ala Pro Ser Ala Pro Ala Ser Ala Pro
305                 310                 315                 320

Pro Ala Ala Pro Ser Ala Ala Ser Pro Ala Pro Ser Ala Pro Ala Pro
            325                 330                 335

Ala Ser Ala Ser Pro Ala Ala Ala Pro Ser Ala Ala Pro Ala Ala Ser
        340                 345                 350

Ala Ser Ala Pro Ala Pro Ser Pro Ala Cys Ala Pro Ser Pro Ala Pro
    355                 360                 365
```

```
Ala Ala Pro Ala Ala Pro Ala Ser Ala Ala Pro Ala Ser Ala Pro
        370                 375                 380

Ala Pro Ala Pro Ala Pro Ala Ala Ala Pro Ser Pro Ala Ala Pro Ala
385                 390                 395                 400

Pro Ser Pro Ala Ala Pro Ala Pro Ala Ser Pro Ala Ser Ala Pro Ser
                405                 410                 415

Ala Pro Ala Pro Ser Cys Ala Pro Ala Pro Ser Ala Ala Ser Pro Ala
                420                 425                 430

Pro Ser Ala Pro Ala Pro Ala Ser Ala Ser Pro Ala Ala Ala Pro Ala
            435                 440                 445

Ser Ala Pro Ala
        450

<210> SEQ ID NO 46
<211> LENGTH: 282
<212> TYPE: PRT
<213> ORGANISM: Artificial Sequence
<220> FEATURE:
<223> OTHER INFORMATION: Artificially synthesized EGFR specific fusion
      protein 144646

<400> SEQUENCE: 46

Met Gln Ile Phe Val Lys Thr Leu Thr Tyr Asn Pro Met Arg Tyr Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
        50                  55                  60

Tyr Asn Ile Arg Asn Pro Asp Ile Leu His Leu Val Leu Arg Leu Arg
65                  70                  75                  80

Ala Ala Ser Ala Pro Ala Pro Ser Ala Pro Ala Ala Ser Ala Pro Pro
                85                  90                  95

Ala Pro Ala Ala Pro Ala Ala Pro Ala Ala Pro Ala Ser Ala Pro Ala
                100                 105                 110

Pro Ala Pro Ala Pro Ala Ala Ala Pro Ser Pro Ala Ala Pro Ala Pro
                115                 120                 125

Ser Pro Ala Ser Pro Ala Pro Ala Ser Pro Ala Ser Ala Pro Ser Ala
            130                 135                 140

Pro Ala Ser Ala Pro Pro Ala Ala Pro Ser Ala Ala Ser Pro Ala Pro
145                 150                 155                 160

Ser Ala Pro Ala Pro Ala Ala Ala Ser Pro Ala Ala Ala Pro Ala Ser
                165                 170                 175

Ala Ala Pro Ala Ser Cys Ser Ser Cys Ser Ala Pro Ser Ala Pro Ala
                180                 185                 190

Ala Pro Ser Pro Pro Ala Pro Ala Ala Pro Ala Ala Pro Ala Pro Ala
            195                 200                 205

Ala Ala Pro Ala Pro Ala Pro Ala Pro Ala Ala Pro Ser Pro Ala Ala
            210                 215                 220

Pro Ala Pro Ser Pro Ala Ala Cys Ser Ser Cys Ala Ser Pro Ala Pro
225                 230                 235                 240

Ala Ala Ala Pro Ser Ala Pro Ala Ser Ala Pro Pro Ala Ala Pro Ser
                245                 250                 255

Ala Ala Ala Pro Ala Pro Ser Pro Ala Pro Ala Pro Ala Ser Ala Ala
```

-continued

```
                    260                 265                 270
Pro Ala Ala Pro Ala Ser Ala Pro Ser Ala
            275                 280

<210> SEQ ID NO 47
<211> LENGTH: 311
<212> TYPE: PRT
<213> ORGANISM: Artificial Sequence
<220> FEATURE:
<223> OTHER INFORMATION: Artificially synthesized EGFR specific fusion
      protein 144647

<400> SEQUENCE: 47

Met Gln Ile Phe Val Lys Thr Leu Thr Tyr Asn Pro Met Arg Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg Asn Pro Asp Ile Leu His Leu Val Leu Arg Leu Arg
65                  70                  75                  80

Ala Ala Ser Ala Pro Ala Pro Ser Ala Pro Ala Ala Ser Ala Pro Pro
                85                  90                  95

Ala Pro Ala Ala Pro Ala Ala Pro Ala Ala Pro Ala Ser Ala Pro Ala
            100                 105                 110

Pro Ala Pro Ala Pro Ala Ala Pro Ser Pro Ala Ala Pro Ala Pro Ala
        115                 120                 125

Ser Pro Ala Ser Pro Ala Pro Ala Ser Pro Ala Ser Ala Pro Ser Ala
    130                 135                 140

Pro Ala Ser Ala Pro Pro Ala Ala Pro Ser Ala Ala Ser Pro Ala Pro
145                 150                 155                 160

Ser Ala Pro Ala Pro Ala Ala Ser Pro Ala Ala Ala Pro Ala Pro Ser
                165                 170                 175

Ala Ala Pro Ala Ser Cys Pro Ala Cys Ser Ala Pro Ser Ala Pro Ala
            180                 185                 190

Ala Ser Ala Pro Pro Ala Pro Ala Ala Pro Ala Ala Pro Ala Pro Ala
        195                 200                 205

Ser Ala Pro Ala Pro Ala Pro Ala Pro Ala Ala Pro Ser Pro Ala Ala
    210                 215                 220

Pro Ala Pro Ser Pro Ala Ala Cys Pro Ala Cys Ala Ser Pro Ala Pro
225                 230                 235                 240

Ala Ser Ala Pro Ser Ala Pro Ala Ser Ala Pro Pro Ala Ala Pro Ser
                245                 250                 255

Ala Ala Ser Pro Ala Pro Ser Ala Pro Ala Pro Ala Ser Ala Ser Pro
            260                 265                 270

Ala Ala Ala Pro Ala Ser Ala Pro Ser Ala Glu Thr Val Arg Phe Gln
        275                 280                 285

Ser Gly Ser Ser His His His His His Ser Ser Gly Ser Ala Trp
    290                 295                 300

Ser His Pro Gln Phe Glu Lys
305                 310

<210> SEQ ID NO 48
<211> LENGTH: 282
```

```
<212> TYPE: PRT
<213> ORGANISM: Artificial Sequence
<220> FEATURE:
<223> OTHER INFORMATION: Artificially synthesized EGFR specific fusion
      protein 144648

<400> SEQUENCE: 48

Met Gln Ile Phe Val Lys Thr Leu Thr Tyr Asn Pro Met Arg Tyr Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Arg
        35                  40                  45

Leu Ile Trp Ala Gly Lys Gln Leu Glu Asp Gly Arg Thr Leu Ser Asp
    50                  55                  60

Tyr Asn Ile Arg Asn Pro Asp Ile Leu His Leu Val Leu Arg Leu Arg
65                  70                  75                  80

Ala Ala Ser Ala Pro Ala Pro Ser Ala Pro Ala Ala Ser Ala Pro Pro
                85                  90                  95

Ala Pro Ala Ala Pro Ala Ala Pro Ala Ala Pro Ala Ser Ala Pro Ala
            100                 105                 110

Pro Ala Pro Ala Pro Ala Ala Pro Ser Pro Ala Ala Pro Ala Pro
            115                 120                 125

Ser Pro Ala Ser Pro Ala Pro Ala Ser Pro Ala Ser Ala Pro Ser Ala
    130                 135                 140

Pro Ala Ser Ala Pro Pro Ala Ala Pro Ser Ala Ala Ser Pro Ala Pro
145                 150                 155                 160

Ser Ala Pro Ala Pro Ala Ala Ala Ser Pro Ala Ala Ala Pro Ala Ser
                165                 170                 175

Ala Ala Pro Ala Ser Cys Ala Ala Cys Ser Ala Pro Ser Ala Pro Ala
            180                 185                 190

Ala Pro Ser Pro Pro Ala Pro Ala Ala Pro Ala Ala Pro Ala Pro Ala
        195                 200                 205

Ser Ala Pro Ala Pro Ala Pro Ala Pro Ala Ala Pro Ser Pro Ala Ala
    210                 215                 220

Pro Ala Pro Ser Pro Ala Ala Cys Ala Ala Cys Ala Ser Pro Ala Pro
225                 230                 235                 240

Ala Ser Ala Pro Ser Ala Pro Ala Ser Ala Pro Pro Ala Ala Pro Ser
                245                 250                 255

Ala Ala Ser Pro Ala Pro Ser Pro Ala Pro Ala Pro Ala Ser Ala Ser
            260                 265                 270

Pro Ala Ala Pro Ala Ser Ala Pro Ser Ala
        275                 280

<210> SEQ ID NO 49
<211> LENGTH: 282
<212> TYPE: PRT
<213> ORGANISM: Artificial Sequence
<220> FEATURE:
<223> OTHER INFORMATION: Artificially synthesized EGFR specific fusion
      protein 144649

<400> SEQUENCE: 49

Met Gln Ile Phe Val Lys Thr Leu Thr Tyr Asn Pro Met Arg Tyr Gly
1               5                   10                  15

Lys Thr Ile Thr Leu Glu Val Glu Pro Ser Asp Thr Ile Glu Asn Val
            20                  25                  30
```

Lys Ala Lys Ile Gln Asp Lys Glu Gly Ile Pro Pro Asp Gln Gln Arg
            35                  40                  45

Leu Ile Trp Ala Gly Lys Gln Leu Glu Asp Gly Arg Thr Leu Ser Asp
 50                  55                  60

Tyr Asn Ile Arg Asn Pro Asp Ile Leu His Leu Val Leu Arg Leu Arg
 65                  70                  75                  80

Ala Ala Ser Ala Pro Ala Pro Ser Ala Pro Ala Ala Ser Ala Pro Pro
                 85                  90                  95

Ala Pro Ala Ala Pro Ala Ala Pro Ala Pro Ala Ser Ala Pro Ala
            100                 105                 110

Pro Ala Pro Ala Pro Ala Ala Pro Ser Pro Ala Ala Pro Ala Pro
            115                 120                 125

Ser Pro Ala Ser Pro Ala Pro Ala Ser Pro Ala Ser Ala Pro Ser Ala
130                 135                 140

Pro Ala Ser Ala Pro Pro Ala Pro Ser Ala Ser Pro Ala Pro
145                 150                 155                 160

Ser Ala Pro Ala Pro Ala Ala Ser Pro Ala Ala Pro Ala Ser
                 165                 170                 175

Ala Ala Pro Ala Ser Cys Ala Ser Cys Ala Ser Pro Ser Ala Pro Ser
            180                 185                 190

Ala Pro Ser Pro Pro Ala Pro Ala Ala Pro Ala Ala Pro Ala Pro Ala
            195                 200                 205

Ala Ala Pro Ala Pro Ala Pro Ala Ala Pro Ala Ala Pro Ser Pro Ala Ala
            210                 215                 220

Pro Ala Pro Ser Pro Ala Ala Cys Ala Ser Cys Ala Ser Pro Ala Pro
225                 230                 235                 240

Ser Ala Ala Pro Ser Ala Pro Ala Ser Ala Pro Pro Ala Ala Pro Ser
                 245                 250                 255

Ala Ala Ala Pro Ala Pro Ser Pro Ala Pro Ala Pro Ala Ser Ala Ala
            260                 265                 270

Pro Ala Ala Pro Ala Ser Ala Pro Ser Ala
            275                 280

<210> SEQ ID NO 50
<211> LENGTH: 182
<212> TYPE: PRT
<213> ORGANISM: Artificial Sequence
<220> FEATURE:
<223> OTHER INFORMATION: Artificially synthesized EGFR specific fusion
      protein 140153

<400> SEQUENCE: 50

Met Gln Ile Phe Val Arg Thr Leu Thr Tyr Asn Pro Met Arg Tyr Gly
 1               5                  10                  15

Arg Thr Ile Thr Leu Glu Val Glu Pro Ser Asp Thr Ile Glu Asn Val
                 20                  25                  30

Arg Ala Arg Ile Gln Asp Arg Glu Gly Ile Pro Pro Asp Gln Gln Arg
            35                  40                  45

Leu Ile Trp Ala Gly Arg Gln Leu Glu Asp Gly Arg Thr Leu Ser Asp
 50                  55                  60

Tyr Asn Ile Arg Asn Pro Asp Ile Leu His Leu Val Leu Arg Leu Arg
 65                  70                  75                  80

Ala Ala Ser Ala Pro Ala Pro Ser Ser Ala Pro Ala Ala Ser Ala Pro
                 85                  90                  95

Pro Ala Ala Ala Ser Ala Ala Pro Ala Ala Cys Pro Ala Cys Ala Pro
            100                 105                 110

```
Ala Pro Ala Ser Ala Pro Ala Ala Pro Ser Pro Ala Ala Pro Ala
        115                 120                 125

Pro Ser Pro Ala Pro Ala Pro Ala Cys Pro Ala Cys Ala Pro Ser Ala
130                 135                 140

Pro Ala Ser Ala Ser Pro Pro Ser Ala Pro Ser Ala Ser Ala Ala Ser
145                 150                 155                 160

Ser Ala Ser Ala Pro Ala Ala Cys Pro Ala Cys Ala Pro Ala Ser
                165                 170                 175

Ala Ala Pro Ala Ser Ala
            180

<210> SEQ ID NO 51
<211> LENGTH: 182
<212> TYPE: PRT
<213> ORGANISM: Artificial Sequence
<220> FEATURE:
<223> OTHER INFORMATION: Artificially synthesized EGFR specific fusion
      protein 140350

<400> SEQUENCE: 51

Met Gln Ile Phe Val Arg Thr Leu Thr Tyr Asn Pro Met Arg Tyr Gly
1               5                   10                  15

Arg Thr Ile Thr Leu Glu Val Glu Pro Ser Asp Thr Ile Glu Asn Val
            20                  25                  30

Arg Ala Arg Ile Gln Asp Arg Glu Gly Ile Pro Pro Asp Gln Gln Arg
        35                  40                  45

Leu Ile Trp Ala Gly Arg Gln Leu Glu Asp Gly Arg Thr Leu Ser Asp
50                  55                  60

Tyr Asn Ile Arg Asn Pro Asp Ile Leu His Leu Val Leu Arg Leu Arg
65                  70                  75                  80

Ala Ala Ser Ala Pro Ala Pro Ser Ser Ala Pro Ala Ala Ser Ala Pro
                85                  90                  95

Pro Ala Ala Ala Ser Ala Ala Pro Ala Ala Cys Pro Ala Cys Ala Pro
            100                 105                 110

Ala Pro Ala Ser Ala Pro Ala Ala Ala Pro Ser Pro Ala Ala Pro Ala
        115                 120                 125

Pro Ser Pro Ala Pro Ala Pro Ala Cys Pro Ala Cys Ala Pro Ser Ala
130                 135                 140

Pro Ala Ser Ala Ser Pro Pro Ser Ala Pro Ser Ala Ser Ala Ala Ser
145                 150                 155                 160

Ser Ala Ser Ala Pro Ala Ala Cys Pro Ala Cys Ala Pro Ala Ser
                165                 170                 175

Ala Ala Pro Ala Ser Ala
            180

<210> SEQ ID NO 52
<211> LENGTH: 175
<212> TYPE: PRT
<213> ORGANISM: Artificial Sequence
<220> FEATURE:
<223> OTHER INFORMATION: Artificially synthesized EGFR specific fusion
      protein 140353

<400> SEQUENCE: 52

Met Ala Ser Pro Ala Ser Ala Ala Pro Ala Ala Cys Pro Ala Cys Ala
1               5                   10                  15

Pro Ala Pro Ala Ser Ala Pro Ala Ala Ala Pro Ser Pro Ala Ala Pro
            20                  25                  30
```

```
Ala Pro Ser Pro Ala Pro Ala Pro Cys Pro Ala Cys Ala Pro Ser
        35                  40                  45
Ala Pro Ala Ser Ala Ser Pro Pro Ser Ala Pro Ser Ala Ser Ala Ala
    50                  55                  60
Ser Ser Ala Ser Ala Pro Ala Ala Cys Pro Ala Cys Ala Pro Ala
65                  70                  75                  80
Ser Ala Ala Pro Ala Ser Ala Ser Ala Pro Ala Pro Ser Ser Ala Pro
                85                  90                  95
Ala Ala Ser Met Gln Ile Phe Val Lys Thr Leu Thr Gly Lys Thr Ile
            100                 105                 110
Thr Leu Glu Val Glu Pro Ser Asp Thr Ile Glu Asn Val Lys Ala Lys
        115                 120                 125
Ile Gln Asp Lys Glu Gly Ile Pro Pro Asp Gln Gln Arg Leu Ile Phe
    130                 135                 140
Ala Gly Lys Gln Leu Glu Asp Gly Arg Thr Leu Ser Asp Tyr Asn Ile
145                 150                 155                 160
Gln Lys Glu Ser Thr Leu His Leu Val Leu Arg Leu Arg Ala Ala
                165                 170                 175

<210> SEQ ID NO 53
<211> LENGTH: 6
<212> TYPE: PRT
<213> ORGANISM: Artificial Sequence
<220> FEATURE:
<223> OTHER INFORMATION: Artificially synthesized histag

<400> SEQUENCE: 53

His His His His His His
1               5

<210> SEQ ID NO 54
<211> LENGTH: 10
<212> TYPE: PRT
<213> ORGANISM: Artificial Sequence
<220> FEATURE:
<223> OTHER INFORMATION: Artificially synthesized streptag

<400> SEQUENCE: 54

Ser Ala Trp Ser His Pro Gln Phe Glu Lys
1               5                   10

<210> SEQ ID NO 55
<211> LENGTH: 32
<212> TYPE: PRT
<213> ORGANISM: Artificial Sequence
<220> FEATURE:
<223> OTHER INFORMATION: Artificially synthesized linker

<400> SEQUENCE: 55

Ser Ala Pro Ala Pro Ser Ala Pro Ala Ala Ser Ala Pro Pro Ala Pro
1               5                   10                  15
Ala Ala Pro Ala Ala Pro Ala Ala Pro Ala Ser Ala Pro Ala Pro Ala
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Artificially synthesized linker

<400> SEQUENCE: 56
```

Ala Pro Ala Ala Ser Pro Ser Pro Ala Ala Pro Ala Pro Ser Pro Ala
1               5                   10                  15

Ser Pro Ala Pro Ala Ser Pro Ala Ser Ala Pro Ser Ala Pro Ala Ser
                20                  25                  30

<210> SEQ ID NO 57
<211> LENGTH: 34
<212> TYPE: PRT
<213> ORGANISM: Artificial Sequence
<220> FEATURE:
<223> OTHER INFORMATION: Artificially synthesized linker

<400> SEQUENCE: 57

Pro Pro Ala Ala Pro Ser Ala Ala Ser Ser Pro Ala Pro Ser Ala Pro
1               5                   10                  15

Ala Pro Ala Ala Ser Pro Ala Ala Ala Pro Ala Ser Ala Ala Pro Ala
                20                  25                  30

Ser Ala

<210> SEQ ID NO 58
<211> LENGTH: 19
<212> TYPE: PRT
<213> ORGANISM: Artificial Sequence
<220> FEATURE:
<223> OTHER INFORMATION: Artificially synthesized linker

<400> SEQUENCE: 58

Ser Ala Pro Ala Pro Ser Ala Pro Ala Ala Ser Ala Pro Pro Ala Pro
1               5                   10                  15

Ala Ala Pro

<210> SEQ ID NO 59
<211> LENGTH: 19
<212> TYPE: PRT
<213> ORGANISM: Artificial Sequence
<220> FEATURE:
<223> OTHER INFORMATION: Artificially synthesized linker

<400> SEQUENCE: 59

Ala Pro Ala Ala Pro Ala Ser Ala Pro Ala Pro Ala Ser Ala Pro Ala
1               5                   10                  15

Ala Ser Pro

<210> SEQ ID NO 60
<211> LENGTH: 21
<212> TYPE: PRT
<213> ORGANISM: Artificial Sequence
<220> FEATURE:
<223> OTHER INFORMATION: Artificially synthesized linker

<400> SEQUENCE: 60

Pro Ala Ala Pro Ala Pro Ser Pro Ala Ser Pro Ala Pro Ala Ser Pro
1               5                   10                  15

Ala Pro Ser Ser Ala
                20

<210> SEQ ID NO 61
<211> LENGTH: 40
<212> TYPE: PRT
<213> ORGANISM: Artificial Sequence
<220> FEATURE:
<223> OTHER INFORMATION: Artificially synthesized linker

```
-continued

<400> SEQUENCE: 61

Ser Ala Pro Ala Pro Ser Ala Pro Ala Ser Ala Pro Pro Ala Pro
1               5                   10                  15

Ala Ala Pro Ala Ala Pro Ala Pro Ala Ser Ala Pro Ala Pro Ala
                20                  25                  30

Pro Ala Pro Ala Ala Ser Pro Ser
            35                  40

<210> SEQ ID NO 62
<211> LENGTH: 40
<212> TYPE: PRT
<213> ORGANISM: Artificial Sequence
<220> FEATURE:
<223> OTHER INFORMATION: Artificially synthesized linker

<400> SEQUENCE: 62

Ser Ala Pro Ala Ala Ser Pro Ser Pro Ala Ala Pro Ala Pro Ser Pro
1               5                   10                  15

Ala Ser Pro Ala Pro Ala Ser Pro Ala Ser Ala Pro Ser Ala Pro Ala
                20                  25                  30

Ser Ala Pro Pro Ala Ala Ser Ala
            35                  40

<210> SEQ ID NO 63
<211> LENGTH: 20
<212> TYPE: PRT
<213> ORGANISM: Artificial Sequence
<220> FEATURE:
<223> OTHER INFORMATION: Artificially synthesized linker

<400> SEQUENCE: 63

Pro Ala Ala Pro Ala Pro Ser Pro Ala Ser Pro Ala Pro Ala Ser Pro
1               5                   10                  15

Ala Ser Ala Pro
                20

<210> SEQ ID NO 64
<211> LENGTH: 33
<212> TYPE: PRT
<213> ORGANISM: Artificial Sequence
<220> FEATURE:
<223> OTHER INFORMATION: Artificially synthesized linker

<400> SEQUENCE: 64

Ser Ala Pro Ala Pro Ser Ala Pro Ala Ala Ser Ala Pro Pro Ala Pro
1               5                   10                  15

Ala Ala Ala Pro Ala Ala Pro Ala Pro Ala Pro Ser Ala Pro Ala Pro
                20                  25                  30

Ala

<210> SEQ ID NO 65
<211> LENGTH: 33
<212> TYPE: PRT
<213> ORGANISM: Artificial Sequence
<220> FEATURE:
<223> OTHER INFORMATION: Artificially synthesized linker

<400> SEQUENCE: 65

Ala Pro Ala Ala Ser Pro Ser Pro Ala Ala Pro Ala Pro Ser Pro
1               5                   10                  15

Ala Ser Pro Ala Pro Ala Ser Pro Ala Ser Ala Pro Ser Ala Pro Ala
                20                  25                  30
```

Ser

<210> SEQ ID NO 66
<211> LENGTH: 35
<212> TYPE: PRT
<213> ORGANISM: Artificial Sequence
<220> FEATURE:
<223> OTHER INFORMATION: Artificially synthesized linker

<400> SEQUENCE: 66

Pro Pro Ala Ala Pro Ser Ala Ala Ser Ser Pro Ala Pro Ser Ala Pro
1               5                   10                  15

Ala Pro Ala Ala Ala Ser Pro Ala Ala Ala Pro Ala Ser Ala Ala Pro
            20                  25                  30

Ala Ser Ala
        35

<210> SEQ ID NO 67
<211> LENGTH: 20
<212> TYPE: PRT
<213> ORGANISM: Artificial Sequence
<220> FEATURE:
<223> OTHER INFORMATION: Artificially synthesized linker

<400> SEQUENCE: 67

Ser Ala Pro Ala Pro Ser Ala Pro Ala Ala Ser Ala Pro Pro Ala
1               5                   10                  15

Pro Ala Ala Pro
            20

<210> SEQ ID NO 68
<211> LENGTH: 20
<212> TYPE: PRT
<213> ORGANISM: Artificial Sequence
<220> FEATURE:
<223> OTHER INFORMATION: Artificially synthesized linker

<400> SEQUENCE: 68

Ala Pro Ala Ala Ala Pro Ala Ser Ala Pro Ala Pro Ala Ser Ala Pro
1               5                   10                  15

Ala Ala Ser Pro
            20

<210> SEQ ID NO 69
<211> LENGTH: 22
<212> TYPE: PRT
<213> ORGANISM: Artificial Sequence
<220> FEATURE:
<223> OTHER INFORMATION: Artificially synthesized linker

<400> SEQUENCE: 69

Pro Ala Ala Ala Pro Ala Pro Ser Pro Ala Ser Pro Ala Pro Ala Ser
1               5                   10                  15

Pro Ala Pro Ser Ser Ala
            20

<210> SEQ ID NO 70
<211> LENGTH: 41
<212> TYPE: PRT
<213> ORGANISM: Artificial Sequence
<220> FEATURE:
<223> OTHER INFORMATION: Artificially synthesized linker

<400> SEQUENCE: 70

Ser Ala Pro Ala Pro Ser Ala Pro Ala Ala Ser Ala Pro Ala Pro
1               5                   10                  15

Ala Ala Pro Ala Ala Pro Ala Pro Ala Ser Ala Pro Ala Pro
            20                  25                  30

Ala Pro Ala Pro Ala Ala Ser Pro Ser
        35                  40

<210> SEQ ID NO 71
<211> LENGTH: 41
<212> TYPE: PRT
<213> ORGANISM: Artificial Sequence
<220> FEATURE:
<223> OTHER INFORMATION: Artificially synthesized linker

<400> SEQUENCE: 71

Ser Ala Pro Ala Ala Ser Pro Ser Pro Ala Ala Ala Pro Ala Pro Ser
1               5                   10                  15

Pro Ala Ser Pro Ala Pro Ala Ser Pro Ala Ser Ala Pro Ser Ala Pro
            20                  25                  30

Ala Ser Ala Pro Pro Ala Ala Ser Ala
        35                  40

<210> SEQ ID NO 72
<211> LENGTH: 21
<212> TYPE: PRT
<213> ORGANISM: Artificial Sequence
<220> FEATURE:
<223> OTHER INFORMATION: Artificially synthesized linker

<400> SEQUENCE: 72

Pro Ala Ala Ala Pro Ala Pro Ser Pro Ala Ser Pro Ala Pro Ala Ser
1               5                   10                  15

Pro Ala Ser Ala Pro
            20

<210> SEQ ID NO 73
<211> LENGTH: 41
<212> TYPE: PRT
<213> ORGANISM: Artificial Sequence
<220> FEATURE:
<223> OTHER INFORMATION: Artificially synthesized linker and coupling
      site L1C1-L2C2

<400> SEQUENCE: 73

Ser Ala Pro Ala Pro Ser Ala Pro Ala Ala Ser Ala Pro Ala Pro
1               5                   10                  15

Ala Ala Pro Cys Ala Pro Ala Ala Ala Pro Ala Ser Ala Pro Ala Pro
            20                  25                  30

Ala Ser Ala Pro Ala Ala Ser Pro Cys
        35                  40

<210> SEQ ID NO 74
<211> LENGTH: 61
<212> TYPE: PRT
<213> ORGANISM: Artificial Sequence
<220> FEATURE:
<223> OTHER INFORMATION: Artificially synthesized linker and coupling
      site L1C1-L2C2-cap

<400> SEQUENCE: 74

Ser Ala Pro Ala Pro Ser Ala Pro Ala Ala Ser Ala Pro Pro Ala Pro
1               5                   10                  15

Ala Ala Pro Cys Ala Pro Ala Ala Pro Ala Ser Ala Pro Ala Pro
            20                  25                  30

Ala Ser Ala Pro Ala Ala Ser Pro Cys Pro Ala Ala Pro Ala Pro Ser
        35                  40                  45

Pro Ala Ser Pro Ala Pro Ala Ser Pro Ala Ser Ala Pro
    50                  55                  60

<210> SEQ ID NO 75
<211> LENGTH: 40
<212> TYPE: PRT
<213> ORGANISM: Artificial Sequence
<220> FEATURE:
<223> OTHER INFORMATION: Artificially synthesized linker and coupling
      site L1C1-L2C2

<400> SEQUENCE: 75

Ser Ala Pro Ala Pro Ser Ala Pro Ala Ala Ser Ala Pro Pro Ala Pro
1               5                   10                  15

Ala Ala Pro Cys Ala Pro Ala Ala Pro Ala Ser Ala Pro Ala Pro Ala
            20                  25                  30

Ser Ala Pro Ala Ala Ser Pro Cys
        35                  40

<210> SEQ ID NO 76
<211> LENGTH: 60
<212> TYPE: PRT
<213> ORGANISM: Artificial Sequence
<220> FEATURE:
<223> OTHER INFORMATION: Artificially synthesized linker and coupling
      site L1C1-L2C2-cap

<400> SEQUENCE: 76

Ser Ala Pro Ala Pro Ser Ala Pro Ala Ala Ser Ala Pro Pro Ala Pro
1               5                   10                  15

Ala Ala Pro Cys Ala Pro Ala Ala Pro Ala Ser Ala Pro Ala Pro Ala
            20                  25                  30

Ser Ala Pro Ala Ala Ser Pro Cys Pro Ala Ala Pro Ala Pro Ser Pro
        35                  40                  45

Ala Ser Pro Ala Pro Ala Ser Pro Ala Ser Ala Pro
    50                  55                  60

<210> SEQ ID NO 77
<211> LENGTH: 20
<212> TYPE: PRT
<213> ORGANISM: Artificial Sequence
<220> FEATURE:
<223> OTHER INFORMATION: Artificially synthesized linker with coupling
      site

<400> SEQUENCE: 77

Ser Ala Pro Ala Pro Ser Ala Pro Ala Ala Ser Ala Pro Pro Ala Pro
1               5                   10                  15

Ala Ala Pro Cys
            20

<210> SEQ ID NO 78
<211> LENGTH: 20
<212> TYPE: PRT
<213> ORGANISM: Artificial Sequence
<220> FEATURE:
<223> OTHER INFORMATION: Artificially synthesized linker with coupling
      site

<400> SEQUENCE: 78

```
Ala Pro Ala Ala Pro Ala Ser Ala Pro Ala Pro Ala Ser Ala Pro Ala
1               5                   10                  15

Ala Ser Pro Cys
            20

<210> SEQ ID NO 79
<211> LENGTH: 33
<212> TYPE: PRT
<213> ORGANISM: Artificial Sequence
<220> FEATURE:
<223> OTHER INFORMATION: Artificially synthesized linker with coupling
      site

<400> SEQUENCE: 79

Ser Ala Pro Ala Pro Ser Ala Pro Ala Ala Ser Ala Pro Pro Ala Pro
1               5                   10                  15

Ala Ala Pro Ala Ala Pro Ala Ala Pro Ala Ser Ala Pro Ala Pro Ala
                20                  25                  30

Cys

<210> SEQ ID NO 80
<211> LENGTH: 33
<212> TYPE: PRT
<213> ORGANISM: Artificial Sequence
<220> FEATURE:
<223> OTHER INFORMATION: Artificially synthesized linker with coupling
      site

<400> SEQUENCE: 80

Ala Pro Ala Ala Ser Pro Ser Pro Ala Ala Pro Ala Pro Ser Pro Ala
1               5                   10                  15

Ser Pro Ala Pro Ala Ser Pro Ala Ser Ala Pro Ser Ala Pro Ala Ser
                20                  25                  30

Cys

<210> SEQ ID NO 81
<211> LENGTH: 5
<212> TYPE: PRT
<213> ORGANISM: Artificial Sequence
<220> FEATURE:
<223> OTHER INFORMATION: Artificially synthesized coupling site
<220> FEATURE:
<221> NAME/KEY: variant
<222> LOCATION: (2)..(4)
<223> OTHER INFORMATION: Xaa can be any amino acid selected from Pro,
      Ala, Ser, Val, Gly, Thr, Ser, Asn , Asp, Gln, Glu, Lys, Arg, His

<400> SEQUENCE: 81

Cys Xaa Xaa Xaa Cys
1               5
```